United States Patent
Askari et al.

(10) Patent No.: US 10,111,985 B2
(45) Date of Patent: *Oct. 30, 2018

(54) BIOCOMPATIBLE HYDROGEL POLYMER FORMULATIONS FOR THE CONTROLLED DELIVERY OF BIOMOLECULES

(75) Inventors: Syed H. Askari, San Jose, CA (US); Yeon S. Choi, Emeryville, CA (US); George Horng, Millbrae, CA (US)

(73) Assignee: MEDICUS BIOSCIENCES, LLC, San Francisco, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 13/571,116

(22) Filed: Aug. 9, 2012

(65) Prior Publication Data

US 2014/0302051 A1 Oct. 9, 2014

Related U.S. Application Data

(60) Provisional application No. 61/522,148, filed on Aug. 10, 2011, provisional application No. 61/557,854, filed on Nov. 9, 2011.

(51) Int. Cl.
| | | |
|---|---|---|
| A61K 9/00 | (2006.01) | |
| A61K 39/00 | (2006.01) | |
| A61K 39/395 | (2006.01) | |
| A61K 38/02 | (2006.01) | |
| A61L 27/50 | (2006.01) | |

(Continued)

(52) U.S. Cl.
CPC ............ *A61L 27/50* (2013.01); *A61K 9/0024* (2013.01); *A61K 47/34* (2013.01); *A61L 27/52* (2013.01); *A61L 27/54* (2013.01); *A61L 2400/06* (2013.01)

(58) Field of Classification Search
None
See application file for complete search history.

(56) References Cited

U.S. PATENT DOCUMENTS 5,037,384 A 8/1991 Chang
5,135,755 A 8/1992 Czech et al.
(Continued)

FOREIGN PATENT DOCUMENTS

CA 2750242 A1 8/2010
JP 2011-505420 A 2/2011
(Continued)

OTHER PUBLICATIONS

Ballico, M., et al., MultiPEGs: High Molecular Weight Multifunctional Poly(ethylene glycol)s Assembled by a Dendrimer-Like Approach, Eur. J. Org. Chem. (2005) pp. 2064-2073.*

(Continued)

*Primary Examiner* — Bethany P Barham
*Assistant Examiner* — Dominic Lazaro
(74) *Attorney, Agent, or Firm* — Pepper Hamilton LLP

(57) ABSTRACT

Provided herein are biocompatible hydrogel polymers capable of gelling in vivo comprising a therapeutic agent such as a protein or other biomolecule and kits comprising at least one nucleophilic compound or monomer unit, at least one electrophilic compound or monomer unit, and at least one therapeutic agent. The biocompatible hydrogel polymer is bioabsorbable and releases the therapeutic agent at a target site, avoiding systemic exposure and achieving a controlled delivery.

18 Claims, 9 Drawing Sheets

(51) Int. Cl.
*A61L 27/54* (2006.01)
*A61K 47/34* (2017.01)
*A61L 27/52* (2006.01)

(56) References Cited

U.S. PATENT DOCUMENTS

| | | |
|---|---|---|
| 5,336,175 A | 8/1994 | Mames |
| 5,858,345 A | 1/1999 | Charles et al. |
| 5,874,500 A | 2/1999 | Rhee et al. |
| 6,051,648 A | 4/2000 | Rhee et al. |
| 6,135,118 A | 10/2000 | Dailey |
| 6,149,931 A | 11/2000 | Schwartz et al. |
| 6,153,211 A | 11/2000 | Hubbell et al. |
| 6,180,687 B1 | 1/2001 | Hammer et al. |
| 6,207,772 B1 | 3/2001 | Hatsuda et al. |
| 6,312,725 B1 | 11/2001 | Wallace et al. |
| 6,458,889 B1 | 10/2002 | Trollsas et al. |
| 6,475,508 B1 | 11/2002 | Schwartz et al. |
| 6,547,714 B1 | 4/2003 | Dailey |
| 6,566,406 B1 | 5/2003 | Pathak et al. |
| 6,605,294 B2 | 8/2003 | Sawhney |
| 6,624,245 B2 | 9/2003 | Wallace et al. |
| 6,632,457 B1 | 10/2003 | Sawhney |
| 6,703,037 B1 | 3/2004 | Hubbell et al. |
| 6,703,378 B1 | 3/2004 | Kunzler et al. |
| 6,818,018 B1 | 11/2004 | Sawhney et al. |
| 7,255,874 B1 | 8/2007 | Bobo et al. |
| 8,388,995 B1 | 3/2013 | All et al. |
| 8,765,787 B2 | 7/2014 | Aberg et al. |
| 8,987,339 B2 | 3/2015 | Askari et al. |
| 9,072,809 B2* | 7/2015 | Askari .............. A61K 9/0051 |
| 9,149,560 B2 | 10/2015 | Askari et al. |
| 9,623,144 B2* | 4/2017 | Askari .............. A61L 26/0019 |
| 2001/0003126 A1 | 6/2001 | Rhee et al. |
| 2001/0055615 A1 | 12/2001 | Wallace et al. |
| 2002/0042473 A1 | 4/2002 | Trollsas et al. |
| 2002/0106409 A1 | 8/2002 | Sawhney |
| 2002/0114775 A1 | 8/2002 | Pathak |
| 2002/0165337 A1 | 11/2002 | Wallace et al. |
| 2003/0195113 A1 | 10/2003 | Nakamura et al. |
| 2003/0223957 A1 | 12/2003 | Schwartz et al. |
| 2004/0009205 A1 | 1/2004 | Sawhney |
| 2004/0018228 A1 | 1/2004 | Fischell et al. |
| 2004/0023842 A1 | 2/2004 | Pathak et al. |
| 2004/0033264 A1 | 2/2004 | Sawhney |
| 2004/0203149 A1* | 10/2004 | Childs et al. .............. 435/404 |
| 2005/0027069 A1 | 2/2005 | Rhee et al. |
| 2005/0191277 A1 | 9/2005 | Sawhney et al. |
| 2005/0200295 A1 | 9/2005 | Lim et al. |
| 2005/0203333 A1 | 9/2005 | Dailey |
| 2005/0208102 A1 | 9/2005 | Schultz |
| 2005/0255039 A1 | 11/2005 | Desai |
| 2005/0281802 A1 | 12/2005 | Gong et al. |
| 2005/0281883 A1 | 12/2005 | Daniloff et al. |
| 2006/0057208 A1 | 3/2006 | Holzer et al. |
| 2006/0065199 A1 | 3/2006 | Davis |
| 2006/0115457 A1 | 6/2006 | Hnojewyj |
| 2006/0147409 A1 | 7/2006 | Pathak et al. |
| 2006/0159771 A1 | 7/2006 | Kadrmas |
| 2006/0222596 A1 | 10/2006 | Askari et al. |
| 2007/0110813 A1 | 5/2007 | Ingenito et al. |
| 2008/0095736 A1 | 4/2008 | Pathak et al. |
| 2008/0115787 A1 | 5/2008 | Ingenito |
| 2008/0159975 A1* | 7/2008 | Nho et al. .............. 424/70.11 |
| 2008/0160085 A1 | 7/2008 | Boland et al. |
| 2008/0214695 A1 | 9/2008 | Pathak et al. |
| 2008/0261884 A1 | 10/2008 | Tsai et al. |
| 2008/0279944 A1 | 11/2008 | Sawhney |
| 2008/0281352 A1 | 11/2008 | Ingenito et al. |
| 2009/0087443 A1* | 4/2009 | Bartels .............. A61K 31/00 424/158.1 |
| 2009/0170811 A1 | 7/2009 | Garvey et al. |
| 2009/0196928 A1* | 8/2009 | Hnojewyj .............. 424/486 |
| 2009/0215923 A1 | 8/2009 | Carnahan et al. |
| 2010/0040538 A1 | 2/2010 | Ingenito et al. |
| 2010/0055078 A1 | 3/2010 | Hughes-Fulford |
| 2010/0113476 A1* | 5/2010 | Chen et al. .............. 514/254.08 |
| 2011/0081701 A1 | 4/2011 | Sargeant et al. |
| 2011/0091551 A1 | 4/2011 | Baur et al. |
| 2012/0295869 A1* | 11/2012 | Liu .............. A61L 2/022 514/54 |
| 2013/0108711 A1 | 5/2013 | Askari et al. |
| 2013/0116341 A1 | 5/2013 | Askari et al. |
| 2014/0248231 A1 | 9/2014 | Askari et al. |
| 2014/0271528 A1 | 9/2014 | Askari et al. |
| 2014/0271767 A1 | 9/2014 | Askari et al. |
| 2015/0190544 A1 | 7/2015 | Askari et al. |
| 2015/0272987 A1 | 10/2015 | Askari et al. |
| 2015/0273108 A1 | 10/2015 | Askari et al. |

FOREIGN PATENT DOCUMENTS

| | | | |
|---|---|---|---|
| JP | 201281252 A | 4/2012 | |
| WO | WO-1997-22371 | 6/1997 | |
| WO | WO-1999-003454 | 1/1999 | |
| WO | WO-2001-010416 | 2/2001 | |
| WO | WO-2002-053526 | 7/2002 | |
| WO | 2002/062276 A1 | 8/2002 | |
| WO | WO-02102864 A1 | 12/2002 | |
| WO | WO-2004-021983 | 3/2004 | |
| WO | WO-2006-030431 | 3/2006 | |
| WO | WO-2007016622 A2 | 2/2007 | |
| WO | WO-2008-141059 | 11/2008 | |
| WO | 2009/073192 A2 | 6/2009 | |
| WO | WO-2009-123768 | 10/2009 | |
| WO | WO-2009-132153 | 10/2009 | |
| WO | WO 2010064251 A1 * | 6/2010 | |
| WO | WO-2010076400 A1 * | 7/2010 | ......... C07K 16/2887 |
| WO | WO-2011-057131 | 5/2011 | |
| WO | WO-2011-066291 | 6/2011 | |
| WO | WO-2011-140671 | 11/2011 | |
| WO | WO-2011-140519 | 11/2011 | |
| WO | 2012050591 A1 | 4/2012 | |
| WO | WO-2012057628 A2 | 5/2012 | |

OTHER PUBLICATIONS

3M Company, 3M™ Vetbond™ Veterinary Tissue Adhesive, Material Safety Data Sheet, Jun. 1, 2009.
Abbott Animal Health, GLUture®, Information Brochure, Feb. 2009.
Baino, "Towards an ideal biomaterial for vitreous replacement: Historical overview and future trends," Acta Biomaterialia 7: 921-935 (2011).
Brandi et al., "Biodegradable hydrogels for time-controlled release of tethered peptides or proteins," Biomacromolecules 11: 496-504 (2010).
Campbell et al., "Evaluation of the PleuraSeal™ Lung Sealant System as a Thoracic Sealant in a Canine Lung Resection Model," Covidien (2007).
Creative PEGWorks, Multiarm PEG materials, PEG product Catalog, last updated Dec. 31, 2012.
Dango et al., "Initial experience with a synthetic sealant PleuraSeal™ after pulmonary resections: a prospective study with retrospective case matched controls," Journal of Cardiothoracic Surgery 5: 50-58 (2010).
Ethicon, Inc., Ethicon™ Dermabond Advanced™, Instructions for Use, Status Mar. 2011.
Jemyork Biotechnology, Multiarm PEG materials, web pages printed from www.jemyork.com/proshow.aspx?id=131 on Feb. 12, 2013.
JenKem Technology, USA, Multiarm PEG materials, PEG Products Catalog, 2011.
NanoCS, Inc., Multiarm PEG Derivatives, web pages printed from http://www.nanocs.com/PEG/MAPEG.htm on Feb. 12, 2013.
NeoMend, Inc., ProGEL®, Instructions for Use and Product Labeling, Jan. 4, 2012.
NOF Corporation, Drug Delivery Systems, Catalogue Ver. 13, Prepared Oct. 2011.
Preul et al., "Application of a new hydrogel dural sealant that reduces epidural adhesion formation: evaluation in a large animal laminectomy model," J Neurosurg Spine 12: 381-390 (2010).

(56) References Cited

OTHER PUBLICATIONS

International Search Report and Written Opinion for PCT/US2011/035640, dated Jan. 19, 2012.
International Search Report and Written Opinion for PCT/US2011/035643, dated Jan. 19, 2012.
PCT/US2014/028622 International Search Report dated Jul. 7, 2014.
U.S. Appl. No. 14/212,457 Office Action dated Jun. 9, 2014.
U.S. Appl. No. 13/696,032 Office Action dated Jun. 12, 2014.
U.S. Appl. No. 13/696,028 Office Action dated Jun. 12, 2014.
U.S. Appl. No. 14/213,520 Office Action dated Jul. 3, 2014.
PCT/US2014/028798 International Search Report dated Aug. 26, 2014.
U.S. Appl. No. 13/696,028 Office Action dated Nov. 7, 2014.
U.S. Appl. No. 14/273,408 Office Action dated Aug. 29, 2014.
U.S. Appl. No. 14/273,408 Office Action dated Nov. 18, 2014.
International Search Report and Written Opinion for PCT/US2013/40619 dated Sep. 27, 2013.
JenKem Technology USA, "Multi-arm PEG Derivatives," accessed Oct. 7, 2013, http://www.jenkemusa.com/Pages/MultiarmPEGs.aspx.
Lazzarin et al., N. Engl. J. Med., 348(22):2186-2195 (2003).
Marcus et al., J. Bone Miner. Res. 18:18-23 (2003).
Neer et al., New Engl. J. Med., 344:1434-1441 (2001).
U.S. Appl. No. 13/696,028 Office Action dated Dec. 31, 2013.
U.S. Appl. No. 13/696,032 Office Action dated Oct. 22, 2013.
U.S. Appl. No. 13/696,032 Office Action dated Dec. 10, 2014.
U.S. Appl. No. 14/213,520 Office Action dated Dec. 15, 2014.
Sardari et al. Evaluation of Clinical Examination for Differential Diagnosis of Lameness by Navicular Apparatus or Heel Pain in Horses. Pakistan Journal of Biological Sciences 11(13):1754-1756 (2008).
U.S. Appl. No. 13/696,028 Office Action dated Jul. 17, 2015.
U.S. Appl. No. 13/696,032 Office Action dated Jul. 17, 2015.
U.S. Appl. No. 14/722,829 Office Action dated Aug. 18, 2015.
U.S. Appl. No. 14/739,917 Office Action dated Aug. 4, 2015.
U.S. Appl. No. 14/739,917 Office Action dated Jan. 22, 2016.
Co-pending U.S. Appl. No. 14/947,818, filed Nov. 20, 2015.
U.S. Appl. No. 13/696,032 Office Action dated Jun. 8, 2016.
U.S. Appl. No. 14/722,829 Office Action dated Feb. 5, 2016.
U.S. Appl. No. 14/739,917 Office Action dated May 11, 2016.
U.S. Appl. No. 14/947,818 Office Action dated May 9, 2016.
Goudar. Review of pemetrexed in combination with cisplatin for the treatment of malignant pleural mesothelioma. Ther Clin Risk Manag 4(1):205-211 (2008).
U.S. Appl. No. 13/696,028 Office Action dated Sep. 2, 2016.
U.S. Appl. No. 14/722,829 Office Action dated Aug. 24, 2016.
U.S. Appl. No. 13/696,032 Office Action dated Jan. 6, 2017.
Ostroha. PEG-based Degradable Networks for Drug Delivery Applications. Thesis (165 pgs.) (Jun. 2006).
U.S. Appl. No. 14/739,917 Office Action dated Nov. 25, 2016.
U.S. Appl. No. 14/947,818 Office Action dated Nov. 23, 2016.
Co-pending U.S. Appl. No. 14/618,804, filed Feb. 10, 2015.
Co-pending U.S. Appl. No. 14/722,879, filed May 27, 2015.
Co-pending U.S. Appl. No. 14/739,917, filed Jun. 15, 2015.
EP1317998.3 Search Report dated Feb. 13, 2014.
Nicodemus et al., Cell encapsulation in biodegradable hydrogels for tissue engineering applications, Tissue Engineering Part B 2008 14(2):149-165.
U.S. Appl. No. 14/739,917 Office Action dated Jun. 13, 2017.
U.S. Appl. No. 14/722,829 Notice of Allowance dated Feb. 10, 2017.
U.S. Appl. No. 14/947,818 Office Action dated Apr. 16, 2018.
U.S. Appl. No. 15/467,019, Nonfinal Office Action dated Mar. 8, 2018.

* cited by examiner

Figure 1
Figure 1A
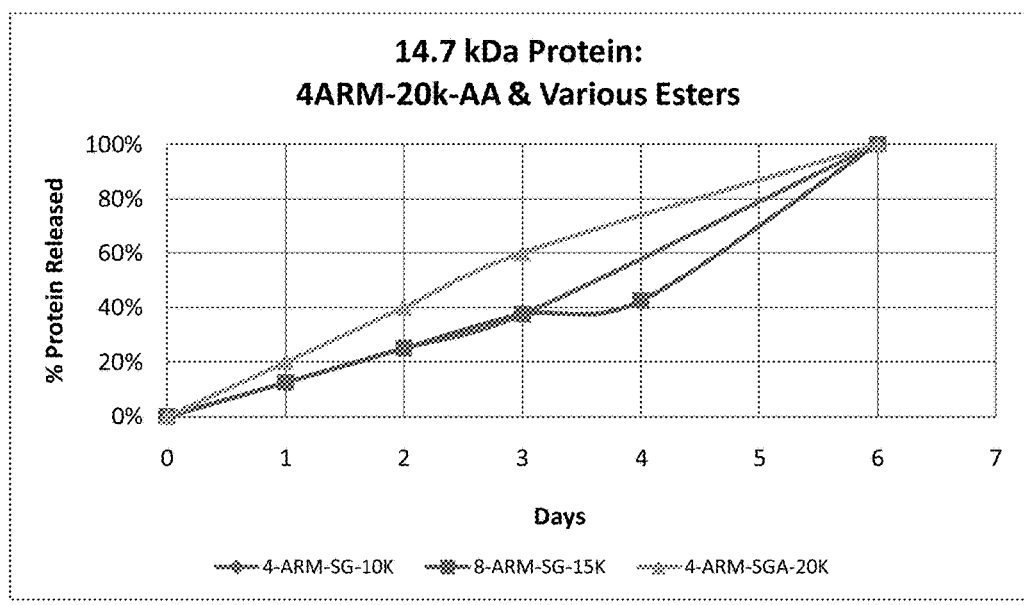
Figure 1B
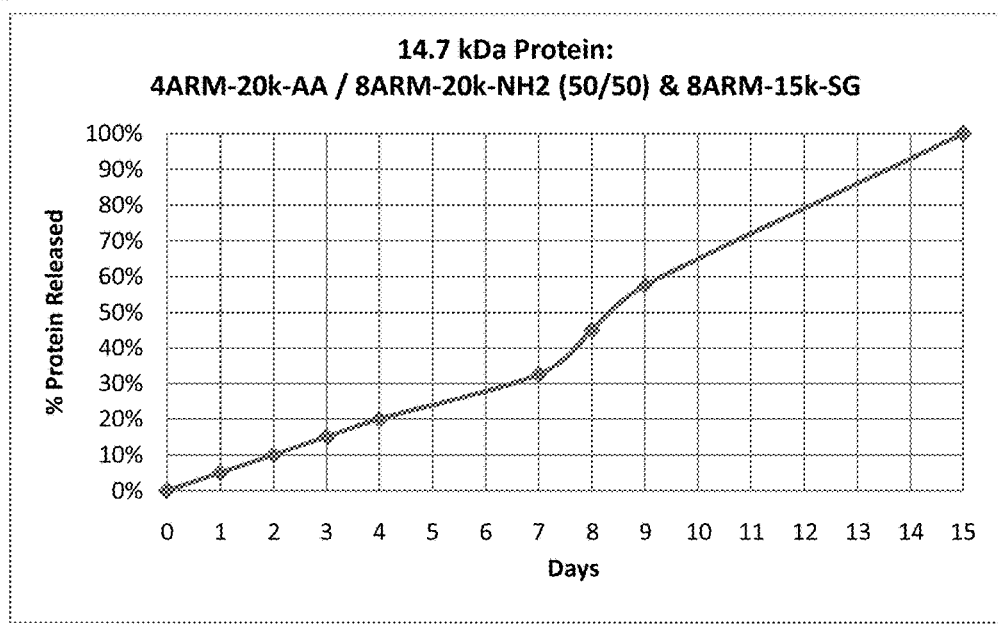

Figure 2
Figure 2A
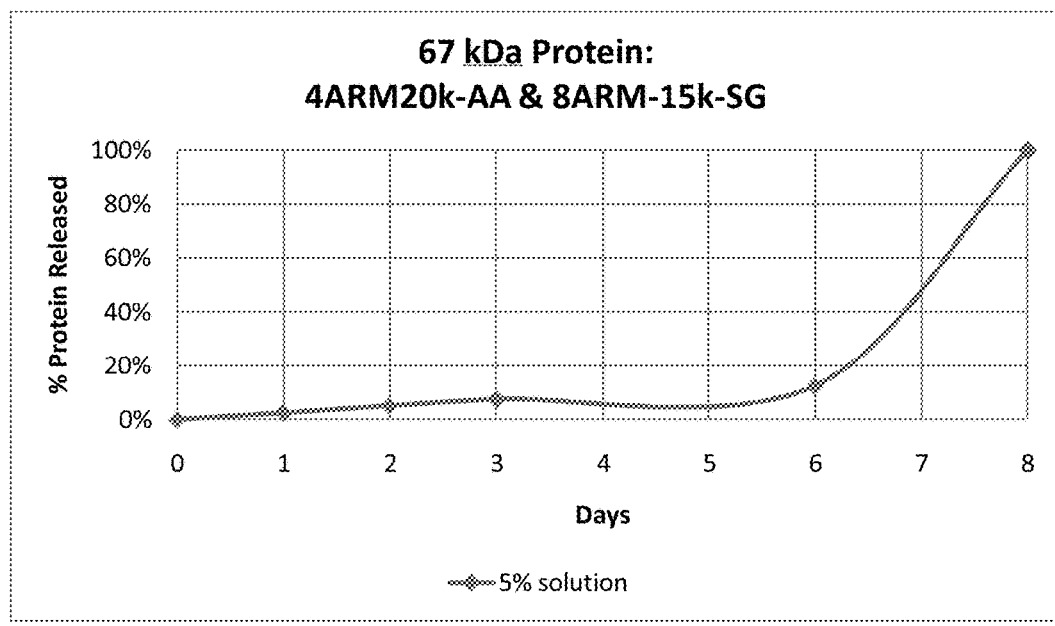
Figure 2B
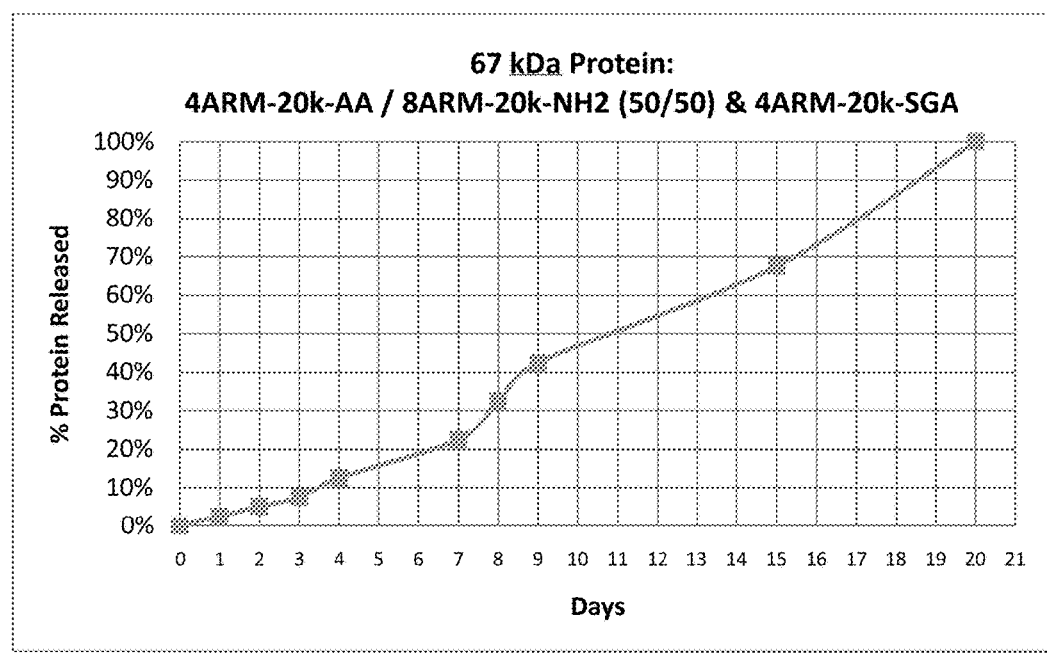

BIOCOMPATIBLE HYDROGEL POLYMER FORMULATIONS FOR THE CONTROLLED DELIVERY OF BIOMOLECULES

CROSS REFERENCE

This application claims the benefit of U.S. Provisional Application No. 61/557,854, filed Nov. 9, 2011, and U.S. Provisional Application No. 61/522,148, filed Aug. 10, 2011, which are entirely incorporated herein by reference.

BACKGROUND OF THE INVENTION

Every year millions of people undergo systemic treatments, such as chemotherapy for cancers, inflammatory diseases, and chronic conditions. Systemic treatments, in which medications are injected or absorbed into the bloodstream an circulated throughout the body, are currently the only viable option to reach the site of these diseases even though in most cases the disease is localized in a specific organ.

SUMMARY OF THE INVENTION

Provided herein are in vivo gelling pharmaceutical pre-formulations, biocompatible hydrogel polymers, in vivo polymerized biocompatible hydrogel polymers, and kits for preparing in vivo gelling pharmaceutical pre-formulations, biocompatible hydrogel polymers, and in vivo polymerized biocompatible hydrogel polymers. The pre-formulations and hydrogel polymers comprise a mixture of compounds that safely undergo polymerization to form a biocompatible hydrogel polymer at a target site. Using a minimally invasive delivery system (e.g., endoscopic or image guided), the polymeric hydrogel formulation is delivered to the target site, where the pre-formulation solidifies into a biocompatible hydrogel polymer at a predetermined time to remain at the site of delivery. In some embodiments, the biocompatible hydrogel polymer comprises one or more therapeutic agents that are released over time from the hydrogel polymer at the target site, limiting exposure of healthy cells to the therapeutic agent. In certain embodiments, the biocompatible hydrogel polymer degrades over time and is bioabsorbed. In some embodiments, the therapeutic agent is a biomolecule and the release of the biomolecule from the hydrogel polymer is controlled by the composition of the hydrogel polymer. In certain embodiments, the pore size of the hydrogel polymer is small enough to prevent the early phase release of the biomolecule. In some embodiments, the biomolecule is released when the hydrogel polymer starts to degrade. In certain embodiments, the pore size of the hydrogel polymer is large enough to allow the early phase release of the biomolecule. In some embodiments, the ratio of the pore size of the hydrogel polymer to the size of the biomolecule determines the release rate of the biomolecule.

In one aspect provided herein is an in vivo gelling pharmaceutical pre-formulation, comprising (a) at least one first compound comprising more than one nucleophilic group, (b) at least one second compound comprising more than one electrophilic group, (c) an aqueous buffer in the pH range of about 5.0 to about 9.5; and (d) at least one therapeutic agent; wherein the in vivo gelling pharmaceutical pre-formulation at least in part polymerizes and/or gels at a target site of a human body to form a biocompatible hydrogel polymer. In some embodiments, the target site is in the human body. In certain embodiments, the target site is on the human body.

In some embodiments, the therapeutic agent is a pharmaceutically active biomolecule. In certain embodiments, the therapeutic agent is a protein or peptide. In some embodiments, the therapeutic agent is a monoclonal antibody. In certain embodiments, the therapeutic agent is a vaccine.

In some embodiments, the nucleophilic group is a thiol or amino group. In certain embodiments, the first compound is a glycol, trimethylolpropane, pentaerythritol, hexaglycerol, or tripentaerythritol derivative. In preferred embodiments, the first compound is a pentaerythritol or hexaglycerol derivative. In certain embodiments, the first compound further comprises one or more polyethylene glycol sections. In some embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, and ethoxylated hexaglycerol amino acetate. In certain embodiments, the first compound is selected from the group consisting of trimethylolpropane trimercaptoacetate, trimethylolpropane tri-3-mercaptopropionate, pentaerythritol tetramercaptoacetate, pentaerythritol tetra-3-mercaptopropionate, ethoxylated trimethylolpropane trimercaptoacetate, ethoxylated trimethylolpropane tri-3-mercaptopropionate, ethoxylated pentaerythritol tetramercaptoacetate, and ethoxylated trimethylolpropane tri-3-mercaptopropionate. In some embodiments, the molecular weight of the first compound is between about 1000 and 40000. In certain embodiments, the first compound is water soluble.

In certain embodiments, the electrophilic group is an epoxide, N-succinimidyl succinate, N-succinimidyl glutarate, N-succinimidyl succinamide or N-succinimidyl glutaramide. In some embodiments, the second compound is a trimethylolpropane, glycerol, digylcerol, pentaerythritol, sorbitol, hexaglycerol, tripentaerythritol, or polyglycerol derivative. In preferred embodiments, the second compound is a trimethylolpropane, pentaerythritol, or hexaglycerol derivative. In some embodiments, the second compound further comprises one or more polyethylene glycol sections. In certain embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, and ethoxylated hexaglycerol succinimidyl glutaramide. In some embodiments, the second compound is selected from the group consisting of sorbitol polyglycidyl ether, polyglycerol polyglycidyl ether, digylcerol polyglycidyl ether, glycerol polyglycidyl ether, and trimethylolpropane polyglycidyl ether. In certain embodiments, the molecular weight of the second compound is between about 1000 and 40000. In some embodiments, the second compound is water soluble.

In certain embodiments, the gelling time of the biocompatible hydrogel polymer is controlled by the pH of the aqueous buffer. In some embodiments, the gelling time of the biocompatible hydrogel polymer is controlled by the type of the buffer. In certain embodiments, the gelling time of the biocompatible hydrogel polymer is controlled by the type and pH of the buffer. In some embodiments, the gelling time is between about 20 seconds and 10 minutes. In certain embodiments, the pH of the aqueous buffer is from about 7 to about 9. In some embodiments, the pH of the aqueous buffer is about 8. In certain embodiments, the biocompatible hydrogel polymer gels at a predetermined time. In some embodiments, the biocompatible hydrogel polymer is a bioabsorbable polymer. In certain embodiments, the biocompatible hydrogel polymer is bioabsorbed within about 1 to 70 days. In some embodiments, the biocompatible hydrogel polymer is substantially non-bioabsorbable. In certain embodiments, the in vivo gelling pharmaceutical pre-formulation further comprises a radiopaque material or a pharmaceutically acceptable dye. In certain embodiments, the radiopaque material is selected from sodium iodide, potassium iodide, barium sulfate, tantalum, VISIPAQUE®, OMNIPAQUE®, or HYPAQUE®, or combinations thereof.

In some embodiments, the therapeutic agent is released from the biocompatible hydrogel polymer through diffusion, osmosis, degradation of the biocompatible hydrogel polymer, or any combination thereof. In certain embodiments, the therapeutic agent is initially released from the biocompatible hydrogel polymer through diffusion and later released through degradation of the biocompatible hydrogel polymer. In some embodiments, the therapeutic agent is substantially released from the biocompatible hydrogel polymer within 180 days. In certain embodiments, the therapeutic agent is substantially released from the biocompatible hydrogel polymer within 14 days. In some embodiments, the therapeutic agent is substantially released from the biocompatible hydrogel polymer within 24 hours. In certain embodiments, the therapeutic agent is substantially released from the biocompatible hydrogel polymer within one hour. In some embodiments, the first compound and the second compound do not react with the therapeutic agent during formation of the biocompatible hydrogel polymer. In certain embodiments, the biocompatible hydrogel polymer interacts with the therapeutic agent, and wherein more than 10% of the therapeutic agent is released through degradation of the biocompatible hydrogel polymer. In some embodiments, more than 30% of the therapeutic agent is released through degradation of the biocompatible hydrogel polymer. In certain embodiments, the biocompatible hydrogel polymer interacts with the therapeutic agent by forming covalent bonds between the biocompatible hydrogel polymer and the therapeutic agent. In some embodiments, the biocompatible hydrogel polymer interacts with the therapeutic agent by forming a non-covalent bond between the biocompatible hydrogel polymer and the therapeutic agent.

In certain embodiments, the release of the therapeutic agent is determined by the composition of the biocompatible hydrogel polymer. In some embodiments, the therapeutic agent is released while the biocompatible hydrogel polymer degrades. In certain embodiments, the release of the therapeutic agent is essentially inhibited until a time that the biocompatible hydrogel polymer starts to degrade. In some embodiments, the biocompatible hydrogel polymer has a pore size, wherein the pore size is small enough to essentially inhibit the release of the therapeutic agent before the time that the biocompatible hydrogel polymer starts to degrade. In certain embodiments, the ratio of the pore size of the biocompatible hydrogel polymer to the size of the therapeutic agent is less than 8. In some embodiments, at least a portion of the therapeutic agent is released before the time that the biocompatible hydrogel polymer starts to degrade. In certain embodiments, the biocompatible hydrogel polymer has a pore size, wherein the pore size is large enough to allow at least a partial release of the therapeutic agent before the time that the biocompatible hydrogel polymer starts to degrade. In some embodiments, the ratio of the pore size of the biocompatible hydrogel polymer to the size of the therapeutic agent is more than 8 and less than 12. In certain embodiments, the time the biocompatible hydrogel polymer starts to degrade is longer the higher a degree of cross-linking of the biocompatible hydrogel polymer. In some embodiments, the time the biocompatible hydrogel polymer starts to degrade is shorter the higher a concentration of ester groups in the first or second compound.

In another aspect provided herein is a biocompatible hydrogel polymer made by mixing (a) at least one first compound comprising more than one nucleophilic group, (b) at least one second compound comprising more than one electrophilic group, (c) an aqueous buffer in the pH range of about 5.0 to about 9.5, and (d) at least one therapeutic agent. In some embodiments, the mixing is performed outside a human body, and the biocompatible hydrogel polymer gels inside the human body. In certain embodiments, the mixing is performed outside the human body, and the biocompatible hydrogel polymer gels at least in part inside the human body. In some embodiments, the mixing is performed during delivery to a target site inside a human body, and the biocompatible hydrogel polymer gels at least in part inside the human body. In other embodiments, the mixing is performed outside a human body, and the biocompatible hydrogel polymer gels on the human body. In certain embodiments, the mixing is performed outside the human body, and the biocompatible hydrogel polymer gels at least in part on the human body. In some embodiments, the mixing is performed during delivery to a target site inside a human body, and the biocompatible hydrogel polymer gels at least in part on the human body. In certain embodiments, the mixing is performed outside a human body, and the biocompatible hydrogel polymer gels outside the human body before delivery to a target site.

In some embodiments, the therapeutic agent is a pharmaceutically active biomolecule. In certain embodiments, the pharmaceutically active biomolecule is a protein, peptide, or enzyme. In some embodiments, the pharmaceutically active biomolecule is a monoclonal antibody. In certain embodiments, the pharmaceutically active biomolecule is a vaccine.

In certain embodiments, the nucleophilic group is a thiol or amino group. In some embodiments, the first compound is a glycol, trimethylolpropane, pentaerythritol, hexaglycerol, or tripentaerythritol derivative. In certain embodiments, the first compound further comprises one or more polyethylene glycol sections. In some embodiments, the first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, ethoxylated trimethylolpropane tri-3-mercaptopropionate, ethoxylated hexaglycerol amino acetate.

In some embodiments, the electrophilic group is an epoxide, N-succinimidyl succinate, N-succinimidyl glutarate, N-succinimidyl succinamide, or N-succinimidyl glutaramide. In certain embodiments, the second compound is a trimethylolpropane, glycerol, digylcerol, pentaerythritol, sorbitol, hexaglycerol, tripentaerythritol, or polyglycerol derivative. In some embodiments, the second compound further comprises one or more polyethylene glycol sections. In certain embodiments, the second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, ethoxylated hexaglycerol succinimidyl glutaramide, and sorbitol polyglycidyl ether. In some embodiments, the molecular weight of the first compound and the second compound is between about 1000 and 40000. In certain embodiments, the first compound is waters soluble. In some embodiments the second compound is water soluble.

In some embodiments, the gelling time of the biocompatible hydrogel polymer is controlled by the pH of the aqueous buffer. In certain embodiments, the gelling time is between about 20 seconds and 10 minutes. In some embodiments, the biocompatible hydrogel polymer gels at a target site. In certain embodiments, the biocompatible hydrogel polymer gels at a predetermined time. In some embodiments, the biocompatible hydrogel polymer is a bioabsorbable polymer. In certain embodiments, the biocompatible hydrogel polymer is bioabsorbed within about 1 to 70 days. In some embodiments, the biocompatible hydrogel polymer is substantially non-bioabsorbable. In certain embodiments, the biocompatible hydrogel polymer further comprises a radiopaque material or a pharmaceutically acceptable dye.

In some embodiments, the therapeutic agent is released from the biocompatible hydrogel polymer through diffusion, osmosis, degradation of the biocompatible hydrogel polymer, or any combination thereof. In certain embodiments, the therapeutic agent is initially released from the biocompatible hydrogel polymer through diffusion and later released through degradation of the biocompatible hydrogel polymer. In some embodiments, the therapeutic agent is substantially released from the biocompatible hydrogel polymer within 180 days. In certain embodiments, the therapeutic agent is substantially released from the biocompatible hydrogel polymer within 24 hours. In some embodiments, the first compound and the second compound do not react with the therapeutic agent during formation of the biocompatible hydrogel polymer. In certain embodiments, the biocompatible hydrogel polymer interacts with the therapeutic agent, and wherein more than 10% of the therapeutic agent is released through degradation of the biocompatible hydrogel polymer.

In certain embodiments, the release of the therapeutic agent is determined by the composition of the biocompatible hydrogel polymer. In some embodiments, the therapeutic agent is released while the biocompatible hydrogel polymer degrades. In certain embodiments, the release of the therapeutic agent is essentially inhibited until a time that the biocompatible hydrogel polymer starts to degrade. In some embodiments, the biocompatible hydrogel polymer has a pore size, wherein the pore size is small enough to essentially inhibit the release of the therapeutic agent before the time that the biocompatible hydrogel polymer starts to degrade. In certain embodiments, the ratio of the pore size of the biocompatible hydrogel polymer to the size of the therapeutic agent is less than 8. In some embodiments, at least a portion of the therapeutic agent is released before the time that the biocompatible hydrogel polymer starts to degrade. In certain embodiments, the biocompatible hydrogel polymer has a pore size, wherein the pore size is large enough to allow at least a partial release of the therapeutic agent before the time that the biocompatible hydrogel polymer starts to degrade. In some embodiments, the ratio of the pore size of the biocompatible hydrogel polymer to the size of the therapeutic agent is more than 8 and less than 12. In certain embodiments, the time the biocompatible hydrogel polymer starts to degrade is longer the higher a degree of cross-linking of the biocompatible hydrogel polymer. In some embodiments, the time the biocompatible hydrogel polymer starts to degrade is shorter the higher a concentration of ester groups in the first or second compound.

In a further aspect provided herein is a biocompatible hydrogel polymer comprising (a) at least one first monomeric unit bound through at least one amide, thioester, or thioether linkage to at least one second monomeric unit, (b) at least one second monomeric unit bound to at least one first monomeric unit; and (c) one or more therapeutic agents, wherein the biocompatible hydrogel polymer releases the therapeutic agent at least in part at a target site of a human body.

In some embodiments, the therapeutic agent is a pharmaceutically active biomolecule. In certain embodiments, the pharmaceutically active biomolecule is a protein, enzyme, or peptide. In some embodiments, the pharmaceutically active biomolecule is an antibody. In certain embodiments, the pharmaceutically active biomolecule is a vaccine. In some embodiments, the pharmaceutically active biomolecule is an oligonucleotide.

In some embodiments, the first monomeric unit is a glycol, trimethylolpropane, pentaerythritol, hexaglycerol, or tripentaerythritol derivative. In certain embodiments, the first monomeric unit further comprises one or more polyethylene glycol sections. In some embodiments, the second monomeric unit is a trimethylolpropane, glycerol, digylcerol, pentaerythritol, sorbitol, hexaglycerol, tripentaerythritol, or polyglycerol derivative. In certain embodiments, the second monomeric unit comprises one or more polyethylene glycol sections. In some embodiments, the molecular weight of the first monomeric unit and the second monomeric unit is between about 1000 and 40000.

In some embodiments, the biocompatible hydrogel polymer gels at the target site. In certain embodiments, the biocompatible hydrogel polymer gels at a predetermined time. In some embodiments, the biocompatible hydrogel polymer is a bioabsorbable polymer. In certain embodiments, the biocompatible hydrogel polymer is bioabsorbed within about 1 to 70 days. In some embodiments, the biocompatible hydrogel polymer is substantially non-bioabsorbable. In certain embodiments, the biocompatible hydrogel polymer further comprises a radiopaque material or a pharmaceutically acceptable dye.

In some embodiments, the therapeutic agent is released from the biocompatible hydrogel polymer through diffusion, osmosis, degradation of the biocompatible hydrogel polymer, or any combination thereof. In certain embodiments, the therapeutic agent is initially released from the biocompatible hydrogel polymer through diffusion and later released through degradation of the biocompatible hydrogel polymer. In some embodiments, the therapeutic agent is substantially released from the biocompatible hydrogel polymer within 180 days. In certain embodiments, the therapeutic agent is substantially released from the biocompatible hydrogel polymer within 24 hours.

In certain embodiments, the release of the therapeutic agent is determined by the composition of the biocompatible hydrogel polymer. In some embodiments, the therapeutic agent is released while the biocompatible hydrogel polymer degrades. In certain embodiments, the release of the therapeutic agent is essentially inhibited until a time that the biocompatible hydrogel polymer starts to degrade. In some embodiments, the biocompatible hydrogel polymer has a pore size, wherein the pore size is small enough to essentially inhibit the release of the therapeutic agent before the time that the biocompatible hydrogel polymer starts to degrade. In certain embodiments, the ratio of the pore size of the biocompatible hydrogel polymer to the size of the therapeutic agent is less than 8. In some embodiments, at least a portion of the therapeutic agent is released before the time that the biocompatible hydrogel polymer starts to degrade. In certain embodiments, the biocompatible hydrogel polymer has a pore size, wherein the pore size is large enough to allow at least a partial release of the therapeutic agent before the time that the biocompatible hydrogel polymer starts to degrade. In some embodiments, the ratio of the pore size of the biocompatible hydrogel polymer to the size of the therapeutic agent is more than 8 and less than 12. In certain embodiments, the time the biocompatible hydrogel polymer starts to degrade is longer the higher a degree of cross-linking of the biocompatible hydrogel polymer. In some embodiments, the time the biocompatible hydrogel polymer starts to degrade is shorter the higher a concentration of ester groups in the first or second compound.

In an additional aspect provided herein is a kit comprising (a) at least one first compound comprising more than one nucleophilic group, and one or more therapeutic agent in an aqueous buffer, and (b) at least one second compound comprising more than one electrophilic group, wherein a biocompatible hydrogel polymer is formed following mixing the first compound and the second compound in the aqueous buffer.

In a further aspect provided herein is a kit comprising (a) at least one first compound comprising more than one electrophilic group, and one or more therapeutic agent in an aqueous buffer, and (b) at least one second compound comprising more than one nucleophilic group, wherein a biocompatible hydrogel polymer is formed following mixing the first compound and the second compound in the aqueous buffer.

In another aspect provided herein is a kit for preparing a in vivo gelling pharmaceutical pre-formulation as described above, comprising (a) a first container with a first amount of the at least one first compound, (b) a second container with a second amount of the at least one second compound, (c) a third container with the aqueous buffer, (d) a mixing vessel, (e) optionally, a fourth container with a third amount of one or more therapeutic agent, (f) optionally, a fifth container with a radiopaque material or a pharmaceutically acceptable dye; and instructions for mixing the materials present in each container in the mixing vessel to produce the biocompatible hydrogel polymer, and instructions for delivering the biocompatible hydrogel polymer to the target site inside the human body.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows the elution profile of a small protein (lysozyme) from an amine-ester hydrogel created from 4ARM-20k-AA and esters of various sizes (resulting in different pore sizes). FIG. 1B shows that the degradation time of the hydrogel polymer may be extended with the addition of the amine 8ARM-20k-NH2.

FIG. 2 shows the elution of a large protein (bovine serum albumin [BSA]) from hydrogel polymers with large and small pore sizes, respectively.

DETAILED DESCRIPTION OF THE INVENTION

Figure 3:
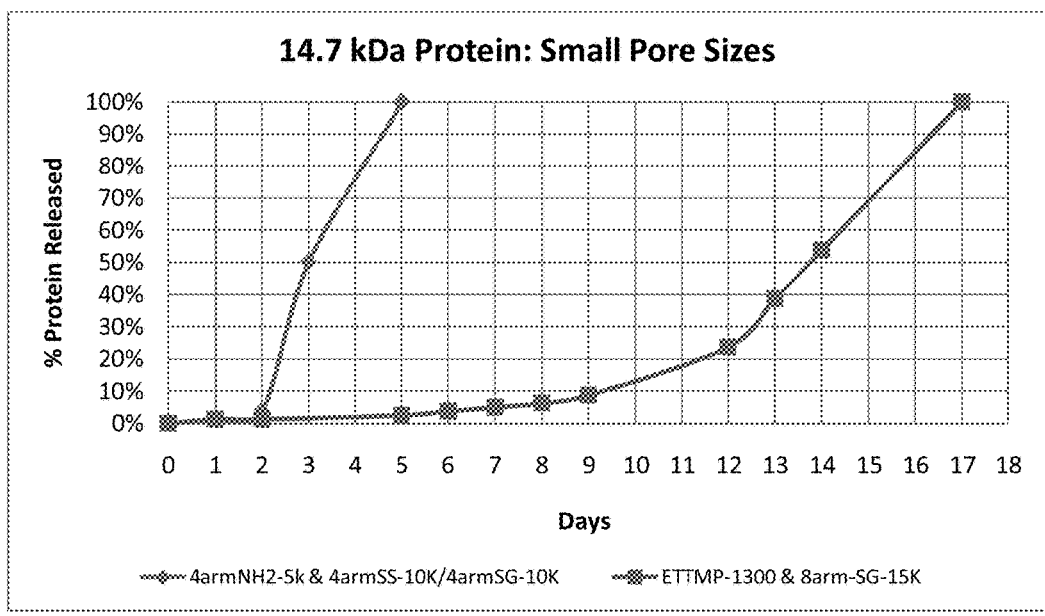
FIG. 3 shows the elution behavior of a small protein (lysozyme) with small pore size formulations (4ARM-5k-NH2 with 4ARM-10k-SS/4ARM-10k-SG; or ETTMP-1300 with 8ARM-15k-SG).

Most pharmaceutical therapeutic agents are administered systemically, exposing many cells in the body to the therapeutic agent in addition to the cells at a target site (e. g, in an organ). Targeted localized drug delivery directly to a target site limits exposure to the therapeutic agents to the areas surrounding the target site. In certain instances, eliminating the introduction agents in the systemic blood stream greatly reduces or completely eliminates the side effects associated with systemic treatments and substantially improves the quality of life and life expectancy of patients. In some instances, treatments are more effective because dosages can be increased with less concern for adverse side effects. In further instances, extended release of the therapeutic agent also reduces the number of doses necessary in the course of treatment. In particular biomolecules are frequently delivered as an injection, which is an inconvenient form of delivery especially if the injection has to be repeated frequently. In some instances, a requirement of frequent injections leads to poor patient compliance. In certain instances, a requirement of frequent injections due to a short half-life of the therapeutic agent (e.g., a biomolecule) leads to the development of resistance.

An in vivo gelling pre-formulation to form a biocompatible hydrogel polymer enables the administration of medication directly to target sites. The polymer starts out as a liquid pre-formulation and is delivered, together with one or more optional therapeutic agents, to the site of a disease using minimally invasive techniques. The initial liquid state allows the polymer/drug combination to be delivered through small catheters directed by endoscopes or other image guided techniques to the site of the disease (e.g., bronchoscope for lung, thoracoscope for the chest cavity, laparoscope for the abdominal cavity, cystoscope for the bladder, arthroscope for joint space, etc.). Once in the body, the liquid pre-formulation polymerizes into a solid hydrogel that in some instances adheres to the tissue and keeps the polymer/drug combination at the site of the disease. In some instances, polymerization and degradation times are controlled by varying the composition of the monomers and buffers allowing for the appropriate application and placement of the hydrogel polymer. In some embodiments, the drug is released in a precise and consistent manner. In certain instances, the biocompatible hydrogel polymer is bioabsorbed over a defined period of time. In some embodiments, the biocompatible hydrogel polymer provides the sustained release of a therapeutic agent at a target site. In certain embodiments, the sustained and controlled release reduces the systemic exposure to the therapeutic agent. The controlled gelling and biodegradation allows the use of the biocompatible hydrogel polymer to deliver one or more therapeutic agents directly to the tissue affected by a disease, thereby minimizing systemic exposure to the therapeutic agent.

In certain instances, local delivery of a therapeutic agent directly to a target using a biocompatible hydrogel polymer achieves the therapeutic effects of the therapeutic agent but without the side effects generally associated with systemic exposure in standard (e.g., oral or parenteral) treatment with the therapeutic agent. In certain embodiments, exposure to the therapeutic agent is limited to the tissue around the target site. In some embodiments, the patient is not exposed systemically to the therapeutic agent. In certain embodiments, a biocompatible hydrogel polymer or in vivo gelling pharmaceutical pre-formulation is used to deliver a therapeutic agent to a target site.

In some instances, the amount of the therapeutic agent, which is delivered to the target site, is increased significantly over standard systemic therapy but with minimal risk of side effects. In some embodiments, the release of therapeutic agents is sustained over longer periods of time than when the therapeutic agent is delivered systemically. In certain embodiments, the local exposure of the tissue at the target site is higher when the therapeutic agent is released from the hydrogel polymer formulation than when the therapeutic agent is delivered systemically. Because the risk of side effects due to the therapeutic agent is reduced, in certain instances, the treatment can be performed in an outpatient department at lower cost than traditional inpatient treatment with systemically delivered chemotherapeutic anticancer agents.

In certain instances, delivery of a therapeutic agent using a biocompatible hydrogel polymer containing the therapeutic agent minimizes the degradation or denaturing of biologically active therapeutic agents. In some instances, the drug is protected from the enzymes and pH conditions of the gastrointestinal tract.

In some instances, the therapeutic agent is released from the biocompatible hydrogel polymer over an extended period of time. In certain instances, delivery of the therapeutic agent in a biocompatible hydrogel polymer provides a depot of the therapeutic agent (e.g., under the skin), wherein the depot releases the therapeutic agent over an extended period of time (e.g., 1 day, 2 days, 3 days, 4 days, 5 days, 6 days, 7 days, 10, days, 14 days, 3 week, 4 week). In some instances, the biocompatible hydrogel polymer releases the therapeutic agent after a delay as a delayed burst.

Exemplary Hydrogel Components

Provided herein are in vivo gelling pharmaceutical pre-formulations, comprising at least one first compound comprising more than one nucleophilic group, at least one second compound comprising more than one electrophilic group, an aqueous buffer in the pH range of about 5.0 to about 9.5, and optionally one or more therapeutic agents. In certain embodiments, the in vivo gelling pharmaceutical pre-formulation forms a biocompatible hydrogel polymer at a target site in a human body by mixing the at least one first compound, the at least one second compound, and the optional therapeutic agent in the aqueous buffer and delivering the mixture to the target site such that the biocompatible hydrogel polymer at least in part polymerizes and/or gels at the target site. In some embodiments, the biocompatible hydrogel polymer is formed following mixing the first compound and the second compound in the aqueous buffer; and wherein the biocompatible hydrogel polymer gels at a target site. In certain embodiments, mixing the first compound, the second compound, and the optional therapeutic agent in the aqueous buffer and delivering the mixture to a target site in the human body generates the in vivo gelling pharmaceutical pre-formulation such that the in vivo gelling pharmaceutical pre-formulation at least in part polymerizes and/or gels at the target site to form a biocompatible hydrogel polymer.

In some embodiments, the first or second compound comprising more than one nucleophilic or electrophilic group are polyol derivatives. In certain embodiments, the first or second compound is a dendritic polyol derivative. In some embodiments, the first or second compound is a glycol, trimethylolpropane, glycerol, digylcerol, pentaerythritiol, sorbitol, hexaglycerol, tripentaerythritol, or polyglycerol derivative. In certain embodiments, the first or second compound is a glycol, trimethylolpropane, pentaerythritol, hexaglycerol, or tripentaerythritol derivative. In some embodiments, the first or second compound is a trimethylolpropane, glycerol, digylcerol, pentaerythritiol, sorbitol, hexaglycerol, tripentaerythritol, or polyglycerol derivative. In some embodiments, the first or second compound is a pentaerythritol, di-pentaerythritol, or tri-pentaerythritol derivative. In certain embodiments, the first or second compound is a hexaglycerol (2-ethyl-2-(hydroxymethyl)-1, 3-propanediol, trimethylolpropane) derivative. In some embodiments, the first or second compound is a sorbitol derivative. In certain embodiments, the first or second compound is a glycol, propyleneglycol, glycerin, diglycerin, or polyglycerin derivative.

In some embodiments, the first and/or second compound further comprises polyethylene glycol (PEG) chains comprising one to 200 ethylene glycol subunits. In certain embodiments, the first and/or second compound further comprises polypropylene glycol (PPG) chains comprising one to 200 propylene glycol subunits. The PEG or PPG chains extending from the polyols are the "arms" linking the polyol core to the nucleophilic or electrophilic groups.

Exemplary Nucleophilic Monomers

The in vivo gelling pharmaceutical pre-formulation comprises at least one first compound comprising more than one nucleophilic group. In some embodiments, the nucleophilic group is a hydroxyl, thiol, or amino group. In preferred embodiments, the nucleophilic group is a thiol or amino group.

In certain embodiments, the nucleophilic group is connected to the polyol derivative through a suitable linker. Suitable linkers include, but are not limited to, esters (e.g., acetates) or ethers. In some instances, monomers comprising ester linkers are more susceptible to biodegradation. Examples of linkers comprising a nucleophilic group include, but are not limited to, mercaptoacetate, aminoacetate (glycin) and other amino acid esters (e.g., alanine, β-alanine, lysine, ornithine), 3-mercaptopropionate, ethylamine ether, or propylamine ether. In some embodiments, the polyol core derivative is bound to a polyethylene glycol or polypropylene glycol subunit, which is connected to the linker comprising the nucleophilic group. The molecular weight of the first compound (the nucleophilic monomer) is about 500 to 40000. In certain embodiments, the molecular weight of a first compound (a nucleophilic monomer) is about 500, about 1000, about 2000, about 3000, about 4000, about 5000, about 6000, about 7000, about 8000, about 9000, about 10000, about 12000, about 15000, about 20000, about 25000, about 30000, about 35000, about 40000, about 50000, about 60000, about 70000, about 80000, about 90000, or about 100000. In some embodiments, the molecular weight of a first compound is about 500 to 2000. In certain embodiments, the molecular weight of a first compound is about 15000 to about 40000. In some embodiments, the first compound is water soluble.

Examples of the construction of monomers comprising more than one nucleophilic group are shown below with a trimethylolpropane or pentaerythritol core polyol. The compounds shown have thiol or amine electrophilic groups that are connected to variable lengths PEG subunit through acetate, propionate or ethyl ether linkers (e.g., structures below of ETTMP (A; n=1), 4ARM-PEG-NH2 (B; n=1), and 4ARM-PEG-AA (C; n=1)). Monomers using other polyol cores are constructed in a similar way.

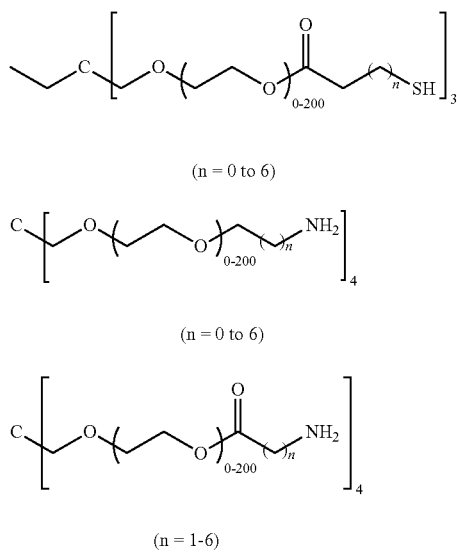

Suitable first compounds comprising a nucleophilic group (used in the amine-ester chemistry) include, but are not limited to, pentaerythritol polyethylene glycol amine (4ARM-PEG-NH2) (molecular weight selected from about 5000 to about 40000, e.g., 5000, 10000, or 20000), pentaerythritol polyethylene glycol amino acetate (4ARM-PEG-AA) (molecular weight selected from about 5000 to about 40000, e.g., 5000, 10000, or 20000), hexaglycerin polyethylene glycol amine (8ARM-PEG-NH2) (molecular weight selected from about 5000 to about 40000, e.g., 10000, 20000, or 40000), or tripentaerythritol glycol amine (8ARM(TP)-PEG-NH2) (molecular weight selected from about 5000 to about 40000, e.g., 10000, 20000, or 40000). Within this class of compounds, 4(or 8)ARM-PEG-AA comprises ester (or acetate) groups while the 4(or 8)ARM-PEG-NH2 monomers do not comprise ester (or acetate) groups.

Other suitable first compounds comprising a nucleophilic group (used in the thiol-ester chemistry) include, but not limited to, glycol dimercaptoacetate (THIOCURE® GDMA), trimethylolpropane trimercaptoacetate (THIOCURE® TMPMA), pentaerythritol tetramercaptoacetate (THIOCURE® PETMA), glycol di-3-mercaptopropionate (THIOCURE® GDMP), trimethylolpropane tri-3-mercaptopropionate (THIOCURE® TMPMP), pentaerythritol tetra-3-mercaptopropionate (THIOCURE® PETMP), polyol-3-mercaptopropionates, polyester-3-mercaptopropionates, propyleneglycol 3-mercaptopropionate (THIOCURE® PPGMP 800), propyleneglycol 3-mercaptopropionate (THIOCURE® PPGMP 2200), ethoxylated trimethylolpropane tri-3-mercaptopropionate (THIOCURE® ETTMP-700), and ethoxylated trimethylolpropane tri-3-mercaptopropionate (THIOCURE® ETTMP-1300).

Exemplary Electrophilic Monomers

The in vivo gelling pharmaceutical pre-formulation comprises at least one first compound comprising more than one electrophilic group. In some embodiments, the electrophilic group is an epoxide, maleimide, succinimidyl, or an alpha-beta unsaturated ester. In preferred embodiments, the electrophilic group is an epoxide or succinimidyl.

In certain embodiments, the electrophilic group is connected to the polyol derivative through a suitable linker. Suitable linkers include, but are not limited to, esters, amides, or ethers. In some instances, monomers comprising ester linkers are more susceptible to biodegradation. Examples of linkers comprising an electrophilic group include, but are not limited to, succinimidyl succinate, succinimidyl glutarate, succinimidyl succinamide, succinimidyl glutaramide, or glycidyl ether. In some embodiments, the polyol core derivative is bound to a polyethylene glycol or polypropylene glycol subunit, which is connected to the linker comprising the electrophilic group. The molecular weight of the second compound (the electrophilic monomer) is about 500 to 40000. In certain embodiments, the molecular weight of a second compound (an electrophilic monomer) is about 500, about 1000, about 2000, about 3000, about 4000, about 5000, about 6000, about 7000, about 8000, about 9000, about 10000, about 12000, about 15000, about 20000, about 25000, about 30000, about 35000, about 40000, about 50000, about 60000, about 70000, about 80000, about 90000, or about 100000. In some embodiments, the molecular weight of a second compound is about 500 to 2000. In certain embodiments, the molecular weight of a second compound is about 15000 to about 40000. In some embodiments, the second compound is water soluble.

Examples of the construction of monomers comprising more than one electrophilic group are shown below with a pentaerythritol core polyol. The compounds shown have a succinimidyl electrophilic group, a glutarate or glutaramide linker, and a variable lengths PEG subunit (e.g., structures below of 4ARM-PEG-SG (D; n=3) and 4ARM-PEG-SGA (E; n=3)). Monomers using other polyol cores or different linkers (e.g., succinate (SS) or succinamide (SSA) are constructed in a similar way.

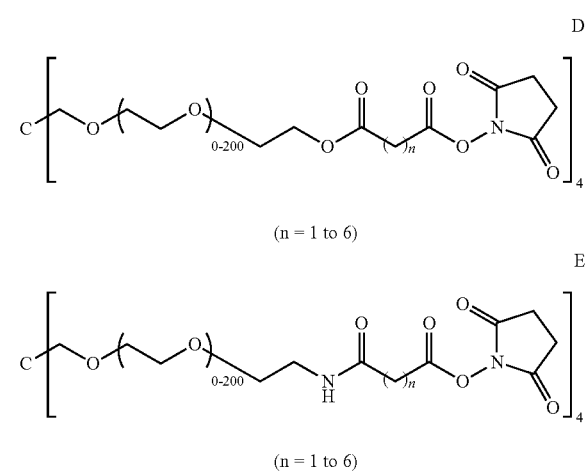

Suitable second compounds comprising an electrophilic group include, but are not limited to, pentaerythritol polyethylene glycol maleimide (4ARM-PEG-MAL) (molecular weight selected from about 5000 to about 40000, e.g., 10000 or 20000), pentaerythritol polyethylene glycol succinimidyl succinate (4ARM-PEG-SS) (molecular weight selected from about 5000 to about 40000, e.g., 10000 or 20000), pentaerythritol polyethylene glycol succinimidyl glutarate (4ARM-PEG-SG) (molecular weight selected from about 5000 to about 40000, e.g., 10000 or 20000), pentaerythritol polyethylene glycol succinimidyl glutaramide (4ARM-PEG-SGA) (molecular weight selected from about 5000 to about 40000, e.g., 10000 or 20000), hexaglycerin polyethylene glycol succinimidyl succinate (8ARM-PEG-SS) (molecular weight selected from about 5000 to about 40000, e.g., 10000 or 20000), hexaglycerin polyethylene glycol succinimidyl glutarate (8ARM-PEG-SG) (molecular weight selected from about 5000 to about 40000, e.g., 10000, 15000, 20000, or 40000), hexaglycerin polyethylene glycol succinimidyl glutaramide (8ARM-PEG-SGA) (molecular weight selected from about 5000 to about 40000, e.g., 10000, 15000, 20000, or 40000), tripentaerythritol polyethylene glycol succinimidyl succinate (8ARM(TP)-PEG-SS) (molecular weight selected from about 5000 to about 40000, e.g., 10000 or 20000), tripentaerythritol polyethylene glycol succinimidyl glutarate (8ARM(TP)-PEG-SG) (molecular weight selected from about 5000 to about 40000, e.g., 10000, 15000, 20000, or 40000), or tripentaerythritol polyethylene glycol succinimidyl glutaramide (8ARM(TP)-PEG-SGA) (molecular weight selected from about 5000 to about 40000, e.g., 10000, 15000, 20000, or 40000). The 4(or 8)ARM-PEG-SG monomers comprise ester groups, while the 4(or 8)ARM-PEG-SGA monomers do not comprise ester groups.

Other suitable second compounds comprising an electrophilic group are sorbitol polyglycidyl ethers, including, but not limited to, sorbitol polyglycidyl ether (DENACOL® EX-611), sorbitol polyglycidyl ether (DENACOL® EX-612), sorbitol polyglycidyl ether (DENACOL® EX-614), sorbitol polyglycidyl ether (DENACOL® EX-614 B), polyglycerol polyglycidyl ether (DENACOL® EX-512), polyglycerol polyglycidyl ether (DENACOL® EX-521), digylcerol polyglycidyl ether (DENACOL® EX-421), glycerol polyglycidyl ether (DENACOL® EX-313), glycerol polyglycidyl ether (DENACOL® EX-313), trimethylolpropane polyglycidyl ether (DENACOL® EX-321), sorbitol polyglycidyl ether (DENACOL® EJ-190).

Formation of Hydrogels

In certain embodiments, the first and second compounds comprising more than one nucleophilic or more than one electrophilic group safely undergo polymerization at a target site inside a mammalian body, for instance on or in an organ, inside a mammalian lung, or inside a joint. In some embodiments, the first compound and the second compound are monomers forming a polymer through the reaction of a nucleophilic group in the first compound with the electrophilic group in the second compound. In certain embodiments, the monomers are polymerized at a predetermined time. In some embodiments, the monomers are polymerized under mild and nearly neutral pH conditions. In certain embodiments, the hydrogel polymer does not change volume after curing.

In some embodiments, the first and second compound react to form amide, thioester, or thioether bonds. When a thiol nucleophile reacts with a succinimidyl electrophile, a thioester is formed. When an amino nucleophile reacts with a succinimidyl electrophile, an amide is formed.

In some embodiments, one or more first compounds comprising an amino group react with one or more second compounds comprising a succinimidyl ester group to form amide linked first and second monomer units. In certain embodiments, one or more first compounds comprising a thiol group react with one or more second compounds comprising a succinimidyl ester group to form thioester linked first and second monomer units. In some embodiments, one or more first compounds comprising an amino group react with one or more second compounds comprising an epoxide group to from amine linked first and second monomer units. In certain embodiments, one or more first compounds comprising a thiol group react with one or more second compounds comprising an epoxide group to form thioether linked first and second monomer units.

In some embodiments, a first compound is mixed with a different first compound before addition to one or more second compounds. In other embodiments, a second compound is mixed with a different second compound before addition to one or more first compounds. In certain embodiments, the properties of the in vivo gelling pharmaceutical pre-formulation and the biocompatible hydrogel polymer are controlled by the properties of the at least one first and at least one second monomer mixture.

In some embodiments, one first compound is used in the biocompatible hydrogel polymer. In certain embodiments, two different first compounds are mixed and used in the biocompatible hydrogel polymer. In some embodiments, three different first compounds are mixed and used in the biocompatible hydrogel polymer. In certain embodiments, four or more different first compounds are mixed and used in the biocompatible hydrogel polymer.

In some embodiments, one second compound is used in the biocompatible hydrogel polymer. In certain embodiments, two different second compounds are mixed and used in the biocompatible hydrogel polymer. In some embodiments, three different second compounds are mixed and used in the biocompatible hydrogel polymer. In certain embodiments, four or more different second compounds are mixed and used in the biocompatible hydrogel polymer.

In some embodiments, a first compound comprising ether linkages to the nucleophilic group are mixed with a different first compound comprising ester linkages to the nucleophilic group. This allows the control of the concentration of ester groups in the resulting biocompatible hydrogel polymer. In certain embodiments, a second compound comprising ester linkages to the electrophilic group are mixed with a different second compound comprising ether linkages to the electrophilic group. In some embodiments, a second compound comprising ester linkages to the electrophilic group are mixed with a different second compound comprising amide linkages to the electrophilic group. In certain embodiments, a second compound comprising amide linkages to the electrophilic group are mixed with a different second compound comprising ether linkages to the electrophilic group.

In some embodiments, a first compound comprising an aminoacetate nucleophile is mixed with a different first compound comprising an ethylamine ether nucleophile at a specified molar ratio (x/y). In certain embodiments, the molar ratio (x/y) is 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. In certain embodiments, the mixture of two first compounds is mixed with one or more second compounds at a molar amount equivalent to the sum of x and y.

In some embodiments, the first compound comprising more than one nucleophilic group and the therapeutic agent are pre-mixed in an aqueous buffer. Once pre-mixing is complete, the second compound comprising more than one electrophilic group is added to the pre-mixture. Shortly after final mixing, the hydrogel polymer is delivered to the target site. In certain embodiments, the optional radiopaque material is added to the pre-mix, the second compound, or to the mixture just before delivery of the hydrogel polymer mixture to the target site.

In other embodiments, the second compound comprising more than one electrophilic group and the therapeutic agent are pre-mixed in an aqueous buffer. Once pre-mixing is complete, the first compound comprising more than one nucleophilic group is added to the pre-mixture. Shortly after final mixing, the hydrogel polymer is delivered to the target site. In certain embodiments, the optional radiopaque material is added to the pre-mix, the first compound, or to the mixture just before delivery of the hydrogel polymer mixture to the target site.

In some embodiments, the first compound comprising more than one nucleophilic group and the second compound comprising more than one electrophilic group are mixed together in an aqueous buffer in the pH range of about 5.0 to about 9.5, whereby a biocompatible hydrogel polymer is formed. In certain embodiments, the first compound comprising more than one nucleophilic group and/or the second compound comprising more than one electrophilic group are individually diluted in an aqueous buffer in the pH range of about 5.0 to about 9.5, wherein the individual dilutions or neat monomers are mixed, whereby a biocompatible hydrogel polymer is formed.

In certain embodiments, the concentration of the monomers in the aqueous is from about 1% to about 100%. In some embodiments, the dilution is used to adjust the viscosity of the monomer dilution. In certain embodiments, the concentration of a monomer in the aqueous buffer is about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the electrophilic and nucleophilic monomers are mixed in such ratio that there is a slight excess of electrophilic groups present in the mixture. In certain embodiments, this excess is about 10%, about 5%, about 2%, about 1%, about 0.9%, about 0.8%, about 0.7%, about 0.6%, about 0.5%, about 0.4%, about 0.3%, about 0.2%, about 0.1%, or less than 0.1%.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation. In certain embodiments, temperature influences the gelling time of the in vivo gelling pharmaceutical pre-formulation. In some embodiments, the type of aqueous buffer influences the gelling time of the in vivo gelling pharmaceutical pre-formulation. In certain embodiments, the concentration of the aqueous buffer influences the gelling time of the in vivo gelling pharmaceutical pre-formulation. In some embodiments, the nucleophilicity and/or electrophilicity of the nucleophilic and electrophilic groups of the monomers influences the gelling time of the in vivo gelling pharmaceutical pre-formulation.

In some embodiments, the gelling time or curing time of the biocompatible hydrogel polymer is controlled by the pH of the aqueous buffer. In certain embodiments, the gelling time is between about 20 seconds and 10 minutes. In some embodiments, the gelling time is less than 30 minutes, less than 20 minutes, less than 10 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.4 minutes, less than 1.2 minutes, less than 1.0 minutes, less than 0.8 minutes, less than 0.6 minutes, or less than 0.4 minutes. In certain embodiments, the pH of the aqueous buffer is from about 5 to about 9.5. In some embodiments, the pH of the aqueous buffer is from about 7.0 to about 9.5. In specific embodiments, the pH of the aqueous buffer is about 8. In some embodiments, the pH of the aqueous buffer is about 5, about 5.5, about 6.0, about 6.5, about 6.6, about 6.7, about 6.8, about 6.9, about 7.0, about 7.1, about 7.2, about 7.3, about 7.4, about 7.5, about 7.6, about 7.8, about 7.9, about 8.0, about 8.1 about 8.2 about 8.3, about 8.4, about 8.5, about 9.0, or about 9.5.

In certain embodiments, the gelling time or curing time of the biocompatible hydrogel polymer is controlled by the type of aqueous buffer. In some embodiments, the aqueous buffer is a physiologically acceptable buffer. In certain embodiments, aqueous buffers include, but are not limited to, aqueous saline solutions, phosphate buffered saline, borate buffered saline, a combination of borate and phosphate buffers wherein each component is dissolved in separate buffers, N-2-Hydroxyethylpiperazine-N'-2-hydroxypropanesulfonic acid (HEPES), 3-(N-Morpholino)propanesulfonic acid (MOPS), 2-([2-Hydroxy-1,1-bis(hydroxymethyl)ethyl]amino)ethanesulfonic acid (TES), 3-[N-tris(Hydroxy-methyl)ethylamino]-2-hydroxyethyl]-1-piperazinepropanesulfonic acid (EPPS), Tris[hydroxymethyl]-aminomethane (THAM), and Tris[hydroxymethyl]methyl aminomethane (TRIS). In some embodiments, the thiol-ester chemistry (e.g., ETTMP nucleophile with SGA or SG electrophile) is performed in borate buffer. In certain embodiments, the amine-ester chemistry (NH2 or AA nucleophile with SGA or SG electrophile) is performed in phosphate buffer.

In certain embodiments, the first compound and the second compound do not react with the therapeutic agent during formation of the biocompatible hydrogel polymer. In some embodiments, the therapeutic agent remains unchanged after polymerization of the first and second compounds (i.e., monomers). In certain embodiments, the therapeutic agent does not change the properties of the hydrogel polymer. In some embodiments, the physiochemical properties of the therapeutic agent and the hydrogel polymer formulation are not affected by the polymerization of the monomers.

In some embodiments, the hydrogel polymer formulations further comprise a contrast agent for visualizing the hydrogel polymer formulation and locating a tumor using e.g., X-ray, fluoroscopy, or computed tomography (CT) imaging. In certain embodiments, the contrast agent enables the visualization of the bioabsorption of the biocompatible hydrogel polymer. In some embodiments, the contrast agent is a radiopaque material. In certain embodiments, the radiopaque material is selected from, but not limited to, sodium iodide, potassium iodide, and barium sulfate, VISI-PAQUE®, OMNIPAQUE®, or HYPAQUE®, tantalum, and similar commercially available compounds, or combinations thereof. In other embodiments, the biocompatible hydrogel polymer further comprises a pharmaceutically acceptable dye.

Area of for Treatment—Target Sites

In certain embodiments, the target site is inside a mammal. In some embodiments, the target site is inside a human being. In certain embodiments, the target site is on the human body. In some embodiments, the target site is accessible through surgery. In certain embodiments, the target site is accessible through minimally invasive surgery. In some embodiments, the target site is accessible through an endoscopic device. In certain embodiments, the target site is in or on a lung, in a joint, in the abdomen, in the ovary, bladder, intestine, or blood vessel.

In other embodiments, an in vivo gelling pharmaceutical pre-formulation or a biocompatible hydrogel polymer is used as a sealant or adhesive with or without a therapeutic agent. In certain embodiments, the in vivo gelling pharmaceutical pre-formulation or biocompatible hydrogel polymer is used to seal fistulas in organs inside the human body. In other embodiments, the in vivo gelling pharmaceutical pre-formulation or biocompatible hydrogel polymer is used to fill cavities in the human body.

In some embodiments, the hydrogel polymer formulation is polymerized ex vivo. In certain embodiments, the ex vivo polymerized hydrogel polymer formulation comprising a therapeutic agent is delivered through traditional routes of administration (e.g., oral, implantation, or rectal).

Delivery of the Hydrogel Formulation to a Target Site

In some embodiments, the in vivo gelling pharmaceutical pre-formulation is delivered as an in vivo gelling pharmaceutical pre-formulation to a target site through a catheter or a needle to form a biocompatible hydrogel polymer at the target site. In certain embodiments, the needle or catheter is attached or part of a delivery device. In some embodiments, the in vivo gelling pharmaceutical pre-formulation containing an optional therapeutic agent is delivered to a target site and deposited on tissue at the target site. In certain embodiments, the in vivo gelling pharmaceutical pre-formulation containing an optional therapeutic agent is delivered to the site of the tumor through a catheter and sprayed onto the target tissue as a thin film using e.g. a nozzle attachment. In some embodiments, the biocompatible hydrogel polymer is directly injected into tissue at the target site.

In certain embodiments, delivery of the in vivo gelling pharmaceutical pre-formulation to the target site is minimally invasive. In some embodiments, the delivery of the in vivo gelling pharmaceutical pre-formulation to the target site in the body of a subject is image guided, using, for example, X-ray, fluoroscopy, computerized tomography (CT), magnetic resonance imaging (MRI), ultrasound (US), positron emission tomography (PET), single photon emission computed tomography (SPECT), or multimodal imaging methods. In some embodiments, the in vivo gelling pharmaceutical pre-formulation further comprises a contrast agent for visualizing the hydrogel formulation and locating a target site using e.g., X-ray, fluoroscopy, or computed tomography (CT) imaging. In certain embodiments, the contrast agent is radiopaque.

In other embodiments, the in vivo gelling pharmaceutical pre-formulation is delivered to the target site in the body using a catheter attached or integrated into an endoscopic delivery device employing fiber-optics for visualization like, for example, a bronchoscope, pleurascope, or thoracoscope. In some embodiments, a delivery device is used to deliver the in vivo gelling pharmaceutical pre-formulation to the target site. In certain embodiments, the delivery device is an endoscopic device. In some embodiments, the endoscopic device is a bronchoscope. In certain embodiments, the bronchoscope is navigated to a tumor location in the lung of a mammal. In some embodiments, the in vivo gelling pharmaceutical pre-formulation containing the therapeutic agent is delivered through a catheter attached to the bronchoscope or other endoscopic delivery device. In some embodiments, the catheter has an outer diameter of about 4 mm, about 3.8 mm, about 3.6 mm, about 3.4 mm, about 3.2 mm, about 3.0 mm, about 2.8 mm, about 2.6 mm, about 2.4 mm, about 2.2 mm, about 2.0 mm, about 1.8 mm, about 1.6 mm, about 1.4 mm, about 1.2 mm, about 1.0 mm, about 0.8 mm, or about 0.6 mm. In preferred embodiments, the catheter has an outer diameter of about 1.2 mm. In certain embodiments, the viscosity of the in vivo gelling pharmaceutical pre-formulation is close to the viscosity of water when delivering the mixture to the site of the tumor through the catheter. In some embodiments, the in vivo gelling pharmaceutical pre-formulation forming the biocompatible hydrogel further comprises a pharmaceutically acceptable dye for visualizing the hydrogel pre-formulation and locating it at a target site using an endoscopic technique.

In certain embodiments, between 10 and 30 mL of the in vivo gelling pharmaceutical pre-formulation optionally comprising a therapeutic agent is delivered to a target site. In some embodiments, about 120 mL, about 110 mL, about 100 mL, about 90 mL, about 80 mL, about 75 mL, about 70 mL, about 65 mL, about 60 mL, about 55 mL, about 50 mL, about 45 mL, about 40 mL, about 35 mL, about 30 mL, about 25 mL, about 20 mL, about 15 mL, about 10 mL, about 5 mL, about 2 mL, or about 1 mL in vivo gelling pharmaceutical pre-formulation optionally comprising a therapeutic agent is delivered to a target site. In certain embodiments, less than 120 mL, less than 110 mL, less than 100 mL, less than 90 mL, less than 80 mL, less than 75 mL, less than 70 mL, less than 65 mL, less than 60 mL, less than 55 mL, less than 50 mL, less than 45 mL, less than 40 mL, less than 35 mL, less than 30 mL, less than 25 mL, less than 20 mL, less than 15 mL, less than 10 mL, less than 5 mL, less than 2 mL, or less than 1 mL in vivo gelling pharmaceutical pre-formulation optionally comprising a therapeutic agent is delivered to a target site. In some embodiments, more than 120 mL, more than 110 mL, more than 100 mL, more than 90 mL, more than 80 mL, more than 75 mL, more than 70 mL, more than 65 mL, more than 60 mL, more than 55 mL, more than 50 mL, more than 45 mL, more than 40 mL, more than 35 mL, more than 30 mL, more than 25 mL, more than 20 mL, more than 15 mL, more than 10 mL, more than 5 mL, more than 2 mL, or more than 1 mL in vivo gelling pharmaceutical pre-formulation optionally comprising a therapeutic agent is delivered to a target site. In certain embodiments, about 5 to 50 mL in vivo gelling pharmaceutical pre-formulation optionally comprising a therapeutic agent is delivered to a target site.

In some embodiments, the gelling time of the biocompatible hydrogel polymer is set according to the preference of the doctor delivering the hydrogel polymer mixture to a target site. In most instances, a physician delivers the hydrogel polymer mixture to the target within 15 to 30 seconds. In some embodiments, the hydrogel polymer mixture gels after delivery at the target site, covering the target site.

In some embodiments, the gelling time or curing time of the biocompatible hydrogel polymer is controlled by the pH of the aqueous buffer. In certain embodiments, the gelling time is between about 20 seconds and 10 minutes. In preferred embodiments, the gelling time is about 90 seconds.

In some embodiments, the gelling time is less than 120 minutes, less than 90 minutes, less than 60 minutes, less than 50 minutes, less than 40 minutes, less than 30 minutes, less than 20 minutes, less than 10 minutes, less than 9 minutes, less than 8 minutes, less than 7 minutes, less than 6 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.5 minutes, less than 1.4 minutes, less than 1.2 minutes, less than 1.0 minutes, less than 0.8 minutes, less than 0.6 minutes, or less than 0.4 minutes. In certain embodiments, the gelling time is more than 120 minutes, more than 90 minutes, more than 60 minutes, more than 50 minutes, more than 40 minutes, more than 30 minutes, more than 20 minutes, more than 10 minutes, more than 9 minutes, more than 8 minutes, more than 7 minutes, more than 6 minutes, more than 5 minutes, more than 4.8 minutes, more than 4.6 minutes, more than 4.4 minutes, more than 4.2 minutes, more than 4.0 minutes, more than 3.8 minutes, more than 3.6 minutes, more than 3.4 minutes, more than 3.2 minutes, more than 3.0 minutes, more than 2.8 minutes, more than 2.6 minutes, more than 2.4 minutes, more than 2.2 minutes, more than 2.0 minutes, more than 1.8 minutes, more than 1.6 minutes, more than 1.5 minutes, more than 1.4 minutes, more than 1.2 minutes, more than 1.0 minutes, more than 0.8 minutes, more than 0.6 minutes, or more than 0.4 minutes. In some embodiments, the gelling time is about 120 minutes, about 90 minutes, about 60 minutes, about 50 minutes, about 40 minutes, about 30 minutes, about 20 minutes, about 10 minutes, about 9 minutes, about 8 minutes, about 7 minutes, about 6 minutes, about 5 minutes, about 4.8 minutes, about 4.6 minutes, about 4.4 minutes, about 4.2 minutes, about 4.0 minutes, about 3.8 minutes, about 3.6 minutes, about 3.4 minutes, about 3.2 minutes, about 3.0 minutes, about 2.8 minutes, about 2.6 minutes, about 2.4 minutes, about 2.2 minutes, about 2.0 minutes, about 1.8 minutes, about 1.6 minutes, about 1.5 minutes, about 1.4 minutes, about 1.2 minutes, about 1.0 minutes, about 0.8 minutes, about 0.6 minutes, or about 0.4 minutes.

In certain embodiments, the pH of the aqueous buffer is from about 5.0 to about 9.5. In some embodiments, the pH of the aqueous buffer is from about 7.0 to about 9.0. In specific embodiments, the pH of the aqueous buffer is about 8.0. In some embodiments, the pH is about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.9, about 9, about 9.1 about 9.2, about 9.3, about 9.4, or about 9.5.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation.

In some embodiments, curing of the biocompatible hydrogel polymer is verified post-administration. In certain embodiments, the verification is performed in vivo at the delivery site. In other embodiments, the verification is performed ex vivo. In some embodiments, curing of the biocompatible hydrogel polymer is verified visually through the fiber-optics of an endoscopic device. In certain embodiments, curing of biocompatible hydrogel polymers comprising radiopaque materials is verified using X-ray, fluoroscopy, or computed tomography (CT) imaging. A lack of flow of the biocompatible hydrogel polymer indicates that the biocompatible hydrogel polymer has gelled and the hydrogel is sufficiently cured. In further embodiments, curing of the biocompatible hydrogel polymer is verified by evaluation of the residue in the delivery device, for instance the residue in the catheter of the bronchoscope or other endoscopic device, or the residue in the syringe used to deliver the biocompatible hydrogel polymer. In other embodiments, curing of the biocompatible hydrogel polymer is verified by depositing a small sample (e.g., ~1 mL) on a piece of paper or in a small vessel and subsequent evaluation of the flow characteristics after the gelling time has passed.

In some embodiments, the in vivo gelling pharmaceutical pre-formulation optionally comprising one or more therapeutic agents is delivered to the target site so that the pre-formulation mostly covers the target site. In certain embodiments, the in vivo gelling pharmaceutical pre-formulation substantially covers an exposed portion of diseased tissue. In some embodiments, the in vivo gelling pharmaceutical pre-formulation does not spread to any other location intentionally. In some embodiments, the in vivo gelling pharmaceutical pre-formulation substantially covers diseased tissue and does not significantly cover healthy tissue. In certain embodiments, the biocompatible hydrogel polymer does not significantly cover healthy tissue. In some embodiments, in vivo gelling pharmaceutical pre-formulation gels over the target site and thoroughly covers diseased tissue. In some embodiments, the biocompatible hydrogel polymer adheres to tissue.

Bioabsorbance of the Hydrogel

In some embodiments, the biocompatible hydrogel polymer is a bioabsorbable polymer. In certain embodiments, the biocompatible hydrogel polymer is bioabsorbed within about 5 to 30 days. In some embodiments, the biocompatible hydrogel polymer is bioabsorbed within about 30 to 180 days. In preferred embodiments, the biocompatible hydrogel polymer is bioabsorbed within about 1 to 70 days. In some embodiments the biocompatible hydrogel polymer is bioabsorbed within about 365 days, 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, or about 1 day. In certain embodiments the biocompatible hydrogel polymer is bioabsorbed within less than 365 days, 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, or less than 1 day. In some embodiments the biocompatible hydrogel polymer is bioabsorbed within more than 365 days, 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, or more than 1 day. In some embodiments, the biocompatible hydrogel polymer is substantially non-bioabsorbable.

The biocompatible hydrogel polymer is slowly bioabsorbed, dissolved, and or excreted. In some instances, the rate of bioabsorption is controlled by the number of ester groups in the biocompatible and/or biodegradable hydrogel polymer. In other instances, the higher the concentration of ester units is in the biocompatible hydrogel polymer, the longer is its lifetime in the body. In further instances, the electron density at the carbonyl of the ester unit controls the lifetime of the hydrogel polymer in the body. In certain instances, biocompatible hydrogel polymers without ester groups are essentially not biodegradable. In additional instances, the molecular weight of the first and second compounds controls the lifetime of the hydrogel polymer in the body. In further instances, the number of ester groups per gram of polymer controls the lifetime of the hydrogel polymer in the body.

In some instances, the lifetime of the hydrogel polymer can be estimated using a model, which controls the temperature and pH at physiological levels while exposing the hydrogel polymer to a buffer solution. In certain instances, the biodegradation of the hydrogel polymer is substantially non-enzymatic degradation.

In some embodiments, the selection of reaction conditions determines the degradation time of the hydrogel polymer. In certain embodiments, the concentration of the first compound and second compound monomers determines the degradation time of the resulting hydrogel polymer. In some instances, a higher monomer concentration leads to a higher degree of cross-linking in the resulting hydrogel polymer. In certain instances, more cross-linking leads to a later degradation of the hydrogel polymer.

In certain embodiments, the composition of the linker in the first and/or second compound influences the speed of degradation of the resulting hydrogel polymer. In some embodiments, the more ester groups are present in the hydrogel polymer, the faster the degradation of the hydrogel polymer. In certain embodiments, the higher the concentration of mercaptopropionate (ETTMP), acetate amine (AA), glutarate or succinate (SG or SS) monomers, the faster the rate of degradation.

Control of Release Rate of a Therapeutic Agent

In some embodiments, the biocompatible hydrogel polymer slowly delivers a therapeutic agent to a target site by diffusion and/or osmosis over time ranging from hours to days. In certain embodiments, the drug is delivered directly to the target site. In some embodiments, the procedure of delivering a biocompatible hydrogel polymer comprising a therapeutic agent to a target site is repeated several times, if needed. In other embodiments, the therapeutic agent is released from the biocompatible hydrogel polymer through biodegradation of the hydrogel polymer. In some embodiments, the therapeutic agent is released through a combination of diffusion, osmosis, and/or hydrogel degradation mechanisms. In certain embodiments, the release profile of the therapeutic agent from the hydrogel polymer is unimodal. In some embodiments, the release profile of the therapeutic agent from the hydrogel polymer is bimodal. In certain embodiments, the release profile of the therapeutic agent from the hydrogel polymer is multimodal.

In some embodiments, the therapeutic agent is released from the biocompatible hydrogel polymer though diffusion or osmosis. In certain embodiments, the therapeutic agent is substantially released from the biocompatible hydrogel polymer within 180 days. In some embodiments, the therapeutic agent is substantially released from the biocompatible hydrogel polymer within 14 days. In certain embodiments, the therapeutic agent is substantially released from the biocompatible hydrogel polymer within 24 hours. In some embodiments, the therapeutic agent is substantially released from the biocompatible hydrogel polymer within one hour. In certain embodiments, the therapeutic agent is substantially released from the biocompatible hydrogel polymer within about 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, about 1 day, about 0.5 day, about 6 hours, about 4 hours, about 2 hours, about or 1 hour. In some embodiments, the therapeutic agent is substantially released from the biocompatible hydrogel polymer within more than 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, more than 1 day, more than 0.5 day, more than 6 hours, more than 4 hours, more than 2 hours, more than or 1 hour. In certain embodiments, the therapeutic agent is substantially released from the biocompatible hydrogel polymer within less than 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, less than 1 day, less than 0.5 day, less than 6 hours, less than 4 hours, less than 2 hours, less than or 1 hour. In some embodiments, the therapeutic agent is substantially released from the biocompatible hydrogel polymer within about one day to about fourteen days. In certain embodiments, the therapeutic agent is substantially released from the biocompatible hydrogel polymer within about one day to about 70 days.

In some embodiments, the therapeutic agent is a biomolecule and the release of the biomolecule from the hydrogel polymer is controlled by the composition of the hydrogel polymer. In certain embodiments, the biomolecule is released when the hydrogel polymer starts to degrade. In some embodiments, the pore size of the hydrogel polymer is small enough to prevent the early phase release of the biomolecule (i.e., release before the degradation of the hydrogel polymer). In certain embodiments, the pore size of the hydrogel polymer is large enough to allow the early phase release of the biomolecule. In some embodiments, the ratio of the pore size of the hydrogel polymer to the size of the biomolecule determines the release rate of the biomolecule.

In certain embodiments, the pore size of the hydrogel polymer controls the rate of elution of a therapeutic agent (e.g., a biomolecule). In some instances, the larger the pore size of the hydrogel polymer, the higher is the elution rate of the therapeutic agent from the hydrogel polymer. In some embodiments, large biomolecules (e.g., proteins) do not elute from a hydrogel polymer with small pore sizes until degradation of the polymer starts. In certain embodiments, small biomolecules (e.g., small proteins or peptide) do not elute from a hydrogel polymer with very small pore sizes until the degradation of the hydrogel sets in.

In some embodiments, the pore diameters are estimated from the molecular weight per arm of the combined components. The pore diameter is calculated based on the number of PEG units per arm and a carbon-carbon-carbon bond length of 0.252 nm with a 110° bond angle. This assumes a fully extended chain that accounts for bonding angles and complete reactivity of all functional end groups to form the pore network. The pore diameter was further modified by a correlation relating the pore size to the inverse of the hydrogel swelling ratio:

$$\xi \approx L*(V_p/V_s)^{-1/3} \quad \text{(Equation 1)}$$

where $V_p$ is the volume of polymer, $V_s$ is the volume of the swollen gel, L is the calculated pore diameter, and $\xi$ is the swollen pore diameter. Based on equilibrium swelling experiments, the ratio of $V_p$ to $V_s$ is estimated to be around 0.5 (also see EXAMPLE 14).

For instance, the results of pore size estimation are shown in Table 7 along with the values of the physical parameters used. In some embodiments, the pore size of the biocompatible hydrogel polymer is in the range of about 10 nm to about 100 nm. In certain embodiments, the pore diameter of a biocompatible hydrogel polymer is about 500 nm, about 400 nm, about 300 nm, about 250 nm, about 200 nm, about 150 nm, about 100 nm, about 90 nm, about 80 nm, about 70 nm, about 60 nm, about 50 nm, about 40 nm, about 30 nm, about 25 nm, about 20 nm, about 15 nm, about 10 nm, about 5 nm, or about 2 nm. In some embodiments, the pore diameter of a biocompatible hydrogel polymer is less than 500 nm, less than 400 nm, less than 300 nm, less than 250 nm, less than 200 nm, less than 150 nm, less than 100 nm, less than 90 nm, less than 80 nm, less than 70 nm, less than 60 nm, less than 50 nm, less than 40 nm, less than 30 nm, less than 25 nm, less than 20 nm, less than 15 nm, less than 10 nm, less than 5 nm, or less than 2 nm. In certain embodiments, the pore diameter of a biocompatible hydrogel polymer is more than 500 nm, more than 400 nm, more than 300 nm, more than 250 nm, more than 200 nm, more than 150 nm, more than 100 nm, more than 90 nm, more than 80 nm, more than 70 nm, more than 60 nm, more than 50 nm, more than 40 nm, more than 30 nm, more than 25 nm, more than 20 nm, more than 15 nm, more than 10 nm, more than 5 nm, or more than 2 nm. In some embodiments, the pore diameter is more than 10 nm and less than 100 nm.

In certain embodiments, the elution of the therapeutic agent (e.g., a biomolecule) depends on the ratio of the size pore and the therapeutic agent (e.g., a biomolecule). In some embodiments, significant elution of the therapeutic agent (e.g., a biomolecule) starts at a pore diameter to therapeutic agent size ratio of about 8. In certain embodiments, significant elution of the therapeutic agent (e.g., a biomolecule) starts at a pore diameter to therapeutic agent size ratio of greater than 5, greater than 6, greater than 7, greater than 8, greater than 9, or greater than 10. In some embodiments, no significant elution of the therapeutic agent occurs at a pore diameter to therapeutic agent size ratio of less than 20, less than 15, less than 14, less than 13, less than 12, less than 11, less than 10, less than 9, less than 8, less the 7, less than 6, less than 5, less than 4, less than 3, or less than 2. In preferred embodiments, significant elution of the therapeutic agent occurs at pore diameter to therapeutic agent size ratio of more than 8 and less than 12. In some embodiments, the elution rate per day of a therapeutic agent is higher with a hydrogel polymer with larger pore sizes compared to a hydrogel polymer with a smaller pore size.

In some embodiments, large PEG groups in the monomers leads to large pore sizes in the resulting hydrogel polymer allowing the elution of large biomolecules. In certain embodiments, large molecular weights of the monomers lead to hydrogel polymers with large pore sizes. In some embodiments, large monomer molecular weights of about 40 kDa lead to hydrogel polymers with large pore sizes. In certain embodiments, large monomer molecular weights of about 20 kDa lead to hydrogel polymers with large pore sizes.

In some embodiments, small PEG groups in the monomers leads to small pore sizes in the resulting hydrogel polymer restricting the elution of small (and large) biomolecules. In certain embodiments, small molecular weights of the monomers lead to hydrogel polymers with small pore sizes. In some embodiments, small monomer molecular weights of about 5 kDa lead to hydrogel polymers with small pore sizes. In certain embodiments, small monomer molecular weights of about 10 kDa in an 8-arm monomer lead to hydrogel polymers with small pore sizes. In some embodiments, the small pore sizes restrict the elution of small biomolecules (e.g., peptides of 1-20 kDa).

Target Diseases for Treatment with Biocompatible Hydrogel Polymer

In certain embodiments, the biocompatible hydrogel polymer comprises a therapeutic agent. In some embodiments, the biocompatible hydrogel polymer and in vivo gelling pharmaceutical pre-formulation is used to deliver a therapeutic agent to a target site. In certain embodiments, the target site is the site of a tumor or cancer. In some embodiments, the biocompatible hydrogel polymer comprising a therapeutic agent is used in the treatment of cancers using one or more anticancer agents. In certain embodiments, the cancer is a cancer of the lung (e.g., NSCLC, mesothelioma), ovary, bladder, or colon. In some embodiments, a biocompatible hydrogel polymer comprising a therapeutic agent is used in locoregional control for advanced lung cancer in patients unable to tolerate conventional chemotherapy. In certain embodiments, a biocompatible hydrogel polymer comprising a therapeutic agent is used in neoadjuvant chemotherapy for patients with stage III disease. In some embodiments, a biocompatible hydrogel polymer comprising a therapeutic agent is used in the treatment of solitary lung metastases from other malignancies in patients unable to tolerate surgery. In certain embodiments, a biocompatible hydrogel polymer comprising a therapeutic agent is used as an alternative or adjunct to systemic chemotherapy for locoregional control of lung cancer in patients. In some embodiments, the therapeutic agent is an anticancer agent. In certain embodiments, the therapeutic agent is a chemotherapeutic anticancer agent.

In some embodiments, a biocompatible hydrogel polymer comprising a therapeutic agent is used for the delivery of therapeutic agents to a target site. In certain embodiments, a biocompatible hydrogel polymer comprising a cytotoxin or chemotherapy agent is used for the delivery of the cytotoxin or chemotherapy agent to the site of a mesothelioma or other cancer. In some embodiments, a biocompatible hydrogel polymer comprising a chemotherapy agent is used for the delivery of the chemotherapy agent to the site of an ovarian cancer or peritoneal carcinomatosis. In certain embodiments, a biocompatible hydrogel polymer comprising a chemotherapy agent is used for the delivery of the chemotherapy agent to the site of a bladder cancer. In certain embodiments, a biocompatible hydrogel polymer comprising a chemotherapy agent is used for the delivery of the chemotherapy agent to the site of a colon cancer. In some embodiments, a biocompatible hydrogel polymer comprising anti-inflammatory agents, anesthetics, and/or analgesics is used in the treatment of arthritis (e.g., rheumatoid arthritis or osteoarthritis). In certain embodiments, a biocompatible hydrogel polymer comprising antibiotics is used for the delivery of the antibiotics in the treatment of tuberculosis (e.g., multi-drug resistant tuberculosis). In some embodiments, a biocompatible hydrogel polymer comprising antifungals is used in the treatment of aspergillosis or other localized pulmonary fungal infections. In certain embodiments, a biocompatible hydrogel polymer comprising antibiotics and/or anti-inflammatory agents is used for fistula repair in Crohn's disease and other fistulas in contaminated places. In some embodiments, a biocompatible hydrogel polymer comprising one or more antibiotics is used for the long term release of antibiotics for prosthetic joint infections. In certain embodiments, a biocompatible hydrogel polymer comprising one or more antibiotics is used in antibiotic prophylaxis in abdominal surgery. In some embodiments, a biocompatible hydrogel polymer comprising a hemostasis agent is used to control bleeding (e.g., to control gastrointestinal bleeding or endobronchial bleeding).

In certain embodiments, a biocompatible hydrogel polymer comprising a therapeutic agent is used to deliver the therapeutic agent to a target site. In some embodiments, a biocompatible hydrogel polymer comprising a therapeutic agent is used for controlled delivery of the therapeutic agent to a target site. In certain embodiments, the controlled delivery is for an extended period of time. In other embodiments, the therapeutic agent is released from the hydrogel polymer is a delayed burst. In some embodiments, the burst is delayed by hours, or days, or weeks. In certain embodiments, the therapeutic agent is not stable enough for other forms of delivery.

In some embodiments, the therapeutic agent delivered to the target site is a therapeutic protein or other pharmaceutically active biomolecule. Biomolecules include, but are not limited to, antibodies, monoclonal antibodies, aptamers, (anti-sense) oligonucleotides, oligosaccharides, glycopeptides, enzymes, peptide, proteins, recombinant proteins, hormones, vaccines, or functionalized nanoparticle. In certain embodiments, a biomolecule is a biologically active compound with a molecular weight greater than 1 kDa.

In some embodiments, a biocompatible hydrogel polymer comprising a therapeutic agent is used to reduce the frequency of injections. In certain embodiments, the therapeutic agent is a biomolecule. In some embodiments, biomolecules are delivered using a hydrogel polymer and release over time to reduce to the frequency of injections. In some embodiments, the frequency of injections is thrice, twice or once a week, every 10 days, every 2 weeks, every 3 weeks, every 4 weeks, every 5 weeks, or every 6 weeks.

In certain embodiments, a biocompatible hydrogel polymer comprising a therapeutic agent is used to decrease the likelihood of developing resistance to the therapeutic agent by ensuring sufficient exposure over a prolonged period of time. In some embodiments, the likelihood of HIV developing resistance to antiviral therapeutic agents is decreased by sustained delivery of the therapeutic agent with a biocompatible hydrogel polymer. In certain embodiments, the therapeutic agent is a biomolecule.

In some embodiments, a biocompatible hydrogel polymer comprising a therapeutic agent is used to deliver drugs locally over extended periods of time. In certain embodiments, the therapeutic agent is a biomolecule. In some embodiments, the local deliver reduces the risk of systemic side effects.

Exemplary Anticancer Agents

In some embodiments, the anticancer agent is a chemotherapeutic anticancer agent. In certain embodiments, the biocompatible hydrogel polymer is loaded with a desired amount of one or more chemotherapeutic anticancer agents to form a biocompatible hydrogel chemopolymer. Examples of chemotherapeutic anticancer agents include, but are not limited to, Nitrogen Mustards like bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides like etoglucid; Other Alkylating Agents like dacarbazine, mitobronitol, pipobroman, temozolomide; Folic Acid Analogues like methotrexate, pemetrexed, pralatrexate, raltitrexed; Purine Analogs like cladribine, clofarabine, fludarabine, mercaptopurine, nelarabine, tioguanine; Pyrimidine Analogs like azacitidine, capecitabine, carmofur, cytarabine, decitabine, fluorouracil, gemcitabine, tegafur; Vinca Alkaloids like vinblastine, vincristine, vindesine, vinflunine, vinorelbine; Podophyllotoxin Derivatives like etoposide, teniposide; Colchicine derivatives like demecolcine; Taxanes like docetaxel, paclitaxel, paclitaxel poliglumex; Other Plant Alkaloids and Natural Products like trabectedin; Actinomycines like dactinomycin; Antracyclines like aclarubicin, daunorubicin, doxorubicin, epirubicin, idarubicin, mitoxantrone, pirarubicin, valrubicin, zorubincin; Other Cytotoxic Antibiotics like bleomycin, ixabepilone, mitomycin, plicamycin; Platinum Compounds like carboplatin, cisplatin, oxaliplatin, satraplatin; Methylhydrazines like procarbazine; Sensitizers like aminolevulinic acid, efaproxiral, methyl aminolevulinate, porfimer sodium, temoporfin; Protein Kinase Inhibitors like dasatinib, erlotinib, everolimus, gefitinib, imatinib, lapatinib, nilotinib, pazonanib, sorafenib, sunitinib, temsirolimus; Other Antineoplastic Agents like alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens like diethylstilbenol, ethinylestradiol, fosfestrol, polyestradiol phosphate; Progestogens like gestonorone, medroxyprogesterone, megestrol; Gonadotropin Releasing Hormone Analogs like buserelin, goserelin, leuprorelin, triptorelin; Anti-Estrogens like fulvestrant, tamoxifen, toremifene; Anti-Androgens like bicalutamide, flutamide, nilutamide; Enzyme Inhibitors like aminoglutethimide, anastrozole, exemestane, formestane, letrozole, vorozole; Other Hormone Antagonists like abarelix, degarelix; Immunostimulants like histamine dihydrochloride, mifamurtide, pidotimod, plerixafor, roquinimex, thymopentin; Immunosuppressants like everolimus, gusperimus, leflunomide, mycophenolic acid, sirolimus; Calcineurin Inhibitors like ciclosporin, tacrolimus; Other Immunosuppressants like azathioprine, lenalidomide, methotrexate, thalidomide; and Radiopharmaceuticals like iobenguane.

In preferred embodiments, the chemotherapeutic anticancer agent is selected from, but not limited to, docetaxel, paclitaxel, paclitaxel poliglumex, ixabepilone, carboplatin, cisplatin, oxaliplatin, satraplatin, etoposide, gemcitabine, or pemetrexed.

In some embodiments, the anticancer agent is a toxin, e.g. diphtheria toxin. In certain embodiments, the biocompatible hydrogel polymer is loaded with a therapeutically effective amount of one or more toxins to form a biocompatible hydrogel polymer. Examples of toxins include Exotoxins like diphtheria toxin, botulinium toxin, cytolysins, hemolysins (e.g., α-toxin or α-hemolysin of *Staphyllococcus aureus*), cholera toxin, pertussis toxin, Shiga toxin; Heat-Stable Enterotoxin from *E. coli*; Curare; α-Cobratoxin; Verotoxin-1; and Adenylate Cyclase (AC) toxin from *Bordetella pertussis*.

Exemplary Antifungals

In some embodiments, the biocompatible hydrogel polymer comprises an antifungal agent. In certain embodiments, the antifungal agent is a polyene antifungal, an imidazole, triazole, or thiazole antifungal, a triazole antifungal, a thiazole antifungal, an allylamine derivative, or an echinocandin derivative. Examples of antifungal agents include, but are not limited to, Polyene derivatives like natamycin, rimocidin, filipin, nystatin, amphotericin B, candicin, hamycin; Imidazole derivatives like miconazole, ketoconazole, clotrimazole, econazole, omoconazole, bifonazole, butoconazole, fenticonazole, isoconazole, oxiconazole, sertaconazole, sulconazole, tioconazole; Tetrazole derivatives like fluconazole, itraconazole, isavuconazole, posaconazole, voriconzaole, terconazole, albaconazole; Thiazole derivatives like abafungin; Allylamine derivative like terbifine, naftifine, butenafine; Echinocandin derivatives like anidulafungin, caspofungin, micafungin; Other antifungals like polygodial, benzoic acid, ciclopirox, tonaftate, undecylenic acid, flycytosine, griseofulvin, haloprogin, sodium bicarbonate, pirctone olamine, zinc pyrithione, selenium sulfide, tar, or tea tree oil.

Exemplary Antibiotics

In some embodiments, the biocompatible hydrogel polymer comprises an antibiotic. In certain embodiments, the antibiotic agent is a aminoglycoside, ansamycin, carbacephem, carbapenem, cephalosporin, glycopeptide, lincosamide, lipopeptide, macrolide, monobactam, nitrofurans, penicillin, polypeptide, quinolone, sulfonamide, or tetracycline. Examples of antibiotic agents include, but are not limited to, Aminoglycoside derivatives like amikacin, gentamicin, kanamycin, neomycin, netilmicin, tobramicin, paromomycin; Ansamycin derivatives like geldanamycin, herbimycin; Carbacephem derivatives like loracarbef, Carbapenem derivatives like ertapenem, doripenem, imipenem, meropenem; Cephalosporin derivatives like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; Glycopeptide derivatives like teicoplanin, vancomycin, telavancin; Lincosamides like clindamycin, lincomycin; Lipopeptide derivatives like daptomycin; Macrolide derivatives like azithromycin, clarithromycin, dirithromycin, erythromycin, roxithromycin, troleandomycin; telithreomycin, spectinomycin; Monobactam derivatives like aztreonam; Nitrofuran derivatives like furazolidone, nitrofurantoin; Penicillin derivatives like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; Penicillin combinations like amoxicillin/clavulanate, ampicillin/sulbactam, piperacillin/tazobactam, ticarcillin/clavulanate; Polypeptide derivatives like bacitracin, colistin, polymyxin B; Quinolone derivatives like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; Sulfonamide derivatives like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; Tetracyclin derivatives like demeclocycline, doxycycline, minocycline, oxytetracycline, tetracycline; Derivatives against mycobacteria like clofazimine, dapsone, capreomycin, cycloserine, ethambutol, ethioamide, isoniazid, pyrazinamide, rifampin, refampicin, rifabutin, rifapentine, streptomycin; or other antibiotic agents like arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole.

Exemplary Antiviral Agents

In some embodiments, the biocompatible hydrogel polymer comprises an antiviral agent. In certain embodiments, the antiviral agent is a nucleoside reverse transcriptase inhibitor, a non-nucleoside reverse transcriptase inhibitor, a fusion inhibitor, an integrase inhibitor, a nucleoside analog, a protease inhibitor, a reverse transcriptase inhibitor. Examples of antiviral agents include, but are not limited to, abacavir, aciclovir, acyclovir, adefovir, amantadine, amprenavir, ampligen, arbidol, atazanavir, boceprevir, cidofovir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, interferon, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir (Valtrex), valganciclovir, vicriviroc, vidarabine, viramidine, zalcitabine, zanamivir, zidovudine.

Exemplary Immunosuppressive Agents

In some embodiments, the biocompatible hydrogel polymer comprises an immunosuppressive agent. In certain embodiments, the immunosuppressive agent is a calcinuerin inhibitor, mTor inhibitor, an anti-proliferative agent (e.g., an alkylating agent or an antimetabolite), a glucocorticosteroid, an antibody, or an agent acting on immunophilins. Examples of immunosuppressive agents include, but are not limited to, Calcineurin inhibitors like ciclosporin, tacrolimus; mTOR inhibitors like sirolimus, everolimus; Anti-proliferatives like azathioprine, mycophenolic acid; Corticosteroids like prednisolone, hydrocortisone; Monoclonal anti-IL-2Rα receptor antibodies like basiliximab, daclizumab; Polyclonal anti-T-cell antibodies like anti-thymocyte globulin (ATG), anti-lymphocyte globulin (ALG); Monoclonal anti-CD20 antibodies like rituximab; Interleukin inhibitors like daclizumab, basiliximab, anakinra, rilonacept, ustekinumab, mepolizumab, tocilizumab, canakinumab, briakinumab; Tumor necrosis factor alpha (TNF-α) inhibitors like etanercept, infliximab, afelimomab, adalimumab, certolizumab pegol, golimumab; Selective immunosuppressants like muromonab-CD3, antilymphocyte immunoglobulin (horse), antithymocyte immunoglobulin (rabbit), mycophenolic acid, sirolimus, leflunomide, alefacept, everolimus, gusperimus, efalizumab, abetimus, natalizumab, abatacept, eculizumab, belimumab, fingolimod, belatacept; or Other immunosuppressants like azathioprine, thalidomide, methotrexate, lenalidomide Exemplary Hemostasis Agents In some embodiments, the biocompatible hydrogel polymer comprises a hemostasis agent (or antihemorrhagic agent). In certain embodiments, the hemostasis agent is an antifibrinolytic (amino acid or proteinase inhibitor), a vitamin K, fibrinogen, a local hemostatic, or a blood coagulation factor. Examples of hemostasis agents include, but are not limited to, Amino acids like aminocaproic acid, tranexamic acid, aminomethylbenzoic acid; Proteinase inhibitors like aprotinin, alfa1 antitrypsin, C1-inhibitor, camostat; Vitamin K like phytomenadione, menadione; Fibrinogen like Human fibrinogen; Local hemostatics like absorbable gelatin sponge, oxidized cellulose, tetragalacturonic acid hydroxymethylester, adrenalone, thrombin, collagen, calcium alginate, epinephrine, human fibrinogen; Blood coagulation factors like coagulation factor IX, II, VII and X in combination, coagulation factor VIII, factor VIII inhibitor bypassing activity, coagulation factor IX, coagulation factor VII, von Willebrand factor and coagulation factor VIII in combination, coagulation factor XIII, eptacog alfa, nonacog alfa, thrombin; Other systemic hemostatics like etamsylate, carbazochrome, batroxobin, romiplostim, eltrombopag.

Exemplary Non-Steroidal Anti-Inflammatory Agents

In some embodiments, the biocompatible hydrogel polymer comprises an anti-inflammatory agent. In certain embodiments, the anti-inflammatory agent is a non-steroidal anti-inflammatory agent. In other embodiments, the anti-inflammatory agent is a glucocorticosteroid. In some embodiments, the non-steroidal anti-inflammatory agent is a butylpyrazolidine, an acetic acid derivative, oxicam, propionic acid derivative, fenamate, or coxib. Examples of anti-inflammatory agents include, but are not limited to, Butylpyrazolidines like phenylbutazone, mofebutazone, oxyphenbutazone, clofezone, kebuzone; Acetic acid derivatives and related substances like indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, indometacin combinations, diclofenac combinations; Oxicams like piroxicam, tenoxicam, droxicam, lornoxicam, meloxicam; Propionic acid derivatives like ibuprofen, naproxen, ketoprofen, fenoprofen, fenbufen, benoxaprofen, suprofen, pirprofen, flurbiprofen, indoprofen, tioprofenoic acid, oxaprozin, ibuproxam, dexibuprofen, flunoxaprofen, alminoprofen, dexketoprofen, naproxcinod; Fenamates like mefenamic acid, tolfenamic acid, flufenamic acid, meclofenamic acid; Coxibs like celecoxib, rofecoxib, valdecoxib, parecoxib, etoricoxib, lumiracoxib; Other antiinflammatory and antirheumatic agents like nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate.

Exemplary Analgesics and Anesthetics

In some embodiments, the biocompatible hydrogel polymer comprises an analgesic or anesthetic agent. In certain embodiments, the analgesic or anesthetic agent comprises paracetamol, an opiate, diproqualone, phenazone, cocaine, or lidocaine. In certain embodiments, the opioid is a natural opium alkaloid, phenylpiperidine derivative, diphenylpropylamine derivative, benzomorphan derivative, oripavin derivative, or morphinan derivative. In some embodiments, the analgesic is a salicylic acid derivative, pyrazolone, or anilide. In other embodiments, the analgesic is an ergot alkaloid, corticosteroid derivative, or selective serotonin (5HT1) agonist. Examples of local anesthetics include, but are not limited to, Esters of aminobenzoic acid like metabutethamine, procaine, tetracaine, chloroprocaine, benzocaine; Amides like bupivacaine, lidocaine, mepivacaine, prilocaine, butanilicaine, cinchocaine, etidocaine, articaine, ropivacaine, levobupivacaine, tetracaine, chloroprocaine, benzocaine; Esters of benzoic acid like cocaine; Other local anesthetics like ethyl chloride, dyclonine, phenol, capsaicin.

Exemplary Proteins and Other Biomolecules

In some embodiments, the biocompatible hydrogel polymer comprises a protein or other biomolecule. Examples of proteins and other biomolecules include, but are not limited to abarelix, abatacept, acarbose, adalimumab, alglucosidase alfa, Antihemophilic Factor Recombinant, antithrombin recombinant lyophilized powder for reconstitution, belatacept, belimumab, bevacizumab, botulinum toxin type A, canakinumab, certolizumab pegol, Cetrotide, cetuximab, chorionic human recombinant gonadotropin, coagulation Factor IX (recombinant), collagenase *clostridium histolyticum*, conjugated estrogens, Cyanocobalamin, darbepoetin alfa, denosumab, Diphtheria and Tetanus Toxoids and Acellular Pertussis Vaccine Adsorbed, Diptheria and Tetanus Toxoids and Acellular Pertussis Vaccine Absorbed, dornase alfa, drotrecogin alfa [activated]), ecallantide, eculizumab, enfuvirtide, enoxaparin sodium, epoetin alfa, etanercept, exenatide, filgrastim, follitropin alfa, follitropin beta, Fragmin, galsulfase, gemtuzumab ozogamicin, glatiramer acetate, Glucagon, golimumab, goserelin acetate, *Haemophilus* b Conjugate Vaccine-Tetanus Toxoid Conjugate, histrelin acetate, ibritumomab tiuxetan, idursulfase, incobotulinumtoxin A, infliximab, Influenza Virus Vaccine, insulin derivatives, insulin aspart, insulin glargine [rDNA origin], insulin lispro, interferon alfacon-1, interferon beta-1a, Interferon beta-1b, ipilimumab, Japanese Encephalitis Vaccine-Inactivated-Adsorbed, lanreotide acetate, laronidase, leuprolide acetate for depot suspension, leuprolide acetate, linagliptin, liraglutide, mecasermin, menotropins, methoxy polyethylene glycol-epoetin beta, natalizumab, ofatumumab, omalizumab, onabotulinumtoxin A, palivizumab, pancrelipase, pancrelipase, panitumumab, pegaptanib, pegfilgrastim, peginterferon alfa-2a, peginterferon alfa-2b, pegloticase, pegvisomant, pentosan polysulfate sodium, pramlintide, quadrivalent human papillomavirus (types 6, 11, 16, 18) recombinant vaccine, ranibizumab, rasburicase, Recombinant Human Papillomavirus Bivalent (Types 16 and 18) Vaccine, recombinant Interferon alfa-2b, reteplase, Rituximab, romiplostim, sargramostim, secretin, sevelamer carbonate, sevelamer hydrochloride, sipuleucel-T, somatropin, somatropin [rDNA origin], teriparatide, tocilizumab, trastuzumab, triptorelin pamoate, ustekinumab, velaglucerase alfa for injection.

In certain embodiments, the biocompatible hydrogel polymer comprises a protein as a pharmaceutically active biomolecule. Examples of proteins include, but are not limited to, octreotide, eptifibatide, desmopressin, leuprolide/leuprorelin, goserelin, ciclosporin, bivalirudin, glucagon, calcitonin, teriparatide, enfuvirtide, ecallantide, romiplostim. In some embodiments, the biocompatible polymer comprises a recombinant protein as a pharmaceutically active biomolecule. Examples of recombinant proteins include, but are not limited to, insulin, lepirudin, somatropin, aldesleukin, interferon gamma 1b, anakinra, interferon alpha 2b, interferon beta 1b, interferon beta 1a, PEG interferon alpha 2a, filgrastim, pegfilgrastim, oprelvekin, reteplase, denileukin diftitox, follitropin alfa, recFSH, thyrotropin alfa, imiglucerase, becaplermin, sargramostim, darbepoetin, erythropoietin, DNAse, Factor VIIa, Factor IX, Factor XIII, drotrecogin, alteplase, tenecteplase, moroctocog alfa (BDDrFVIII), Factor VIII-2, Factor VIII, peginteferon, ribavarin, clostridial collagenese, alglucosidase alpha2, incobotulinumtoxina, pegloticase, palifermin, galsulfase, idursulfase. In certain embodiments, the biocompatible hydrogel polymer comprises an antibody as a pharmaceutically active biomolecule. Examples of antibodies include, but are not limited to, etanercept, abciximab, gemtuzumab, rituximab, adalimumab, palivizumab, trastuzumab, bevacizumab, natalizumab, omalizumab, infliximab, alemtuzumab, efalizumab, cetuximab, golimumab, abobotulinumtoxina, canakinumab, ustekinumab, ofatumumab, certolizumab pegol, tocilizumab, denosumab, abatacept, ranibizumab, panitumumab, eculizumab, brentixumab, iplimumab, belimumab, rilonacept.

Exemplary Combinations

In some embodiments, a second therapeutic agent can be incorporated into the biocompatible hydrogel polymer formulation. Provided herein are in vivo gelling pharmaceutical pre-formulations, comprising a first compound comprising more than one nucleophilic group, a second compound comprising more than one electrophilic group, a first therapeutic agent, a second therapeutic agent, and an aqueous buffer in the pH range of about 5.0 to about 9.5, wherein a biocompatible hydrogel polymer is formed following mixing the first compound and the second compound in the aqueous buffer; and wherein the biocompatible hydrogel polymer gels at a target site. In some embodiments, the first compound and the second compound do not react with the first and second therapeutic agent during formation of the biocompatible hydrogel polymer.

In certain embodiments, the in vivo gelling pharmaceutical pre-formulations comprise a protein or other biomolecule and at least one additional therapeutic agent. Additional therapeutic agents include, but are not limited to, anesthetics, antibacterial compounds, antiviral compounds, immunosuppressants, anti-inflammatory compounds, anti-proliferative compounds, anti-angiogenesis compounds, or hormones.

In some embodiments, the biocompatible hydrogel polymer or in vivo gelling pre-formulations further comprise a visualization agent for visualizing the placement of the biocompatible hydrogel polymer at a target site The visualization agent assists in visualizing the placement using minimally invasive delivery, e.g., using an endoscopic device. In certain embodiments, the visualization agent is a dye. In specific embodiments, the visualization agent is colorant.

In some embodiments, the biocompatible hydrogel polymer formulations further comprise a contrast agent for visualizing the hydrogel formulation and locating a tumor using e.g., X-ray, fluoroscopy, or computed tomography (CT) imaging. In certain embodiments, the contrast agent is radiopaque. In some embodiments, the radiopaque material is selected from sodium iodide, potassium iodide, barium sulfate, VISIPAQUE®, OMNIPAQUE®, or HYPAQUE®, tantalum, and similar commercially available compounds, or combinations thereof.

Exemplary Kits

Further provided herein is a kit comprising a) a first compound comprising more than one nucleophilic group, and a therapeutic agent in an aqueous buffer; and b) a second compound comprising more than one electrophilic group; wherein a biocompatible hydrogel polymer is formed following mixing the first compound and the second compound in the aqueous buffer.

Also provided here is a kit comprising a) a first compound comprising more than one electrophilic group, and a therapeutic agent in an aqueous buffer; and b) a second compound comprising more than one nucleophilic group; wherein a biocompatible hydrogel polymer is formed following mixing the first compound and the second compound in the aqueous buffer.

Further provided herein is a kit for preparing any in vivo gelling pharmaceutical pre-formulation as described herein, comprising a first container with a first amount of the first compound, a second container with a second amount of the second compound, a third container with a third amount of the therapeutic agent, a fourth container with the aqueous buffer, a mixing vessel, optionally a fifth container with the radiopaque material, instructions for mixing the materials present in each container in the mixing vessel to produce the biocompatible hydrogel polymer, and instructions for delivering the biocompatible hydrogel polymer to a target site.

Also provided herein is a kit for preparing any in vivo gelling pharmaceutical pre-formulation as described herein, comprising a first container comprising a first amount of the first compound and a second amount of the therapeutic agent, a second container with a third amount of the second compound, a third container with the aqueous buffer, a mixing vessel, optionally a fourth container with the radiopaque material, instructions for mixing the materials present in each container in the mixing vessel to produce the biocompatible hydrogel polymer, and instructions for delivering the biocompatible hydrogel polymer to a target site.

Further provided herein is a kit for preparing any in vivo gelling pharmaceutical pre-formulation as described herein, comprising a first container comprising a first amount of the first compound, a second container with a second amount of the second compound and a third amount of the therapeutic agent, a third container with the aqueous buffer, a mixing vessel, optionally a fourth container with the radiopaque material, instructions for mixing the materials present in each container in the mixing vessel to produce the biocompatible hydrogel polymer, and instructions for delivering the biocompatible hydrogel polymer to a target site.

Additionally provided herein is a kit for preparing an in vivo gelling pharmaceutical pre-formulation comprising (a) a first container with a first amount of the at least one first compound; (b) a second container with a second amount of the at least one second compound; (c) a third container with the aqueous buffer; (d) a mixing vessel; (e) optionally, a fourth container with a third amount of one or more therapeutic agent; (f) optionally, a fifth container with the radiopaque material or dye; and instructions for mixing the materials present in each container in the mixing vessel to produce the biocompatible hydrogel polymer, and instructions for delivering the biocompatible hydrogel polymer to the target site inside the human body. In certain embodiments, the first container and the second container each are a syringe, wherein the plungers of the syringes are interconnected, and the outlets of the two syringes are connected to the mixing vessel. In some embodiments, the mixing vessel is connected to a catheter attached to an endoscopic device.

EXAMPLES

The following specific examples are to be construed as merely illustrative, and not limitative of the remainder of the disclosure in any way whatsoever.

The chemical components of the polymers are listed in Table 1. The chemicals will be referred to by their part numbers. The chemicals were stored at 5° C. and allowed to warm to room temperature before use, which typically took 30 minutes. After use the contents were purged with $N_2$ for approximately 30 seconds before sealing with parafilm and returning to 5° C. Lysozyme was handled in a similar fashion, except that it was stored at −10° C.

A 0.058 M phosphate buffer was made by dissolving 3.45 g (0.029 mol) of $NaH_2PO_4$ in 500 mL of distilled water at 25° C. with magnetic stirring. The pH was then adjusted to 7.97 with the dropwise addition of 50% aqueous NaOH. A 0.05 M borate buffer was made by dissolving 9.53 g (0.025 mol) of $Na_2B_4O_7.10H_2O$ in 500 mL of distilled water at 25° C. with magnetic stirring. The pH was then adjusted to 7.93 or 8.35 with the dropwise addition of 6.0 N HCl. Phosphate buffered saline (PBS) was prepared by dissolving two PBS tablets (Sigma Chemical, P4417) in 400 mL of distilled water at 25° C. with vigorous shaking. The resulting buffer solution had the following composition and pH: 0.01 M phosphate, 0.0027 M potassium chloride, 0.137 M sodium chloride, pH 7.45.

TABLE 1

Components used in formulations.

| Components | Technical Name |
| --- | --- |
| ETTMP-1300 | Ethoxylated trimethylolpropane tri(3-mercaptopropionate) |
| 4ARM-5k-SH | 4ARM PEG Thiol (pentaerythritol) |
| 4ARM-5k-NH2 | 8ARM PEG Amine (pentaerythritol), HCl Salt, MW 5000 |
| 8ARM-20k-NH2 | 8ARM PEG Amine (hexaglycerol), HCl Salt, MW 20000 |
| 4ARM-20k-AA | 4ARMPEG Acetate Amine HCl Salt, MW 20000 |
| 4ARM-10k-SG | 4ARM PEG Succinimidyl Glutarate (pentaerythritol), MW 10000 |
| 8ARM-15k-SG | 8ARM PEG Succinimidyl Glutarate (hexaglycerol), MW 15000 |
| 4ARM-20k-SGA | 4ARM PEG Succinimidyl Glutaramide (pentaerythritol), MW 20000 |
| 4ARM-10k-SS | 4ARM PEG Succinimidyl Succinate (pentaerythritol), MW 10000 |
| EJ-190 | Sorbitol polyglycidyl ether |

The amine or thiol component (typically in the range of 0.1 mmol arms equivalents) was added to a 50 mL centrifuge tube. A volume of reaction buffer was added to the tube via a pipette such that the final concentration of solids in solution was about 5 percent. The mixture was gently swirled to dissolve the solids before adding the appropriate amount of ester or epoxide Immediately after adding the ester or epoxide, the entire solution was shaken for 10 seconds before letting it rest.

The gel time for all cases was measured starting from the addition of the ester or epoxide until the gelation of the solution. The gel point was noted by pipetting 1 mL of the reaction mixture and observing the dropwise increase in viscosity. Degradation of the polymers was performed by the addition of 5 to 10 mL, of phosphate buffered saline to ca. 5 g of the material in a 50 mL centrifuge tube and incubating the mixture at 37° C. The degradation time was measured starting from the day of addition of the phosphate buffer to complete dissolution of the polymer into solution.

Bovine serum albumin (BSA) and lysozyme were used as model proteins to study the controlled release of proteins from various amine-ester and thiol-ester based polymers. The protein loaded polymers were prepared in several minutes under mild conditions and exhibited no significant differences in gel and degradation times with polymers possessing no protein. The daily release of protein was monitored and quantified via the Bradford assay. The pore sizes of the polymers were estimated and it was found that the elution of protein is enhanced by increasing the pore size relative to the size of the protein. An acceptable elution rate is expected when the ratio of pore diameter to protein is about 8. The pore sizes may be adjusted by changing the number of arms and molecular weights of the monomers and by varying the water content of the polymer.

A 10 mg/mL BSA loading concentration was chosen based on the solubility of BSA in water and the linearity of the Bradford assay in that concentration range. For similar reasons, a 20 mg/mL lysozyme loading concentration was used.

Example 1: Manufacture of Hydrogel (Amine-Ester Chemistry)

A solution of 8ARM-20K-NH2 was prepared in a Falcon tube by dissolving about 0.13 g solid monomer in about 2.5 mL of sodium phosphate buffer (buffer pH 7.36). The mixture was shaken for about 10 seconds at ambient temperature until complete dissolution was obtained. The Falcon tube was allowed to stand at ambient temperature. In another Falcon tube, 0.10 g of 8ARM-15K-SG was dissolved in the same phosphate buffer as above. The mixture was shaken for about 10 seconds and at this point all the powder dissolved. The 8ARM-15K-SG solution was poured immediately into the 8ARM-20K-NH2 solution and a timer was started. The mixture was shaken and mixed for about 10 seconds and a 1 mL solution of the mixture was pipetted out using a mechanical high precision pipette. The gel time of 1 mL liquid was collected and then verified with the lack of flow for the remaining liquids. The get time data of the formulation was recorded and was about 90 seconds.

Example 2: Manufacture of Hydrogel (Amine-Ester Chemistry)

A solution of amines was prepared in a Falcon tube by dissolving about 0.4 g solid 4ARM-20k-AA and about 0.2 g solid 8ARM-20k-NH2 in about 18 mL of sodium phosphate buffer (buffer pH 7.36). The mixture was shaken for about 10 seconds at ambient temperature until complete dissolution was obtained. The Falcon tube was allowed to stand at ambient temperature. To this solution, 0.3 g of 8ARM-15K-SG was added. The mixture was shaken to mix for about 10 seconds until all the powder dissolved. 1 mL of the mixture was pipetted out using a mechanical high precision pipette. The gel time of the formulation was collected using the process described above. The gel time was about 90 seconds.

Example 3: Manufacture of Hydrogel (Thiol-Ester Chemistry

A solution of ETTMP-1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.20 g of 8ARM-15K-SG was added. The mixture was shaken for about 10 seconds until the powder dissolved. 1 mL of the mixture was pipetted out using a mechanical high precision pipette. The gel time was found to be about 70 seconds.

Example 4: Manufacture of Hydrogel (Thiol-Epoxide Chemistry)

A solution of ETTMP-1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of EJ-190 was added. The mixture was shaken for about 10 seconds until complete dissolution is obtained. 1 mL of the mixture was pipetted out using a mechanical high precision pipette. The gel time was found to be about 6 minutes.

Example 5: In Vitro Bioabsorbance Testing

A 0.10 molar buffer solution of pH 7.40 was prepared with deionized water. A 50 mL portion of this solution was transferred to a Falcon tube. A sample polymer was prepared in a 20 cc syringe. After curing, a 2-4 mm thick slice was cut from the polymer slug and was placed in the Falcon tube. A circulating water bath was prepared and maintained at 37° C. The Falcon tube with polymer was placed inside the water bath and time was started. The dissolution of the polymer was monitored and recorded. The dissolution time ranged from 1-90 days depending on the type of sample polymer.

Example 6: Gelling and Degradation Times of Amine-Ester Polymers

Amines studied were 8ARM-20k-NH2 and 4ARM-5k-NH2. The formulation details and material properties are given in Table 2. With 8ARM-20k-NH2, it was found that a phosphate buffer with 0.058 M phosphate and pH of 7.97 was necessary to obtain acceptable gel times of around 100 seconds. Using a 0.05 M phosphate buffer with a pH of 7.41 resulted in a more than two-fold increase in gel time (270 seconds).

With the 8ARM-20k-NH2, the ratio of 4ARM-10k-SS to 4ARM-20k-SGA was varied from 50:50 to 90:10. The gel time remained consistent, but there was a marked shift in degradation time around a ratio of 80:20. For formulations with ratios of 75:25 and 50:50, degradation times spiked to one month and beyond. Using lower amounts of 4ARM-20k-SGA (80:20, 85:15, 90:10) resulted in degradation times of less than 7 days.

As a comparison, the 4ARM-5k-NH2 was used in a formulation with a ratio of 4ARM-10k-SS to 4ARM-20k-SGA of 80:20. As was expected, the degradation time remained consistent, which suggests that the mechanism of degradation was unaffected by the change in amine. However, the gel time increased by 60 seconds, which may reflect the relative accessibility of reactive groups in a high molecular weight 8ARM amine and a low molecular weight 4ARM amine.

TABLE 2

Gel and degradation times for varying 4ARM-10k-SS/4ARM-20k-SGA ratios with 8ARM-15k-SG ester.

| Components | Ratio of 4ARM-10k-SS/ 4ARM-20k-SGA | Phosphate Reaction Buffer Concentration and pH | Gel Time (s) | Degradation Time (days) |
|---|---|---|---|---|
| 8ARM-20k-NH2 & 4ARM-10k-SS, 4ARM-20k-SGA | 50/50 | 0.05M pH 7.41 | 270 | N/A |
| 8ARM-20k-NH2 & 4ARM-10k-SS, 4ARM-20k-SGA | 50/50 | 0.058M pH 7.97 | 100 | >41 |
| 8ARM-20k-NH2 & 4ARM-10k-SS, 4ARM-20k-SGA | 75/25 | 0.058M pH 7.97 | 90 | 29 |
| 8ARM-20k-NH2 & 4ARM-10k-SS, 4ARM-20k-SGA | 80/20 | 0.058M pH 7.97 | 100 | 7 |
| 4ARM-5k-NH2 & 4ARM-10k-SS, 4ARM-20k-SGA | 80/20 | 0.058M pH 7.97 | 160 | 6 |
| 8ARM-20k-NH2 & 4ARM-10k-SS, 4ARM-20k-SGA | 85/15 | 0.058M pH 7.97 | 100 | 5 |
| 8ARM-20k-NH2 & 4ARM-10k-SS, 4ARM-20k-SGA | 90/10 | 0.058M pH 7.97 | 90 | 6 |

Example 7: Gelling and Degradation Times of Thiol-Ester Polymers

Thiols studied were 4ARM-5k-SH and ETTMP-1300. The formulation details and material properties are given in Table 3. It was found that a 0.05 M borate buffer with a pH of 7.93 produced gel times of around 120 seconds. Increasing the amount of 4ARM-20k-SGA in the formulation increased the gel time to 190 seconds (25:75 ratio of 4ARM-10k-SS to 4ARM-20k-SGA) up to 390 seconds (0:100 ratio of 4ARM-10k-SS to 4ARM-20k-SGA). Using a 0.05 M borate buffer with a pH of 8.35 resulted in a gel time of 65 seconds, about a two-fold decrease in gel time. Thus, the gel time may be tailored by simply adjusting the pH of the reaction buffer.

The ratio of 4ARM-10k-SS to 4ARM-20k-SGA was varied from 0:100 to 100:0. In all cases, the degradation time did not vary significantly and was typically between 3 and 5 days. It is likely that degradation is occurring via alternate pathways.

TABLE 3

Gel and degradation times for varying 4ARM-10k-SS/4ARM-20k-SGA ratios with 4ARM-5k-SH and ETTMP-1300 thiols.

| Components | Ratio of 4ARM-10k-SS/ 4ARM-20k-SGA | Phosphate Reaction Buffer Concentration and pH | Gel Time (s) | Degradation Time (days) |
|---|---|---|---|---|
| 4ARM-5k-SH & 4ARM-10k-SS, 4ARM-20k-SGA | 50/50 | 0.05M pH 8.35 | 65 | N/A |
| 4ARM-5k-SH & 4ARM-10k-SS, 4ARM-20k-SGA | 50/50 | 0.05M pH 7.93 | 120 | 4 |
| 4ARM-5k-SH & 4ARM-10k-SS, 4ARM-20k-SGA | 75/25 | 0.05M pH 7.93 | 125 | 4 |
| 4ARM-5k-SH & 4ARM-10k-SS, 4ARM-20k-SGA | 90/10 | 0.05M pH 7.93 | 115 | 4 |
| 4ARM-5k-SH & 4ARM-10k-SS, 4ARM-20k-SGA | 25/75 | 0.05M pH 7.93 | 190 | 4 |
| 4ARM-5k-SH & 4ARM-10k-SS, 4ARM-20k-SGA | 10/90 | 0.05M pH 7.93 | 200 | 4 |

TABLE 3-continued

Gel and degradation times for varying 4ARM-10k-SS/4ARM-20k-SGA ratios with 4ARM-5k-SH and ETTMP-1300 thiols.

| Components | Ratio of 4ARM-10k-SS/ 4ARM-20k-SGA | Phosphate Reaction Buffer Concentration and pH | Gel Time (s) | Degradation Time (days) |
|---|---|---|---|---|
| ETTMP-1300 & 4ARM-20k-SGA | 0/100 | 0.05M | 390 | 3 |
| 4ARM-5k-SH & 4ARM-10k-SS | 100/0 | 0.05M pH 7.93 | 120 | 4 |

Example 8: Gelling and Degradation Times of Amine-Ester and Thiol-Ester Polymers An amine (4ARM-5k-NH2) and a thiol (4ARM-5k-SH) were studied with the ester 4ARM-10k-SG. The formulation details and material properties are given in Table 4. A 0.058 M phosphate buffer with a pH of 7.97 yielded a gel time of 150 seconds with the amine. A 0.05 M borate buffer with a pH of 8.35 produced a gel time of 75 seconds with the thiol.

The amine-based polymer appeared to show no signs of degradation, as was expected from the lack of degradable groups. However, the thiol-based polymer degraded in 5 days. This suggests that degradation is occurring through alternate pathways, as was observed in the thiol formulations with 4ARM-10k-SS and 4ARM-20k-SGA (vida supra).

TABLE 4

Gel and degradation times for amines and thiols with 4ARM-10k-SG formulations.

| Components | Reaction Buffer Type, Concentration, and pH | Gel Time (s) | Degradation Time (days) |
|---|---|---|---|
| 4ARM-5k-NH2 & 4ARM-10k-SG | Phosphate (0.058M, pH 7.97) | 150 | Indefinite |
| 4ARM-5k-SH & 4ARM-10k-SG | Borate (0.05M, pH 8.35) | 75 | 5 |

Example 9: Gelling and Degradation Times of Thiol-Sorbitol Polyglycidyl Ether Polymers With ETTMP-1300 conditions such as high pH (10), high solution concentration (50%), or high borate concentration (0.16 M) were necessary for the mixture to gel. Gel times ranged from around 30 minutes to many hours. The conditions that were explored include: pH from 7 to 12; solution concentration from 5% to 50%; borate concentration from 0.05 M to 0.16 M; and thiol to epoxide ratios from 1:2 to 2:1.

The high pH necessary for the reaction to occur could result in degradation of the thiol. Thus, a polymer with EJ-190 and 4ARM-5k-SH was prepared. A 13% solution formulation exhibited a gel time of 230 seconds at a pH of between 9 and 10. The degradation time was 32 days. At a lower pH of around 8, the mixture exhibited gel times in the range of 1 to 2 hours.

Example 10: Preparation of a Biocompatible Hydrogel Polymer Comprising Proteins In general, the formulations with proteins proceeded similar to those without the addition of proteins. Similar trends in gel times were observed by varying the reactant concentration and pH of the reaction buffer. With lower percent solution formulations, the gel times increased due to the dilution of reactants. The gel time may be decreased by using a higher pH buffer (pH 7.93, gel time of 160 seconds versus pH 8.35, gel time of 50 seconds). When lysozyme was used, an overall slight increase in gel time was observed, due to the presence of residual acid in the protein decreasing the pH of the reaction buffer. Bovine serum albumin (BSA) is known to foam in solution and during the mixing of formulations with BSA some foaming was observed. Finally, the degradation times with BSA all remained within the expected ranges. However, the degradation times with Lysozyme containing formulations were reduced by as much as half of the without protein formulations.

Several control experiments were performed to assess any effect of the protein on the properties of the material. The proteins were incubated with 8ARM-15k-SG over one day. No sign of reaction was observed. An alternate formulation procedure was also explored, in which the protein was added about 60 seconds after mixing the amine and ester components in the buffer. No change in gel time, degradation time (for BSA only), or elution behavior was observed.

Example 11: Preparation of a Biocompatible Hydrogel Polymer Comprising Lysozyme A solution of 4ARM-20k-AA was prepared in a Falcon tube by dissolving about 0.12 g solid monomer in about 5.0 mL of sodium phosphate buffer (buffer pH 7.97). The mixture was gently swirled for about 10 seconds at ambient temperature until complete dissolution was obtained. Lysozyme (100 mg) was added to this solution and the mixing was continued for another 5 seconds until the Lysozyme is completely dissolved. To this solution was added 0.12 g of 4ARM-20k-SGA and the entire mixture was shaken for about 10 seconds. A timer was started and 1 mL solution of the mixture was pipetted out using a mechanical high precision pipette. The gel time of 1 mL liquid was collected and then verified with the lack of flow for the remaining liquids. The gel time data of the formulation was recorded and was about 5 min 45 seconds.

Example 12: Preparation of a Biocompatible Hydrogel Polymer Comprising Bovine Serum Albumin A solution of ETTMP-1300 was prepared in a Falcon tube by dissolving about 0.07 g monomer in about 5.0 mL of sodium borate buffer (buffer pH 8.35). The mixture was shaken for about 10 seconds at ambient temperature until complete dissolution was obtained. Bovine serum albumin (BSA, 50 mg) was added to this solution and the mixing was continued for another 5 seconds until the BSA is completely mixed. To this solution was added 0.30 g of 8ARM-15k-SG and the mixture was shaken for about 10 seconds. A timer was started and 1 mL solution of the mixture was pipetted out using a mechanical high precision pipette. The gel time of 1 mL liquid was collected and then verified with the lack of flow for the remaining liquids. The gel time data of the formulation was recorded and was about 50 seconds.

Example 13: Bradford Assay of Protein Concentrations

The hydrogel was prepared as described above in EXAMPLE 10 or EXAMPLE 12. Aqueous samples for analysis were collected daily by simply decanting the liquid from the gel. The amount of liquid collected was replaced with fresh PBS and the mixture was returned to 37° C. The collected samples were stored at 5° C.

The assay was performed by pipetting 1.5 mL of the Bradford reagent into a cuvette. For the determination of BSA concentrations, 0.1 mL of sample was pipetted into the cuvette containing the reagent. The color was allowed to develop over 5 minutes. In the case of lysozyme, 0.2 mL of sample was used and the color was allowed to develop over 15 minutes.

The protein concentration was determined qualitatively via comparison with standard concentrations. For BSA, the following solutions were prepared via standard dilution methods and analyzed with the Bradford assay: 10, 7.5, 5, 2.5, 1, 0.5, 0.25 and 0 mg/mL of BSA in PBS; for lysozyme: 10, 5, 1, 0.5, 0.25, 0 mg/mL of lysozyme in PBS.

BSA exhibited distinct colors for BSA concentrations of 10, 2.5, 1, 0.5, 0.25 and 0 mg/mL. The 5 and 7.5 mg/mL BSA concentrations were visually indistinguishable from 10 mg/mL. In the case of lysozyme, the developed colors were not as distinct as with BSA, but concentrations of 10, 5, 1, 0.5 and 0 mg/mL were able to be distinguished. The 0.25 mg/mL lysozyme concentration was visually indistinguishable from 0.5 mg/mL. Additionally, assays with lysozyme required an extended period of time for the color to fully develop; at least 15 minutes was necessary.

Several control experiments were performed to verify the accuracy of the Bradford assay. A small sample of polymer loaded with BSA was treated with the Bradford reagent. A distinct color indicative of the loaded protein concentration developed throughout the polymer, which provides strong evidence for the presence of the protein and its homogeneous distribution in the polymer matrix. Similarly, a polymer sample without BSA was treated with the Bradford reagent and only a faint color developed at the outer edges of the polymer. The faint color is presumably from unreacted amine groups in the monomers or degradation of the polymer. Indeed, a solution of the amine containing monomers in the same proportions produced a similar color change that appeared to be between 0 and 0.25 mg/mL. Finally, each protein was dissolved in PBS and stored over about one month at either 5° C. or 37° C. and assayed periodically to determine any changes in color under the anticipated experiment conditions. No visually observable color changes were found.

Example 14: Pore Size Determination

The pore diameters were estimated from the molecular weight per arm of the combined components. The pore diameter was calculated based on the number of PEG units per arm and a carbon-carbon-carbon bond length of 0.252 nm with a 110° bond angle. This assumes a fully extended chain that accounts for bonding angles and complete reactivity of all functional end groups to form the pore network. The pore diameter was further modified by a correlation relating the pore size to the inverse of the hydrogel swelling ratio:

$$\xi \approx L^*(V_p/V_s)^{-1/3} \quad \text{(Equation 1)}$$

where $V_p$ is the volume of polymer, $V_s$ is the volume of the swollen gel, L is the calculated pore diameter, and $\xi$ is the swollen pore diameter. Based on equilibrium swelling experiments, the ratio of $V_p$ to $V_s$ was estimated to be around 0.5.

For the case of multi-component mixtures with a reactive ester, the weighted average of each component with the ester was used. For example, the pore sizes obtained from 4ARM-20k-AA with 4ARM-20k-SGA are averaged with the pore sizes obtained from 8ARM-20k-NH2 with 4ARM-20k-SGA for polymers comprised of 4ARM-20k-AA and 8ARM-20k-NH2 with 4ARM-20k-SGA.

Finally, to aid in the comparison of elution behavior with different proteins, the ratio of the pore diameter to the protein size was calculated. The hydrodynamic radius was used as a measure of the protein size. Typical values are around 1.9 nm and 3.5 nm for lysozyme and BSA, respectively. Thus, the size of lysozyme was estimated as 4 nm and the size of BSA was estimated as 7 nm.

Example 15: Protein Elution from Amine-Ester Hydrogel

In general, the formulations with proteins proceeded similar to those without the addition of proteins. The hydrogel was generally prepared as described above in EXAMPLE 11 or EXAMPLE 12. More specific reaction details are listed in Table 5.

TABLE 5

A summary of the reaction details for formulations studied.

| Material ID | Components | MW | Mmoles | Wt (g) | Arm | mmoles | Arms Eq | Polymer % Solution (w/v) |
|---|---|---|---|---|---|---|---|---|
| 1 | 4ARM-20k-AA | 20000 | 1000 | 0.2 | 4 | 0.01 | 0.04 | |
| | 8ARM-15k-SG | 15000 | 1000 | 0.075 | 8 | 0.005 | 0.04 | |
| | Buffer Volume | | | 5 | | | | 5.5 |
| | BSA Loading | | | 0.05 | | | | |
| 2 | 4ARM-20k-AA | 20000 | 1000 | 0.2 | 4 | 0.01 | 0.04 | |
| | 8ARM-15k-SG | 15000 | 1000 | 0.075 | 8 | 0.005 | 0.04 | |
| | Buffer Volume | | | 5 | | | | 5.5 |
| | BSA Loading | | | 0.05 | | | | |
| 3 | 4ARM-20k-AA | 20000 | 1000 | 0.12 | 4 | 0.006 | 0.024 | |
| | 8ARM-15k-SG | 15000 | 1000 | 0.045 | 8 | 0.003 | 0.024 | |
| | Buffer Volume | | | 5 | | | | 3.3 |
| | BSA Loading | | | 0.05 | | | | |
| 4 | ETTMP-1300 | 1300 | 1000 | 0.069 | 3 | 0.053 | 0.16 | |
| | 8ARM-15k-SG | 15000 | 1000 | 0.3 | 8 | 0.02 | 0.16 | |
| | Buffer Volume | | | 5 | | | | 7.4 |
| | BSA Loading | | | 0.05 | | | | |

TABLE 5-continued

A summary of the reaction details for formulations studied.

| Material ID | Components | MW | Mmoles | Wt (g) | Arm | mmoles | Arms Eq | Polymer % Solution (w/v) |
|---|---|---|---|---|---|---|---|---|
| 5 | 4ARM-20k-AA | 20000 | 1000 | 0.2 | 4 | 0.01 | 0.04 | |
|  | 8ARM-15k-SG | 15000 | 1000 | 0.075 | 8 | 0.005 | 0.04 | |
|  | Buffer Volume |  |  | 5 |  |  |  | 5.5 |
|  | Lysozyme Loading |  |  | 0.1 |  |  |  |  |
| 6 | ETTMP-1300 | 1300 | 1000 | 0.049 | 3 | 0.038 | 0.11 | |
|  | 8ARM-15k-SG | 15000 | 1000 | 0.21 | 8 | 0.014 | 0.11 | |
|  | Buffer Volume |  |  | 5 |  |  |  | 5.2 |
|  | BSA Loading |  |  | 0.05 |  |  |  |  |
| 7 | 4ARM-20k-AA | 20000 | 1000 | 0.12 | 4 | 0.006 | 0.024 | |
|  | 4ARM-20k-SGA | 20000 | 1000 | 0.12 | 4 | 0.006 | 0.024 | |
|  | Buffer Volume |  |  | 5 |  |  |  | 4.8 |
|  | BSA Loading |  |  | 0.05 |  |  |  |  |
| 8 | 4ARM-20k-AA | 20000 | 1000 | 0.075 | 4 | 0.0038 | 0.015 | |
|  | 4ARM-20k-SGA | 20000 | 1000 | 0.075 | 4 | 0.0038 | 0.015 | |
|  | Buffer Volume |  |  | 5 |  |  |  | 3 |
|  | BSA Loading |  |  | 0.05 |  |  |  |  |
| 9 | 4ARM-20k-AA | 20000 | 1000 | 0.04 | 4 | 0.002 | 0.008 | |
|  | 8ARM-20k-NH2 | 20000 | 1000 | 0.02 | 8 | 0.001 | 0.008 | |
|  | 4ARM-20k-SGA | 20000 | 1000 | 0.08 | 4 | 0.004 | 0.016 | |
|  | Buffer Volume |  |  | 4.6 |  |  |  | 3.0 |
|  | BSA Loading |  |  | 0.046 |  |  |  |  |
| 10 | 4ARM-20k-AA | 20000 | 1000 | 0.12 | 4 | 0.006 | 0.024 | |
|  | 4ARM-20k-SGA | 20000 | 1000 | 0.12 | 4 | 0.006 | 0.024 | |
|  | Buffer Volume |  |  | 5 |  |  |  | 4.8 |
|  | Lysozyme Loading |  |  | 0.1 |  |  |  |  |
| 11 | 4ARM-20k-AA | 20000 | 1000 | 0.16 | 4 | 0.008 | 0.032 | |
|  | 4ARM-10k-SG- | 10000 | 1000 | 0.08 | 4 | 0.008 | 0.032 | |
|  | Buffer Volume |  |  | 5 |  |  |  | 4.8 |
|  | Lysozyme Loading |  |  | 0.1 |  |  |  |  |
| 12 | 4ARM-20k-AA | 20000 | 1000 | 0.06 | 4 | 0.003 | 0.012 | |
|  | 8ARM-20k-NH2 | 20000 | 1000 | 0.01 | 8 | 0.0005 | 0.004 | |
|  | 4ARM-20k-SGA | 20000 | 1000 | 0.08 | 4 | 0.004 | 0.016 | |
|  | Buffer Volume |  |  | 5 |  |  |  | 3 |
|  | BSA Loading |  |  | 0.05 |  |  |  |  |
| 13 | 4ARM-10k-SS | 10000 | 1000 | 0.13 | 4 | 0.013 | 0.052 | |
|  | 4ARM-10k-SG- | 10000 | 1000 | 0.032 | 8 | 0.0032 | 0.026 | |
|  | 4ARM-5k-NH2 | 5000 | 1000 | 0.081 | 4 | 0.0162 | 0.065 | |
|  | Buffer Volume |  |  | 5 |  |  |  | 4.9 |
|  | Lysozyme Loading |  |  | 0.1 |  |  |  |  |
| 14 | ETTMP-1300 | 1300 | 1000 | 0.049 | 3 | 0.038 | 0.11 | |
|  | 8ARM-15k-SG | 15000 | 1000 | 0.21 | 8 | 0.014 | 0.11 | |
|  | Buffer Volume |  |  | 5 |  |  |  | 5.2 |
|  | Lysozyme Loading |  |  | 0.1 |  |  |  |  |
| 15 | 4ARM-20k-AA | 20000 | 1000 | 0.09 | 4 | 0.0045 | 0.018 | |
|  | 8ARM-20k-NH2 | 20000 | 1000 | 0.015 | 8 | 0.00075 | 0.006 | |
|  | 4ARM-20k-SGA | 20000 | 1000 | 0.12 | 4 | 0.006 | 0.024 | |
|  | Buffer Volume |  |  | 4.5 |  |  |  | 5 |
|  | Lysozyme Loading |  |  | 0.09 |  |  |  |  |
| 16 | 4ARM-20k-AA | 20000 | 1000 | 0.08 | 4 | 0.004 | 0.016 | |
|  | 8ARM-15k-SG | 15000 | 1000 | 0.03 | 8 | 0.002 | 0.016 | |
|  | Buffer Volume |  |  | 5 |  |  |  | 2.2 |
|  | BSA Loading |  |  | 0.05 |  |  |  |  |
| 17 | 4ARM-20k-AA | 20000 | 1000 | 0.24 | 4 | 0.012 | 0.048 | |
|  | 8ARM-15k-SG | 15000 | 1000 | 0.09 | 8 | 0.006 | 0.048 | |
|  | Buffer Volume |  |  | 5 |  |  |  | 6.6 |
|  | BSA Loading |  |  | 0.05 |  |  |  |  |
| 18 | 4ARM-20k-AA | 20000 | 1000 | 0.24 | 4 | 0.012 | 0.048 | |
|  | 8ARM-15k-SG | 15000 | 1000 | 0.09 | 8 | 0.006 | 0.048 | |
|  | Buffer Volume |  |  | 4 |  |  |  | 8.3 |
|  | BSA Loading |  |  | 0.04 |  |  |  |  |
| 19 | 4ARM-20k-AA | 20000 | 1000 | 0.04 | 4 | 0.002 | 0.008 | |
|  | 8ARM-20k-NH2 | 20000 | 1000 | 0.02 | 8 | 0.001 | 0.008 | |
|  | 4ARM-20k-SGA | 20000 | 1000 | 0.08 | 4 | 0.004 | 0.016 | |
|  | Buffer Volume |  |  | 4.6 |  |  |  | 3.0 |
|  | BSA Loading |  |  | 0.046 |  |  |  |  |
| 20 | 4ARM-20k-AA | 20000 | 1000 | 0.06 | 4 | 0.003 | 0.012 | |
|  | 8ARM-20k-NH2 | 20000 | 1000 | 0.01 | 8 | 0.0005 | 0.004 | |
|  | 4ARM-20k-SGA | 20000 | 1000 | 0.08 | 4 | 0.004 | 0.016 | |
|  | Buffer Volume |  |  | 5 |  |  |  | 3.0 |
|  | Lysozyme Loading |  |  | 0.1 |  |  |  |  |
| 21 | 4ARM-20k-AA | 20000 | 1000 | 0.04 | 4 | 0.002 | 0.008 | |
|  | 8ARM-20k-NH2 | 20000 | 1000 | 0.02 | 8 | 0.001 | 0.008 | |
|  | 4ARM-20k-SGA | 20000 | 1000 | 0.08 | 4 | 0.004 | 0.016 | |
|  | Buffer Volume |  |  | 4.6 |  |  |  | 3.0 |
|  | Lysozyme Loading |  |  | 0.092 |  |  |  |  |

TABLE 5-continued

A summary of the reaction details for formulations studied.

| Material ID | Components | MW | Mmoles | Wt (g) | Arm | mmoles | Arms Eq | Polymer % Solution (w/v) |
|---|---|---|---|---|---|---|---|---|
| 22 | 4ARM-20k-AA | 20000 | 1000 | 0.04 | 4 | 0.002 | 0.008 | |
| | 8ARM-20k-NH2 | 20000 | 1000 | 0.02 | 8 | 0.001 | 0.008 | |
| | 4ARM-20k-SGA | 20000 | 1000 | 0.08 | 4 | 0.004 | 0.016 | |
| | Buffer Volume | | | 4.6 | | | | 3.0 |
| | BSA Loading | | | 0.046 | | | | |
| 23 | 4ARM-20k-AA | 20000 | 1000 | 0.06 | 4 | 0.003 | 0.012 | |
| | 8ARM-20k-NH2 | 20000 | 1000 | 0.01 | 8 | 0.0005 | 0.004 | |
| | 4ARM-20k-SGA | 20000 | 1000 | 0.08 | 4 | 0.004 | 0.016 | |
| | Buffer Volume | | | 5 | | | | 3.0 |
| | BSA Loading | | | 0.05 | | | | |
| 24 | 4ARM-20k-AA | 20000 | 1000 | 0.24 | 4 | 0.012 | 0.048 | |
| | 8ARM-15k-SG | 15000 | 1000 | 0.09 | 8 | 0.006 | 0.048 | |
| | Buffer Volume | | | 4 | | | | 8.3 |
| | BSA Loading | | | 0.04 | | | | |
| 25 | 4ARM-20k-AA | 20000 | 1000 | 0.04 | 4 | 0.002 | 0.008 | |
| | 8ARM-20k-NH2 | 20000 | 1000 | 0.02 | 8 | 0.001 | 0.008 | |
| | 4ARM-20k-SGA | 20000 | 1000 | 0.08 | 4 | 0.004 | 0.016 | |
| | Buffer Volume | | | 4.6 | | | | 3.0 |
| | Lysozyme Loading | | | 0.092 | | | | |
| 26 | 4ARM-20k-AA | 20000 | 1000 | 0.06 | 4 | 0.003 | 0.012 | |
| | 8ARM-20k-NH2 | 20000 | 1000 | 0.03 | 8 | 0.0015 | 0.012 | |
| | 4ARM-20k-SGA | 20000 | 1000 | 0.12 | 4 | 0.006 | 0.024 | |
| | Buffer Volume | | | 4.2 | | | | 5.0 |
| | Lysozyme Loading | | | 0.084 | | | | |
| 27 | 4ARM-20k-AA | 20000 | 1000 | 0.1 | 4 | 0.005 | 0.02 | |
| | 8ARM-20k-NH2 | 20000 | 1000 | 0.05 | 8 | 0.0025 | 0.02 | |
| | 8ARM-15k-SG | 15000 | 1000 | 0.075 | 8 | 0.005 | 0.04 | |
| | Buffer Volume | | | 4.5 | | | | 5.0 |
| | Lysozyme Loading | | | 0.09 | | | | |
| 28 | ETTMP-1300 | 1300 | 1000 | 0.046 | 3 | 0.035 | 0.11 | |
| | 8ARM-15k-SG | 15000 | 1000 | 0.2 | 8 | 0.013 | 0.11 | |
| | Buffer Volume | | | 5 | | | | 4.9 |
| | Lysozyme Loading | | | 0.1 | | | | |

About 5 grams of the polymer was weighed and placed in a Falcon tube. Two ml of phosphate buffer/gm of the polymer were added in the falcon tube. The falcon tube was placed in a water bath maintained at 37° C. After 24 hours, the buffer was carefully removed and replaced with fresh buffer to maintain a constant volume. The extraction process was repeated until the polymer is dissolved completely.

The extracts were collected and treated with Bradford reagent and the colors were analyzed and quantified. The results of the protein elution studies are summarized in Table 6.

TABLE 6

Protein Elution Studies of Lysozyme and BSA Hydrogel Formulations.

| Material ID | Polymer Components | Protein Loading | % Solution | Reaction Buffer | Gel Time (s) | Degradation Time (days) |
|---|---|---|---|---|---|---|
| 1 | 4ARM-20k-AA & 8ARM-15k-SG | 10 mg/mL BSA | 5 | 0.058M pH 7.97 | 105 | 8 |
| 2 | 4ARM-20k-AA & 8ARM-15k-SG | 10 mg/mL BSA | 5 | 0.058M pH 7.97 | 110 | 7 |
| 3 | 4ARM-20k-AA & 8ARM-15k-SG | 10 mg/mL BSA | 3 | 0.058M pH 7.97 | 135 | 6 |
| 4 | ETTMP-1300 & 8ARM-15k-SG | 10 mg/mL BSA | 7 | 0.05M pH 8.35 | 50 | 12 |
| 5 | 4ARM-20k-AA & 8ARM-15k-SG | 20 mg/mL Lysozyme | 5 | 0.058M pH 7.97 | 170 | 6 |
| 6 | ETTMP-1300 & 8ARM-15k-SG | 10 mg/mL BSA | 5 | 0.05M pH 7.93 | 160 | 10 |
| 7 | 4ARM-20k-AA & 4ARM-20k-SGA | 10 mg/mL BSA | 5 | 0.058M pH 7.97 | 170 | 7 |
| 8 | 4ARM-20k-AA & 4ARM-20k-SGA | 10 mg/mL BSA | 3 | 0.058M pH 7.97 | 230 | 4 |
| 9 | 4ARM-20k-AA/ 8ARM-20k-NH2 (50/50) & 4ARM-20k-SGA | 10 mg/mL BSA | 3 | 0.058M pH 7.97 | 200 | 32 |
| 10 | 4ARM-20k-AA & 4ARM-20k-SGA | 20 mg/mL Lysozyme | 5 | 0.058M pH 7.97 | 315 | 6 |

TABLE 6-continued

Protein Elution Studies of Lysozyme and BSA Hydrogel Formulations.

| Material ID | Polymer Components | Protein Loading | % Solution | Reaction Buffer | Gel Time (s) | Degradation Time (days) |
|---|---|---|---|---|---|---|
| 11 | 4ARM-20k-AA & 4ARM-10k-SG | 20 mg/mL Lysozyme | 5 | 0.058M pH 7.97 | 300 | 6 |
| 12 | 4ARM-20k-AA/ 8ARM-20k-NH2 (75/25) & 4ARM-20k-SGA | 10 mg/mL BSA | 3 | 0.058M pH 7.97 | 250 | 8 |
| 13 | 4ARM-10k-SS/ 4ARM-10k-SG (80/20) & 4ARM-5k-NH2 | 20 mg/mL Lysozyme | 5 | 0.058M pH 7.97 | 260 | 5 |
| 14 | ETTMP-1300 & 8ARM-15k-SG | 20 mg/mL Lysozyme | 5 | 0.05M pH 8.35 | 70 | 17 |
| 15 | 4ARM-20k-AA/ 8ARM-20k-NH2 (75/25) & 4ARM-20k-SGA | 20 mg/mL Lysozyme | 5 | 0.058M pH 7.97 | 280 | 9 |
| 16 | 4ARM-20k-AA & 8ARM-15k-SG | 10 mg/mL BSA | 2 | 0.058M pH 7.97 | 270 | 3 |
| 17 | 4ARM-20k-AA & 8ARM-15k-SG | 10 mg/mL BSA | 7 | 0.058M pH 7.97 | 100 | 9 |
| 18 | 4ARM-20k-AA & 8ARM-15k-SG | 10 mg/mL BSA | 8 | 0.058M pH 7.97 | 120 | 11 |
| 19 | 4ARM-20k-AA/ 8ARM-20k-NH2 (50/50) & 4ARM-20k-SGA | 10 mg/mL BSA | 3 | 0.058M pH 7.97 | 280 | 11 |
| 20 | 4ARM-20k-AA/ 8ARM-20k-NH2 (75/25) & 4ARM-20k-SGA | 20 mg/mL Lysozyme | 3 | 0.058M pH 7.97 | 600 | 3 |
| 21 | 4ARM-20k-AA/ 8ARM-20k-NH2 (50/50) & 4ARM-20k-SGA | 20 mg/mL Lysozyme | 3 | 0.058M pH 7.97 | 540 | 6 |
| 22 | 4ARM-20k-AA/ 8ARM-20k-NH2 (50/50) & 4ARM-20k-SGA | 10 mg/mL BSA | 3 | 0.1M pH 9.05 | 110 | 43 |
| 23 | 4ARM-20k-AA/ 8ARM-20k-NH2 (75/25) & 4ARM-20k-SGA | 10 mg/mL BSA | 3 | 0.1M pH 9.05 | 130 | 6 |
| 24 | 4ARM-20k-AA & 8ARM-15k-SG | 10 mg/mL BSA | 8 | 0.058M pH 7.97 | 120 | 10 |
| 25 | 4ARM-20k-AA/ 8ARM-20k-NH2 (50/50) & 4ARM-20k-SGA | 20 mg/mL Lysozyme | 3 | 0.1M pH 9.05 | 210 | 3 |
| 26 | 4ARM-20k-AA/ 8ARM-20k-NH2 (50/50) & 4ARM-20k-SGA | 20 mg/mL Lysozyme | 5 | 0.1M pH 9.05 | 130 | 17 |
| 27 | 4ARM-20k-AA/ 8ARM-20k-NH2 (50/50) & 8ARM-15k-SG | 20 mg/mL Lysozyme | 5 | 0.1M pH 9.05 | 70 | 15 |
| 28 | ETTMP-1300 & 8ARM-15k-SG | 20 mg/mL Lysozyme | 5 | 0.05M pH 8.35 | 70 | 35 |

The elution behavior of lysozyme with 4ARM-20k-AA and esters of various sizes was evaluated at a 5% solution concentration. Small proteins (like lysozyme) could be eluted from the polymer, but the protein size and pore size needed to be optimized (FIG. 1). In some instances, where the pore size of the hydrogel polymer is small, the elution of the protein is only partially complete until degradation starts and all of the protein is eluted (see FIG. 1, 4ARM-20k-AA/ 8ARM-15k-SG). The degradation time in all cases was 6 days with the onset of degradation beginning at day 3. The daily elution rate was typically between 10 and 20 percent. There was essentially no significant effect of ester size on the elution profile, although the largest ester, 4ARM-20k-SGA, appears to release the protein at the highest rate.

Large proteins (like BSA) did not elute from a hydrogel polymer with small pore sizes until degradation of the polymer started (FIG. 2A). However, large proteins do show early elution from the hydrogel polymer if the pore sizes are larger (FIG. 2B). Similarly, small proteins (like lysozyme) did not elute from a hydrogel polymer with very small pore sizes until the degradation of the hydrogel set in (FIG. 3). Thus, small pore sizes did not allow protein elution to occur until the degradation of the hydrogel polymer starts. This property could be useful for time delayed burst release of small and large proteins using custom designed hydrogel polymers with defined pore sizes. Furthermore, the early elution rate of the polymer could be controlled by the selection of pore sizes of the hydrogel polymer.

Figure 4:
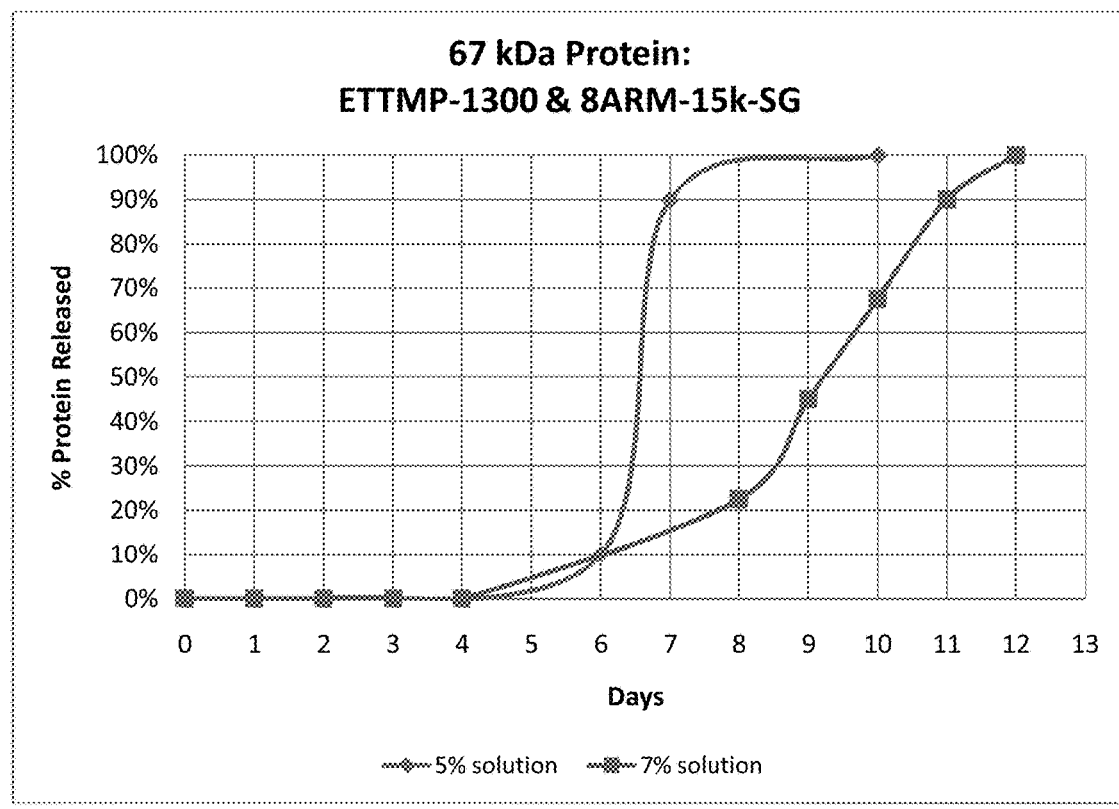
FIG. 4 shows the elution profile of a large protein (BSA) from a thiol-ester hydrogel polymer with small pore sizes at different solution concentrations.
Figure 5:
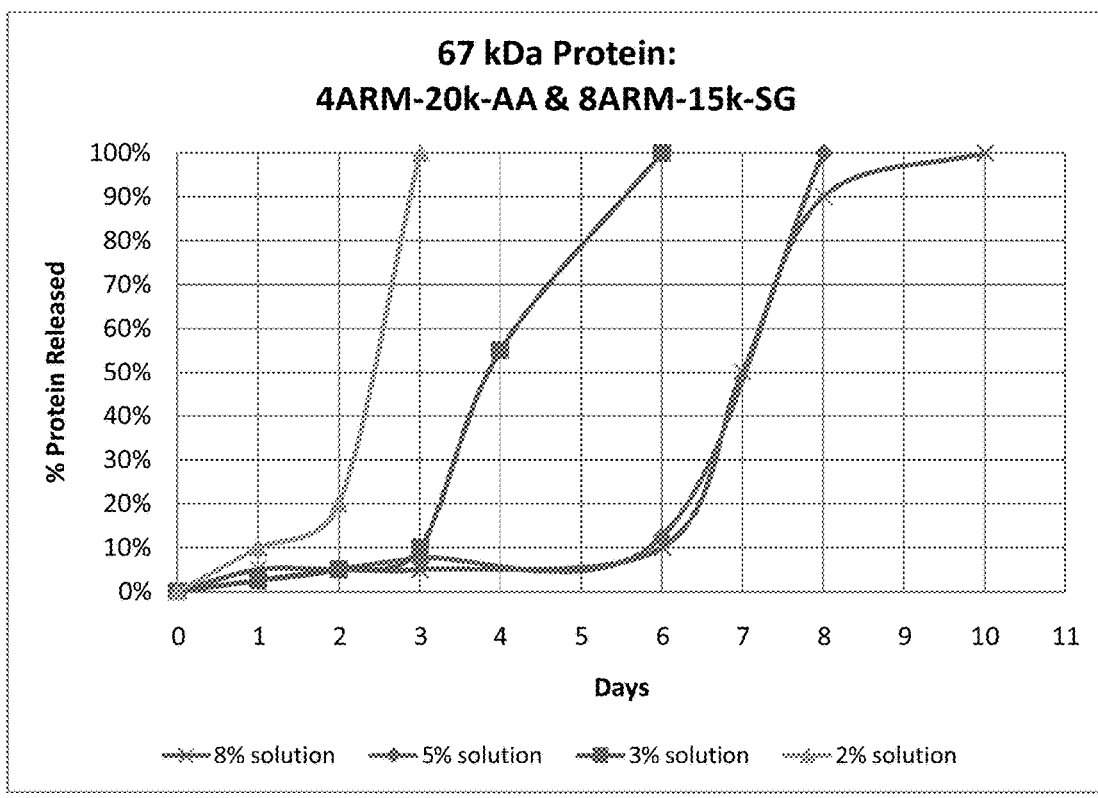
FIG. 5 shows the elution profile of a large protein (BSA) from an amine-ester hydrogel polymer with small pore sizes at different solution concentrations.

FIG. 4 shows the elution profile of BSA with ETTMP-1300 and 8ARM-15k-SG at 5% and 7% solution concentrations. No protein is released until the onset of degradation, which was observed at around day 6 in both cases. After day 6, the polymer either released the majority of the protein at once (5% solution formulation), or gradually (7% solution formulation). The elution of BSA from 4ARM-20k-AA and 8ARM-15k-SG polymers behaved similarly (FIG. 5). The majority of the protein is released at the onset of degradation, which was observed at around day 6 for the 5% solution formulation. However, there is a slight release of protein of about 2.5% daily before the onset of degradation. The more dilute solutions caused lower degrees of cross-linking during the hydrogel formation and hence shorter degradation times. The use of small pore sizes and defined degradation times through optimization of the solution concentrations could allow the control of release times.

Figure 6:
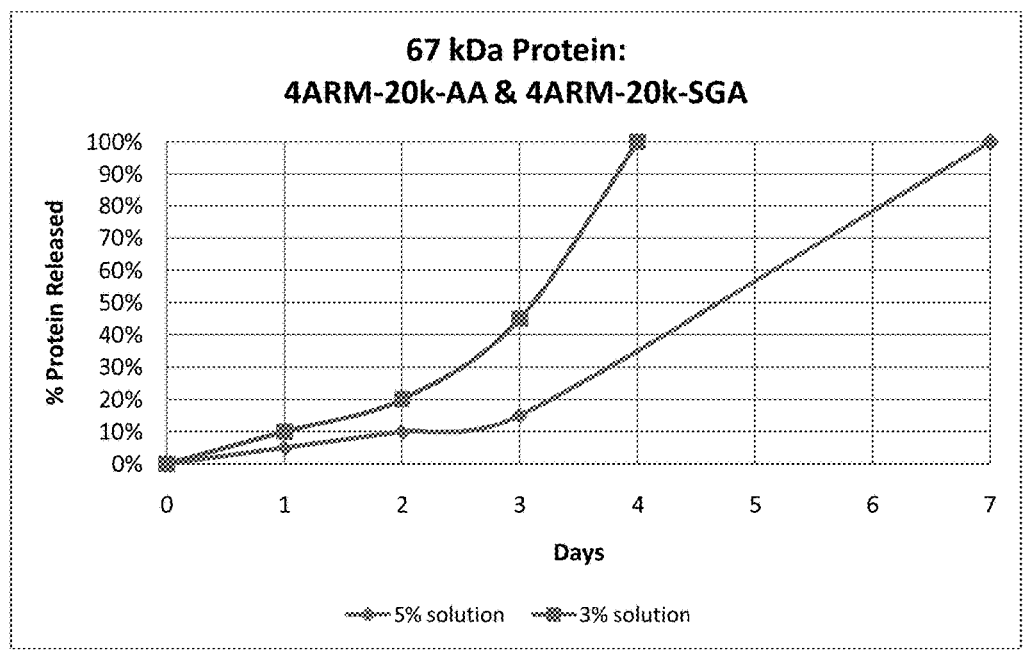
FIG. 6 shows the elution profile of a large protein (BSA) from an amine-ester hydrogel created from 4ARM-20k-AA with the largest available ester, 4ARM-20k-SGA, at different solution concentrations.

In formulations of 4ARM-20k-AA with the largest available ester, 4ARM-20k-SGA, the early time elution of BSA became apparent. FIG. 6 shows the elution profile BSA with 4ARM-20k-AA and 4ARM-20k-SGA at 3% and 5% solution concentrations. The 5% solution formulation exhibited a 5% daily protein release until the onset of degradation, which was observed at around day 3. The majority of the protein was released upon degradation. The 3% solution formulation exhibited a 10% daily protein release until the onset of degradation, which was observed between day 2 and day 3, with the remaining protein released upon degradation. The two-fold increase in released protein at early times is presumably from the increase in pore size from the swollen polymer matrix.

Figure 7:
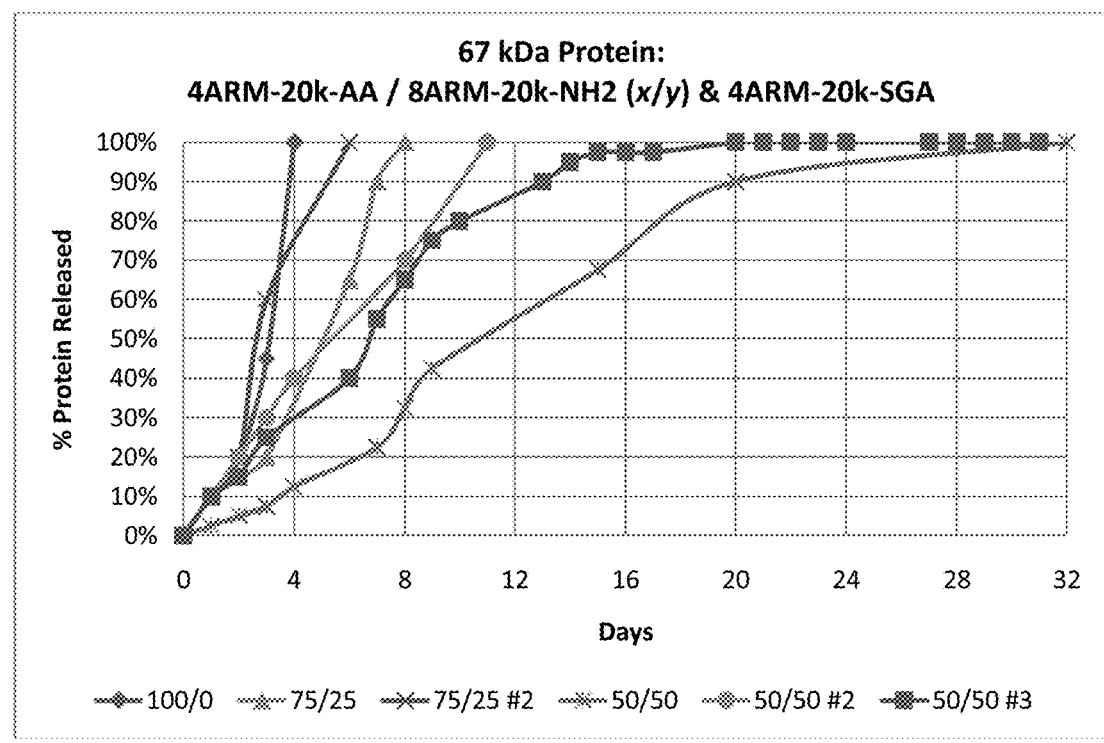
FIG. 7 shows the elution profile of a large protein (BSA) from a hydrogel created from 4ARM-20k-SGA with various ratios of the amine 4ARM-20k-AA and the non-degradable amine 8ARM-20k-NH2.

In some instances, degradation times increased upon the addition of a non-degradable amine, 8ARM-20k-NH2, to formulations with 4ARM-20k-AA. To further explore the elution of BSA from 4ARM-20k-AA and 4ARM-20k-SGA polymers with 3% solution, a formulation with a mixture of 4ARM-20k-AA and 8ARM-20k-NH2 in various ratios was used. The degradation time increased from 4 days to 32 days. FIG. 7 shows the corresponding elution profiles. Approximately 2.5% daily protein release was exhibited over a period of 7 days. Gradual degradation of the polymer began after day 7 and approximately 10% daily protein release was observed.

Figure 8:
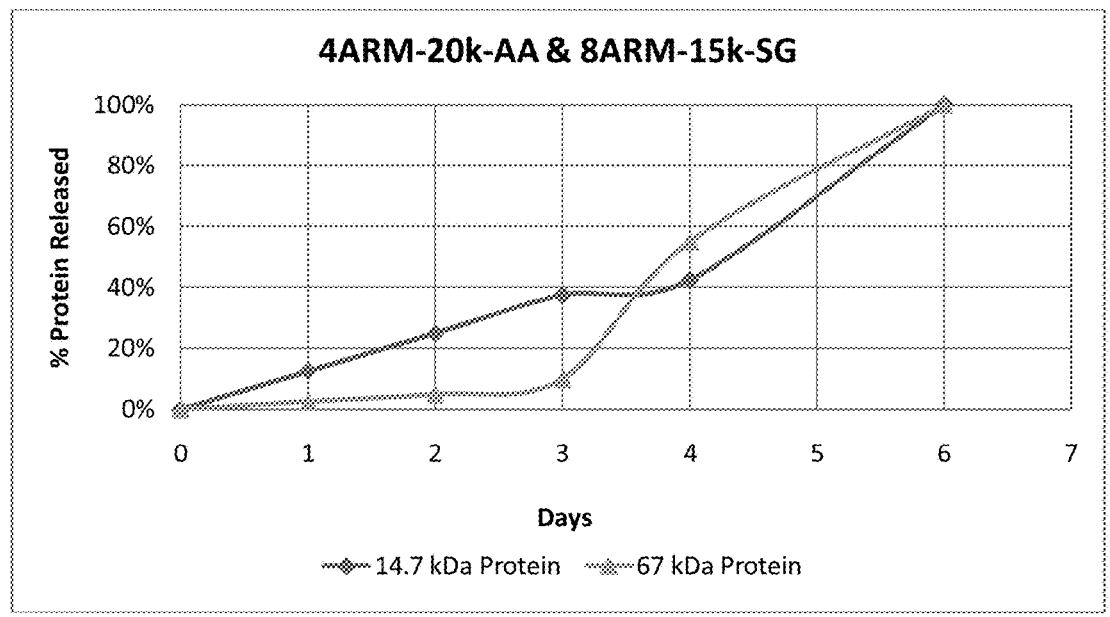
FIG. 8 shows the elution profile of a small (lysozyme) and large (BSA) protein from a formulation of 4ARM-20k-AA and 8ARM-15k-SG in a 3% solution.

A comparison of the elution of a small and a large protein from a 4ARM-20kAA & 8ARM-15k-SG hydrogel showed that the early elution of the large protein is slower compared to the small protein. There was essentially no elution of the large protein until the degradation had begun, but once degradation set in, the size of the protein was less relevant to the release rate of the protein from the polymer (see FIG. 8).

TABLE 7

Results of pore size estimation for various formulations, including relevant physical constants used in the calculation.

| Physical Constants | | |
|---|---|---|
| C—C bond | 0.154 | nm |
| C—C—C (110 degree angle) | 0.252 | nm/3C |
| BSA hydrodynamic diameter | 7 | nm |
| Lysozyme hydrodynamic diameter | 4 | nm |
| 1/Polymer Swelling Ratio ($V_p/V_s$) | 0.5 | |

| Monomer | MW | Arms | MW/Arm |
|---|---|---|---|
| ETTMP-1300 | 1300 | 3 | 433 |
| 4ARM-10K | 10000 | 4 | 2500 |
| 8ARM-15K | 15000 | 8 | 1875 |
| 4ARM-20K | 20000 | 4 | 5000 |
| 8ARM-20K | 20000 | 8 | 2500 |
| 4ARM-40K | 40000 | 4 | 10000 |
| 8ARM-40K | 40000 | 8 | 5000 |

| Material Components | MW/Arm | # of (—CH2—CH2—O—) Units/Arm | Swollen Pore Diameter (nm) | Pore Diameter (nm) | Pore Diameter to BSA Ratio | Swollen Pore Diameter to BSA Ratio | Pore Diameter to Lysozyme Ratio | Swollen Pore Diameter to Lysozyme Ratio |
|---|---|---|---|---|---|---|---|---|
| ETTMP-1300/ 8ARM-15k-SG | 2308 | 52.5 | 13.2 | 10.5 | 1.5 | 1.9 | 2.6 | 3.3 |
| 4ARM-20k-AA/ 4ARM-10k-SG | 7500 | 170.4 | 43.0 | 34.1 | 4.9 | 6.1 | 8.5 | 10.7 |
| 4ARM-20k-AA/ 8ARM-15k-SG | 6875 | 156.2 | 39.4 | 31.3 | 4.5 | 5.6 | 7.8 | 9.9 |
| 4ARM-20k-AA/ 4ARM-20k-SGA | 10000 | 227.2 | 57.3 | 45.5 | 6.5 | 8.2 | 11.4 | 14.3 |
| 8ARM-20k-NH2/ 4ARM-20k-SGA | 7500 | 170.4 | 43.0 | 34.1 | 4.9 | 6.1 | 8.5 | 10.7 |
| 4ARM-20k-AA/ 4ARM-40k-SG | 15000 | 340.8 | 86.0 | 68.3 | 9.8 | 12.3 | 17.1 | 21.5 |
| 4ARM-40k-NH2/ 4ARM-40k-SG | 20000 | 454.4 | 114.7 | 91.0 | 13.0 | 16.4 | 22.8 | 28.7 |

Figure 9:
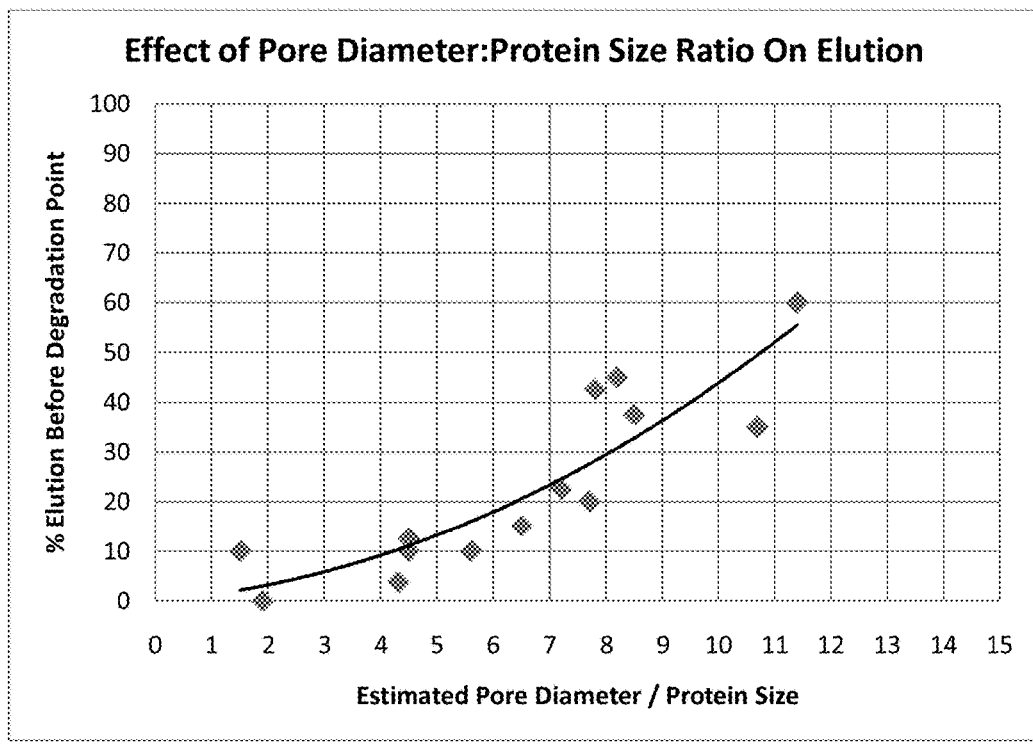
FIG. 9 demonstrates the relationship between the ratio of pore size to protein size and the percent elution before the degradation point of the hydrogel polymer (pore diameters are estimated while elution data is taken from experiment).

The results of the pore size estimation are shown in Table 7 along with the values of the physical parameters used. The pore diameters for the polymers were in the range of 10 to 100 nm. The effect of pore diameter to protein size ratio on early time elution is plotted in FIG. 9. The lack of significant outliers in the data set suggested that the rate of elution is not heavily influenced by the nature of the protein or polymer type, but rather the pore size relative to the protein size. A sharp rise in the protein elution occurred staring at a pore diameter to protein size ratio of about 8. Thus, an acceptable value for the ratio is expected to be between 8 and 12, which will be readily achieved if 4ARM monomers with a molecular weight of 40,000 are utilized with BSA.

Example 16: Clinical Trial for the Treatment of Osteoporosis with Teriparatide Hydrogel Polymer The study goal is to evaluate the safety and efficacy of an in vivo gelling pharmaceutical pre-formulation forming a biocompatible hydrogel polymer containing the peptide hormone teriparatide in the treatment of osteoporosis. The hydrogel polymer provides for a sustained release of the teriparatide peptide. Dosing frequencies of one injection every 2 weeks or every 4 weeks are evaluated.

The study endpoints are increase in bone mineral density in the lumbar spine, hip, and forearm, increase in bone formation biochemical markers serum P1CP (C-terminal propeptide of type I procollagen), P1NP (N-terminal propeptide of type I procollagen), alkaline phosphatase, osteocalcin, and increase in bone resorption biomarkers urinary pyridinoline and NTX (cross-linked N-telopeptide of type I collagen).

The patient population for the study is 100 male and female patients with osteoporosis. The inclusion criteria for admittance to the study are patients with clinical diagnosis of osteoporosis and bone mineral density T score of less than or equal to −2.5.

Prior to treatment, dual-energy x-ray absorptiometry (DXA) scan I performed to determine baseline bone mineral density scores in the lumbar spine, hip, and radius bones. Blood and urine are also collected to assess baseline bone biomarkers. The patient is then started on subcutaneous injections of teriparatide hydrogel polymer at a dose of approximately 20 micrograms released per day along with calcium (1000 mg/day) and vitamin-D (400-1200 I.U.) supplements.

Blood and urine are collected every 1 month and DXA scans performed every 3 months. The study is completed after 12 months. Changes in bone mineral density and bone biomarkers over 12 months as well as adverse events are compared to previously published results on daily teriparatide subcutaneous injections (Neer et al., *New Engl. J. Med.*, 2001, 344, 1434-1441; Marcus et al., *J. Bone Miner. Res.* 2003, 18, 18-23.).

Example 17: Clinical Trial for the Treatment of Drug Resistant HIV with Enfuvirtide Hydrogel Polymer The study goal is to evaluate the safety and efficacy of an in vivo gelling pharmaceutical pre-formulation forming a biocompatible hydrogel polymer containing the peptide enfuvirtide in the treatment of drug resistant HIV. The hydrogel polymer provides for a sustained release of the enfuvirtide peptide. Dosing frequencies of one injection every 1 week, 2 weeks, or 4 weeks are evaluated.

The study endpoints are changes in plasma HIV-1 RNA level and changes in CD4+ cell count after 24 weeks of therapy.

The patient population for the study is 100 male and female patients over the age of 18 with drug resistant HIV. The inclusion criteria for admittance to the study are patients with HIV who have never been on enfuvirtide and have treatment failure on anti-retroviral therapy (ART) due to drug-resistant virus.

Prior to treatment, blood is collected to determine HIV-1 RNA level, CD4+ count, and HIV resistance to enfuvirtide (mutations in HR1 region of gp41). The subjects continue on their optimized ART and enfuvirtide polymer is injected subcutaneously at a dose of approximately 180 mg released per day. Blood is drawn every 4 weeks to monitor HIV-1 RNA level and CD4+ cell count for a total of 24 weeks. HIV resistance to enfuvirtide is also assessed at 24 weeks to evaluate for development of resistance while on enfuvirtide polymer treatment.

Changes in HIV-1 RNA level and CD4+ cell count and adverse events on enfuvirtide sustained release polymer are compared to previously published clinical trials (TORO 1: Lalezari et al., *N. Engl. J. Med.*, 2003, 348, 2175-2185; TORO 2: Lazzarin et al., *N. Engl. J. Med.*, 2003, 348, 2186-2195) on enfuvirtide in this patient population to determine equivalent efficacy and safety.

Example 18: Clinical Trial for the Treatment of Rheumatoid Arthritis with Adalimumab Hydrogel Polymer The study goal is to evaluate the safety and efficacy of an in vivo gelling pharmaceutical pre-formulation forming a biocompatible hydrogel polymer containing the tumor necrosis-alpha (TNF-alpha) inhibitor adalimumab in the treatment of rheumatoid arthritis. The hydrogel polymer containing adalimumab provides for a local and sustained release of the adalimumab monoclonal antibody to minimize systemic side effects. Dosing frequencies of one injection every 1 week, 2 weeks, or 4 weeks are evaluated.

The study endpoints are 20%, 50%, and 70% improvement according to the American College of Rheumatology criteria (ACR20, 50, and 70), visual analog scale (VAS) for knee pain, morning stiffness, and edema, knee circumference and goniometry, Likert's scale of improvement, and daily use of oral glucorticoid and non-steroidal anti-inflammatory drugs (NSAIDs) at 24 weeks.

The patient population for the study is 100 male and female patients with rheumatoid arthritis and knee synovitis. The inclusion criteria for admittance to the study are patients over the age of 18 with clinical diagnosis of rheumatoid arthritis and knee synovitis not previously or currently on TNF-alpha inhibitors.

Prior to treatment, baseline disease activity is determined with parameters from the previously specified study endpoints. The patient is given one intraarticular injection of adalimumab polymer at approved systemic doses into the affected knee. Study parameters and adverse events are collected at baseline, 1 week, 4 weeks, 8 weeks, 12 weeks, 16 weeks, and 24 weeks. Reports of efficacy and adverse events are compared to previously published clinical trials of the TNF-alpha inhibitor studied.

Example 19: Clinical Trial for the Treatment of Hemophilia A with Recombinant Factor VIII The study goal is to evaluate the safety and efficacy of an in vivo gelling pharmaceutical pre-formulation forming a biocompatible hydrogel polymer containing recombinant Factor VIII in the prophylaxis treatment of hemophilia A. The hydrogel polymer containing recombinant Factor VIII provides for a sustained release of the recombinant Factor VIII. Dosing frequencies of one injection every 1 week, 2 weeks, or 4 weeks are evaluated.

The study endpoints are all joint bleeds and joint bleeds requiring treatment with factor replacement.

The patient population for the study is 100 male patients with severe hemophilia A (Factor VIII:C<1%) who are receiving on-demand or secondary prophylaxis treatment for bleeding. The inclusion criteria for admittance to the study are patients age 12-70 years with severe hemophilia A who had documented bleeds or injections in the 6 months before study entry.

Prior to treatment, baseline Factor VIII levels are measured. The patient is given Factor VIII hydrogel polymer subcutaneous injections at appropriate weight based dose and time intervals over 24 weeks. Patients keep an electronic diary of all bleeding events. Bleeding events requiring transfusion or factor replacement are noted separately. Factor VIII levels are measured at 1 week, 4 weeks, 8 weeks, 12 weeks, 16 weeks, and 24 weeks. Reports of bleeding events and adverse events are compared to previously published clinical trials of factor VIII prophylaxis.

What is claimed is:

1. An in vivo gelling pharmaceutical pre-formulation, comprising:
(a) one or more multi-ARM nucleophilic PEG monomers, wherein the multi-ARM PEG nucleophilic monomers comprise a polyol core, wherein the polyol core is selected from the group consisting of

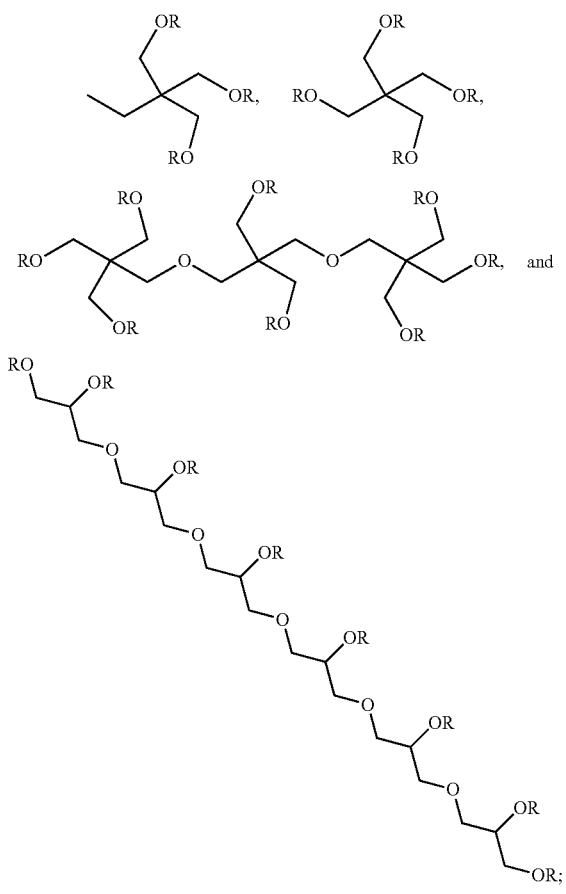

wherein the polyol core is substituted with 3-8 R-groups, wherein R is:

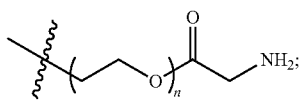

wherein n is 1-200;
(b) one or more multi-ARM nucleophilic PEG monomers, wherein the multi-ARM PEG nucleophilic monomers comprise a polyol core, wherein the polyol core is selected from the group consisting of

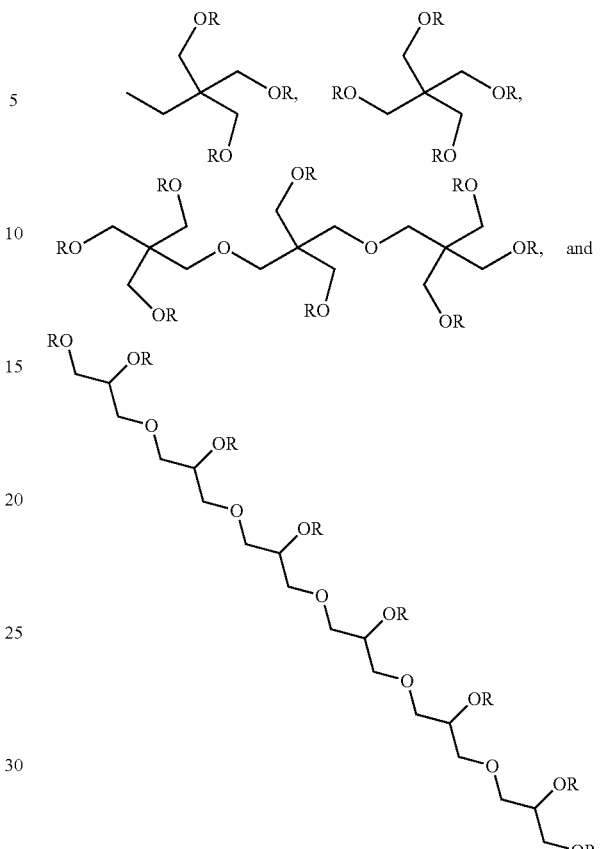

wherein the polyol core is substituted with 3-8 R-groups, wherein R is:

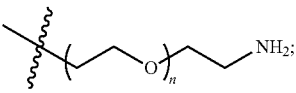

wherein n is 1-200;
(c) one or more multi-ARM-PEG electrophilic monomers having more than two electrophilic arms, wherein each electrophilic arm comprises a PEG chain and terminates in an electrophilic group;
(d) an aqueous buffer in the pH range of about 5.0 to about 9.5; and
(e) at least one pharmaceutically active biomolecule that is a monoclonal antibody;
wherein the in vivo gelling pharmaceutical pre-formulation at least in part polymerizes and/or gels at a target site of a human body to form a biocompatible hydrogel polymer,
wherein the molecular weight of the multi-ARM PEG nucleophilic monomers and/or the multi-ARM PEG electrophilic monomers is about 500 to about 40000.

2. The in vivo gelling pharmaceutical pre-formulation of claim 1, wherein the molecular weight of the multi-ARM PEG nucleophilic monomers and/or the multi-ARM PEG electrophilic monomers is about 15000 to about 40000.

3. The in vivo gelling pharmaceutical pre-formulation of claim 1, wherein the pharmaceutically active biomolecule is released from the biocompatible hydrogel polymer within 14 days.

4. The in vivo gelling pharmaceutical pre-formulation of claim 1, wherein the biocompatible hydrogel polymer has a pore size, wherein the pore size is small enough to essentially inhibit the release of the pharmaceutically active biomolecule before the time that the biocompatible hydrogel polymer starts to degrade, and wherein the ratio of the pore size of the biocompatible hydrogel polymer to the size of the pharmaceutically active biomolecule is less than 8.

5. The in vivo gelling pharmaceutical pre-formulation of claim 1, wherein the biocompatible hydrogel polymer has a pore size, wherein the pore size is large enough to allow at least a partial release of the pharmaceutically active biomolecule before the time that the biocompatible hydrogel polymer starts to degrade, and wherein the ratio of the pore size of the biocompatible hydrogel polymer to the size of the pharmaceutically active biomolecule is more than 8 and less than 12.

6. The biocompatible hydrogel polymer of claim 1.

7. The in vivo gelling pharmaceutical pre-formulation of claim 1, wherein the polyol core of the multi-ARM PEG nucleophilic monomer is:

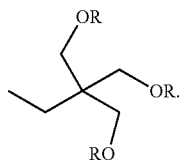

8. The in vivo gelling pharmaceutical pre-formulation of claim 1, wherein the polyol core of the multi-ARM PEG nucleophilic monomer is:

9. The in vivo gelling pharmaceutical pre-formulation of claim 1, wherein the polyol core of the multi-ARM PEG nucleophilic monomer is:

10. The in vivo gelling pharmaceutical pre-formulation of claim 1, wherein the polyol core of the multi-ARM PEG nucleophilic monomer is:

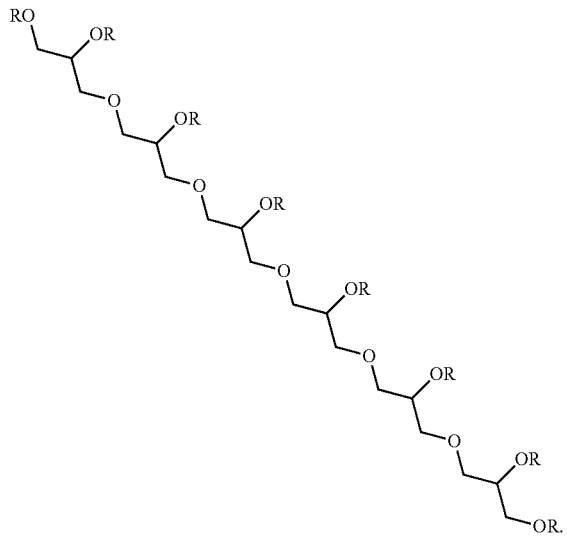

11. The in vivo gelling pharmaceutical pre-formulation of claim 1, wherein the antibody is an anti-CD20 antibody.

12. A biocompatible hydrogel polymer made by mixing:
(a) one or more multi-ARM nucleophilic PEG monomers, wherein the multi-ARM PEG nucleophilic monomers comprise a polyol core, wherein the polyol core is selected from the group consisting of

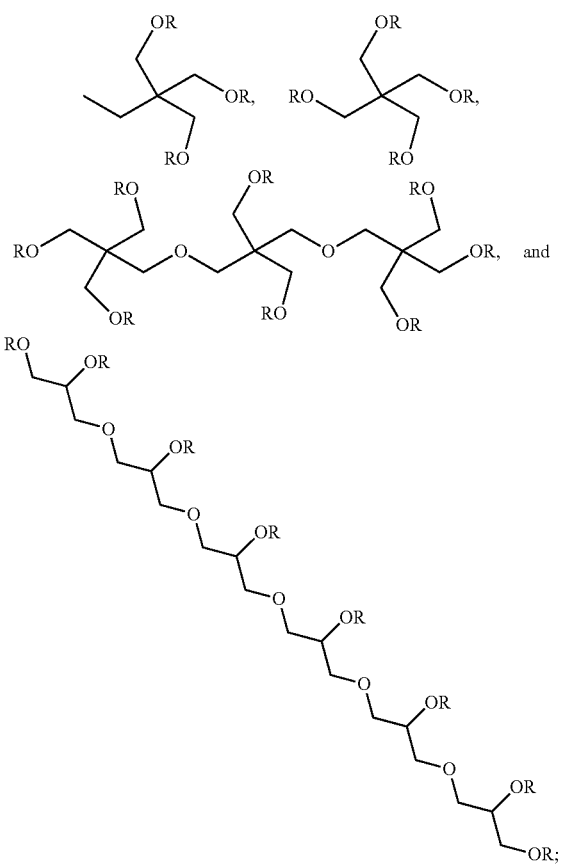

wherein the polyol core is substituted with 3-8 R-groups, wherein R is:

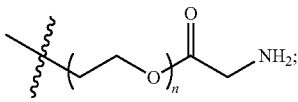

wherein n is 1-200;
(b) one or more multi-ARM nucleophilic PEG monomers, wherein the multi-ARM PEG nucleophilic monomers comprise a polyol core, wherein the polyol core is selected from the group consisting of

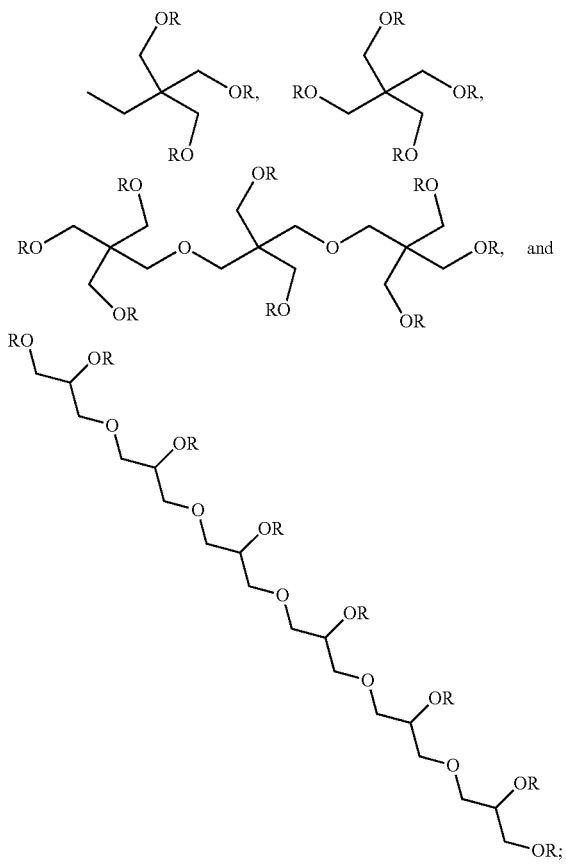

wherein the polyol core is substituted with 3-8 R-groups, wherein R is:

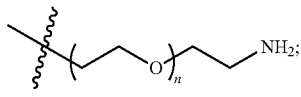

wherein n is 1-200;
(c) one or more multi-ARM-PEG electrophilic monomers having more than two electrophilic arms, wherein each electrophilic arm comprises a PEG chain and terminates in an electrophilic group;
(d) an aqueous buffer in the pH range of about 5.0 to about 9.5; and
(e) at least one pharmaceutically active biomolecule that is a monoclonal antibody,
wherein the molecular weight of the multi-ARM PEG nucleophilic monomers and/or the multi-ARM PEG electrophilic monomers is about 500 to about 40000.

13. The biocompatible hydrogel polymer of claim 12, wherein the mixing is performed outside a human body and the biocompatible hydrogel polymer gels at least in part inside the human body.

14. The biocompatible hydrogel polymer of claim 12, wherein the mixing is performed outside a human body, and the biocompatible hydrogel polymer gels outside the human body before delivery to a target site.

15. The biocompatible hydrogel polymer of claim 12, wherein the molecular weight of the multi-ARM PEG nucleophilic monomers and/or the multi-ARM PEG electrophilic monomers is about 15000 to about 40000.

16. The biocompatible hydrogel polymer of claim 12, wherein the pharmaceutically active biomolecule is released from the biocompatible hydrogel polymer within 14 days.

17. The biocompatible hydrogel polymer of claim 12, wherein the biocompatible hydrogel polymer has a pore size, wherein the pore size is small enough to essentially inhibit the release of the pharmaceutically active biomolecule before the time that the biocompatible hydrogel polymer starts to degrade, and wherein the ratio of the pore size of the biocompatible hydrogel polymer to the size of the pharmaceutically active biomolecule is less than 8.

18. The biocompatible hydrogel polymer of claim 12, wherein the biocompatible hydrogel polymer has a pore size, wherein the pore size is large enough to allow at least a partial release of the pharmaceutically active biomolecule before the time that the biocompatible hydrogel polymer starts to degrade, and wherein the ratio of the pore size of the biocompatible hydrogel polymer to the size of the pharmaceutically active biomolecule is more than 8 and less than 12.

* * * * *